(12) United States Patent
Yang et al.

(10) Patent No.: US 9,096,601 B2
(45) Date of Patent: Aug. 4, 2015

(54) ARYLAMINO PURINE DERIVATIVES, PREPARATION METHOD AND PHARMACEUTICAL USE THEREOF

(75) Inventors: Shengyong Yang, Chengdu (CN); Yuquan Wei, Chengdu (CN)

(73) Assignees: CSPC Zhongqi Pharmaceutical Technology (Shijiazhuang) Co., Ltd., Shijiazhuang, Hebei Province (CN); Sichuan University, Chengdu, Sichuan Province (CN)

( * ) Notice: Subject to any disclaimer, the term of this patent is extended or adjusted under 35 U.S.C. 154(b) by 40 days.

(21) Appl. No.: 13/699,960

(22) PCT Filed: Dec. 23, 2010

(86) PCT No.: PCT/CN2010/002126
§ 371 (c)(1),
(2), (4) Date: Jan. 22, 2013

(87) PCT Pub. No.: WO2011/147066
PCT Pub. Date: Dec. 1, 2011

(65) Prior Publication Data
US 2013/0203986 A1 Aug. 8, 2013

(30) Foreign Application Priority Data
May 26, 2010 (CN) .......................... 2010 1 0184478

(51) Int. Cl.
*C07D 473/16* (2006.01)
*C07D 473/18* (2006.01)
*C07D 473/32* (2006.01)

(52) U.S. Cl.
CPC ............ *C07D 473/32* (2013.01); *C07D 473/16* (2013.01); *C07D 473/18* (2013.01)

(58) Field of Classification Search
CPC .................... C07D 473/16; C07D 473/18
See application file for complete search history.

(56) References Cited

U.S. PATENT DOCUMENTS

| 7,256,196 B1 | 8/2007 | Sabat et al. | |
|---|---|---|---|
| 7,723,340 B2 | 5/2010 | Albers | |
| 2008/0021048 A1* | 1/2008 | Bennett et al. | 514/263.23 |

FOREIGN PATENT DOCUMENTS

| CA | 2740471 | 4/2010 |
|---|---|---|
| CN | 101142215 | 3/2008 |
| EP | 2172461 | 4/2010 |
| WO | 2005/097135 | 10/2005 |

OTHER PUBLICATIONS

Tumor definition in National Cancer Institute—www.cancer.gov—Mar. 23, 2009.*
Cancer definition in MedicineNet.com—Sep. 18, 2004.*
stomach cancer—Mayoclinic.com—Apr. 9, 2011.*
Adult Brain Tumors Treatment, National Cancer Institute, pp. 1-21 (Jan. 24, 2013).*
Types of Brain Cancer at http://www.cancercenter.com/brain-cancer/types-of-brain-cancer.cfm (Mar. 12, 2013).*
"Colorectal Cancer" at cancer.net (published Sep. 2012), pp. 1-2.*
Cancer Drug Design and Discovery Neidle, Stephen, ed. (Elsevier/Academic Press, 2008) p. 427-431.*
Divers et al. (Cutis. 2004, vol. 73, No. 4, pp. 257-262).*
Johnson et al. (British J. of Cancer, 2001, 84(10):1424-1431).*
Lens (Br. J. Nurs., 2008, vol. 17, No. 5, pp. 300-305).*
PCT/CN2010/002126 International Search Report, Mar. 31, 2011.
Das et al., "Dithiocarbamate and CuO promoted one-pot synthesis of 2(N-substituted)-aminobenzimidazoles and related heterocycles", Tetrahedron Letters, 2008, 49: 992-995.
Sabat et al., "The Development of Novel C-2, C-8 and N-9 Trisubstituted Purines as Inhibitors of TNF-α Production," Bioorganic & Medicinal Chemistry Letters, vol. 16, No. 16, pp. 4360-4365 (2006).
Supplemental European Search Report, Application No. EP 10851938.0 dated Sep. 27, 2013, 11 pages.

* cited by examiner

*Primary Examiner* — Valerie Rodriguez-Garcia
(74) *Attorney, Agent, or Firm* — Kilpatrick Townsend & Stockton LLP

(57) ABSTRACT

Arylamino purine derivatives represented by formula I and their preparation method are disclosed, wherein each substituent is defined as in the description. The derivatives have an inhibitory effect on non-small cell lung cancer with deletion mutation of exon 19 or L858R point mutation of exon 21 in epidermal growth factor receptor (EGFR).

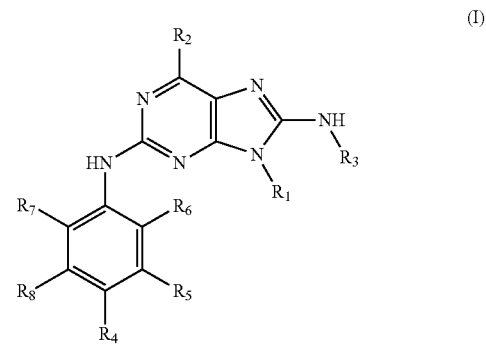

12 Claims, 2 Drawing Sheets

ARYLAMINO PURINE DERIVATIVES, PREPARATION METHOD AND PHARMACEUTICAL USE THEREOF

TECHNICAL FIELD

The present invention relates to the organically synthesized pharmaceutical field and in particular to arylamino purine derivatives, preparation method and pharmaceutical use thereof.

BACKGROUNDS

Malignant tumor is one of the most severe diseases threatening the human physical health, and has become the second leading cause of death, right behind the cardiovascular disease.

Moreover, the most recent statistical data indicate that the incidence rate and the death rate of malignant tumor are rising up year by year all over the world, especially in the developing countries.

The chemotherapy is the most important treatment means for malignant tumor besides operation and radiotherapy. The traditional chemotherapeutics mainly act on DNA, RNA, microtubule protein and the like, which are the common parts involving the life and death of all cells, and therefore have low selectivity and high toxicity. The targeted medicines act on the key molecules in the tumor cell, which regulate the cell growth and proliferation and are quite different from the normal cell, and their signal transduction pathways. They have the advantages such as a high selectivity on the tumor cells and low toxicity to normal tissues, and therefore become a hot point in the study of anti-tumor drug.

In many of molecules regulating signal transduction pathway of the cell, the family of protein kinases is the most important signal transduction molecule. It is found in the study that the occurrence and development of many tumors are relevant to the gene abnormality or excess activation of protein kinase. Therefore, protein kinases have become the most important anti-tumor treatment target. Tyrosine or serine/threonine protein kinase such as EGFR (Epidermal Growth Factor Receptor), VEGFR (Vascular Endothelial Growth Factor Receptor), PDGFR (Platelet Derived Growth Factor Receptor), c-Kit, c-SRC, MET, BTK, ALK, Abl, and FLT3 are most important among the members of the family of protein kinases, and have been listed as oncogene or oncoprotein.

Currently, more than 10 small molecule inhibitors targeting these tyrosine and serine/threonine protein kinases have been applied to clinical tumor treatment. The typical example includes: two EGFR inhibitors, i.e., Gefitinib and Erlotinib, mainly useful for the treatment of non-small cell lung carcinoma; two new-vessel inhibitors (their main targets are VEGFR, PDGFR and the like), i.e., Sunitinib and Sorafenib, useful for the anti-new-vessels treatment in the solid tumor; and Bcr-Abl kinase inhibitor Imatinib, mainly useful for the treatment of chronic myelocytic leukemia with positive Philadelphia chromosome.

However, these current antitumor drugs target a single or a very small number of kinase oncogenes or oncoproteins and therefore have the disadvantages such as low efficiency and being prone to develop the drug resistance. The typical example includes EGFR kinase inhibitors Gefitinib and Erlotinib. These two drugs have good effects on only 10-20% of patients with non-small cell lung carcinoma. It is found in the study on its mechanism of action that Gefitinib and Erlotinib belong to the selective EGFR kinase inhibitor, and are most sensitive to the patients having deletion mutation of exon 19 or L858R point mutation of exon 21 in EGFR (deletion mutation of exon 19 and L858R point mutation of exon 21 in EGFR are collectively referred to as EGFR sensitive mutation). Even if these patients with EGFR sensitive mutation are treated with Gefitinib and Erlotinib, most of them have developed the drug resistance after 6-9 months. It is found that there are many reasons for the development of the drug resistance, which mainly include (1) a second mutation occurs based on EGFR sensitive mutation, i.e., T790M mutation in EGFR; and (2) MET gene (MET is a tyrosine kinase) is subjected to amplification.

Solving the low efficiency and the drug resistance of small molecule kinase inhibitor antitumor drug is not only a hot point in the study but also a task of top priority. Currently, the researchers and scientists are exploring the effective solutions, in which the most promising solutions mainly include: (1) a multiple-kinase inhibitor that simultaneously targets multiple kinases relevant to the occurrence and development of tumor; (2) directly targeting the kinase that has developed the drug-resistant mutation. For example, EGFR is over expressed or abnormally and excessively activated in several tumor tissues of human. If a certain small molecule kinase inhibitor not only can inhibit the activity of EGFR, but also can inhibit the new-vessels or the activity of the oncogene or oncoprotein of the other key kinases regulating the cell growth and proliferation, e.g. kinases such as c-Kit, c-SRC, MET, BTK, ALK, Abl and FLT3, it can improve the efficiency of tumor treatment and reduce the occurrence rate of the drug resistance. For example, as stated hereinbefore, after EGFR inhibitors Gefitinib and Erlotinib are used, EGFR itself is prone to experience a second mutation based on the original mutation (i.e., EGFR sensitive mutation), i.e., T790M mutation in EGFR. The occurrence of this second mutation is one of the main reasons causing EGFR inhibitors Gefitinib and Erlotinib to be ineffective. Therefore, the research and development of an EGFR kinase inhibitor that directly targets the drug resistant mutation (i.e. T790M mutation) is a direct approach of overcoming the drug resistance of this tumor.

SUMMARY OF INVENTION

A technical solution to be solved in the present invention is to provide an arylamino purine derivative represented by formula (I).

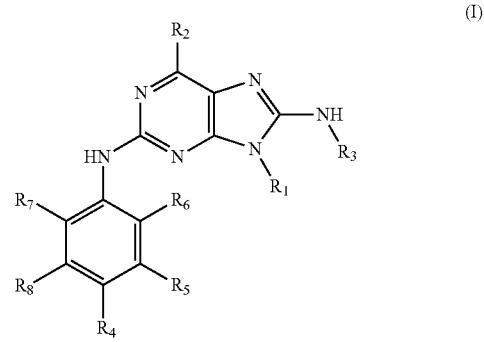

(I)

$R_1$ represents —H, —$C_mH_{(2m+1)}$, $C_3$-$C_7$cycloalkyl, —$C_mH_{(2m+1)}$ substituted by $C_3$-$C_7$cycloalkyl, $C_3$-$C_7$cycloalkyl substituted by —$C_mH_{(2m+1)}$, heterocyclyl containing 3-8 carbon atoms, amino substituted by heterocyclyl containing 3-8 carbon atoms, aryl containing 6-8 carbon atoms, or heteroaryl containing 6-8 carbon atoms; said heterocyclyl contains 1-3 heteroatoms selected from N, O and S; said heteroaryl contains 1-3 heteroatoms selected from N, O and S;

$R_2$ represents —H, —$NH_2$, —OH, —F, —Cl, —Br, —$CF_3$, —$C_mH_{(2m+1)}$, —$OC_mH_{(2m+1)}$, —$NHC_mH_{(2m+1)}$, aryloxy containing 6-12 carbon atoms, or arylamino containing 6-12 carbon atoms;

$R_3$ represents $C_3$-$C_7$cycloalkyl, $C_3$-$C_7$cycloalkyl substituted by —$C_mH_{(2m+1)}$, aryl containing 6-80 carbon atoms, or heteroaryl containing 6-80 carbon atoms; said heteroaryl contains 1-15 heteroatoms selected from N, O and S;

$R_4$-$R_8$ respectively represent —H, —F, —Cl, —Br, —$CF_3$, —$OCF_3$, —$OC_mH_{(2m+1)}$,

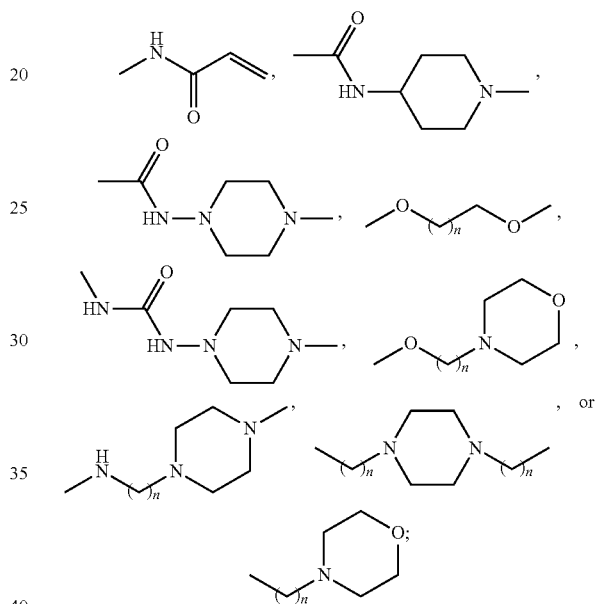

m = 1-8; and n = 0-4.

Said aryl containing 6-8 carbon atoms may be an aryl only containing C and H, or may be an aryl having a substituent, wherein said substituent can be —$NH_2$, —OH, —F, —Cl, —Br, —$CF_3$, —$C_yH_{(2y+1)}$, —$OC_yH_{(2y+1)}$ and/or —$NHC_yH_{(2y+1)}$, where y=1-5. Said aryl having a substituent can contain 0-8 nitrogen or oxygen heteroatoms; and Said heteroaryl may be a heteroaryl only containing C, H, N, O or S, or may be a heteroaryl having a substituent, wherein said heteroaryl can be —$NH_2$, —OH, —F, —Cl, —Br and/or —$CF_3$.

Preferably, the arylamino purine derivative is represented by formula (I), wherein $R_1$ represents —H, —$C_mH_{(2m+1)}$, $C_3$-$C_7$cycloalkyl substituted by —$C_mH_{(2m+1)}$, —$C_mH_{(2m+1)}$ substituted by $C_3$-$C_7$cycloalkyl, or $C_3$-$C_7$cycloalkyl;

$R_2$ represents —H, —$NH_2$, —OH, —F, —Cl, —Br, —$CF_3$, —$C_mH_{(2m+1)}$, —$OC_mH_{(2m+1)}$, or —$NHC_mH_{(2m+1)}$;

$R_3$ represents

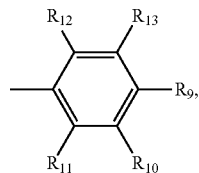

pyrimidinyl, halopyrimidinyl, $C_3$-$C_7$cycloalkyl, or $C_3$-$C_7$cycloalkyl substituted by —$C_mH_{(2m+1)}$;

$R_4$-$R_8$ respectively represent —H, —F, —Cl, —Br, —$CF_3$, —$OCF_3$, —$OC_mH_{(2m+1)}$, $R_9$-$R_{13}$ respectively represent —H, —F, —Cl, —Br, —$CF_3$, —$OCF_3$, —CN, —$C_mH_{(2m+1)}$, —$OC_mH_{(2m+1)}$,

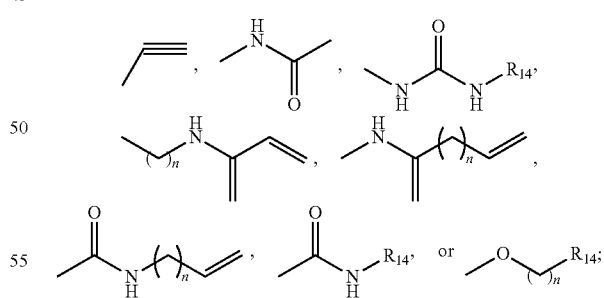

$R_{14}$ represents aryl or heteroaryl containing 6-10 carbon atoms; said heteroaryl contains 1-3 heteroatoms selected from N, O and S; m=1-8; and n=0-4.

Preferably, the arylamino purine derivative is represented by formula (I), wherein $R_1$ represents —H, —$C_mH_{(2m+1)}$, $C_3$-$C_7$cycloalkyl substituted by —$C_mH_{(2m+1)}$, —$C_mH_{(2m+1)}$ substituted by $C_3$-$C_7$cycloalkyl, or $C_3$-$C_7$cycloalkyl;

$R_2$ represents —H, —F, —Cl, —Br, —CF$_3$, —C$_m$H$_{(2m+1)}$, —OC$_m$H$_{(2m+1)}$, or —NHC$_m$H$_{(2m+1)}$;
$R_3$ represents

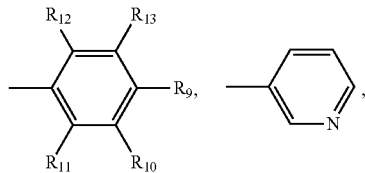

halopyrimidin-3-yl, C$_3$-C$_7$cycloalkyl, or C$_3$-C$_7$cycloalkyl substituted by —C$_m$H$_{(2m+1)}$;
$R_4$-$R_8$ respectively represent —H, —F, —Cl, —Br, —CF$_3$, —OC$_m$H$_{(2m+1)}$,

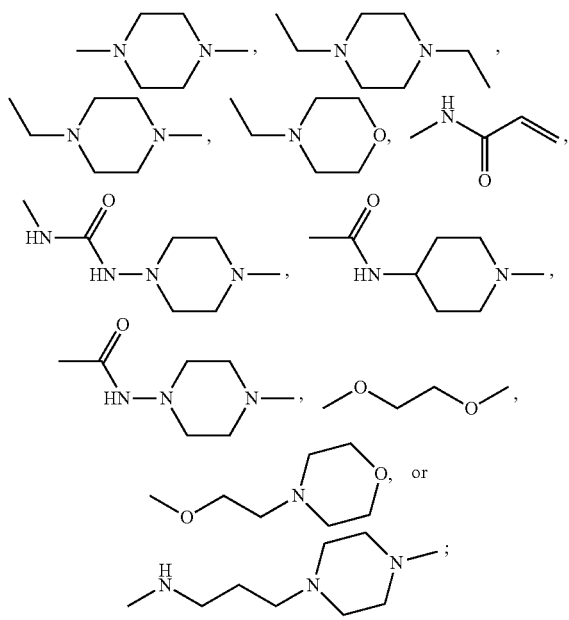

$R_9$-$R_{13}$ respectively represent —H, —F, —Cl, —Br, —CF$_3$, —CN, —C$_m$H$_{(2m+1)}$, —OC$_m$H$_{(2m+1)}$,

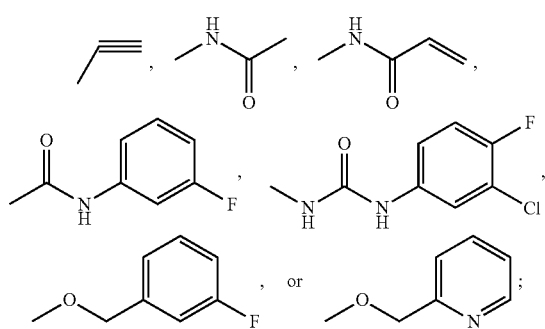

and
m=1-8.
Most preferably, the arylamino purine derivative is represented by formula (I), wherein
$R_1$ represents —H, —C$_m$H$_{(2m+1)}$, —C$_m$H$_{(2m+1)}$ substituted by C$_3$-C$_2$cycloalkyl, or C$_3$-C$_2$cycloalkyl;

$R_2$ represents —H, —C$_m$H$_{(2m+1)}$, —OC$_m$H$_{(2m+1)}$, —NHC$_m$H$_{(2m+1)}$;
$R_3$ represents

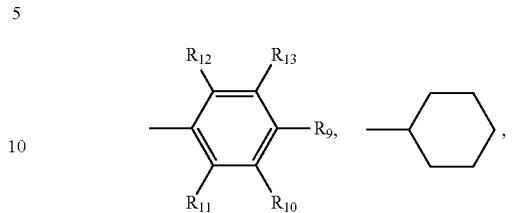

halopyrimidin-3-yl, or

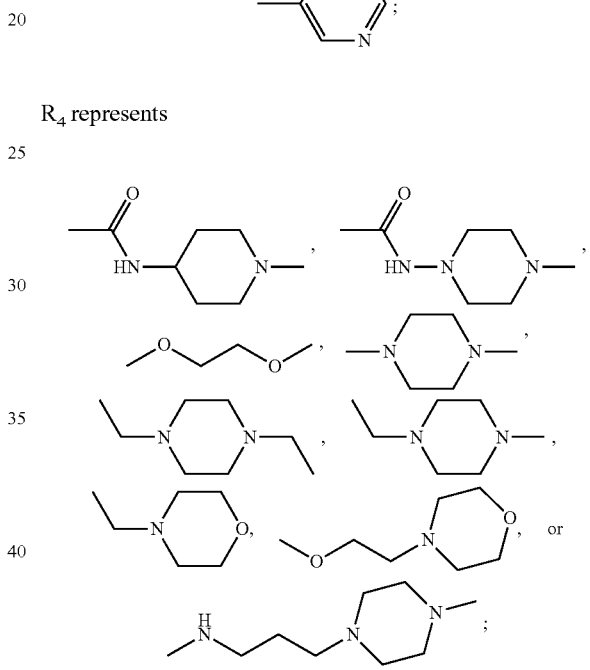

$R_5$-$R_8$ respectively represent —H, —F, —Cl, —Br, —CF$_3$, or —OC$_m$H$_{(2m+1)}$;
$R_9$-$R_{13}$ respectively represent —H, —F, —Cl, —Br, CF$_3$, —C$_m$H$_{(2m+1)}$, —OC$_m$H$_{(2m+1)}$,

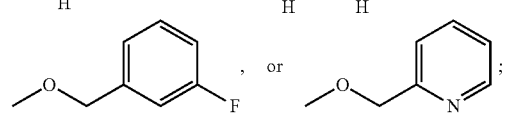

m=1-8.

Further, the arylamino purine derivative is represented by formula (II), wherein

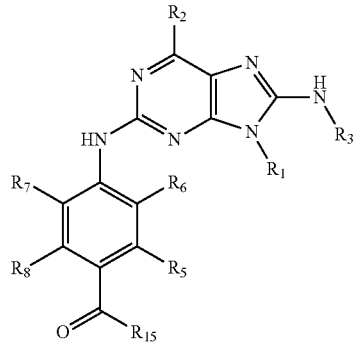

R$_1$ represents —H, —C$_m$H$_{(2m+1)}$, —C$_6$H$_5$, —C$_m$H$_{(2m+1)}$ substituted by C$_3$-C$_2$cycloalkyl, C$_3$-C$_2$cycloalkyl, or C$_3$-C$_2$cycloalkyl substituted by —C$_m$H$_{(2m+1)}$;

R$_2$ represents —H, —NH$_2$, —OH, —F, —Cl, —Br, —CF$_3$, —C$_m$H$_{(2m+1)}$, —OC$_m$H$_{(2m+1)}$, —NHC$_m$H$_{(2m+1)}$, aryloxy containing 6-12 carbon atoms, or arylamino containing 6-12 carbon atoms;

R$_3$ represents C$_3$-C$_2$cycloalkyl, C$_3$-C$_2$cycloalkyl substituted by —C$_m$H$_{(2m+1)}$, aryl containing 6-80 carbon atoms or heteroaryl containing 6-80 carbon atoms; said heteroaryl contains 1-15 heteroatoms selected from N, O and S;

R$_5$-R$_8$ respectively represent —H, —F, —Cl, —Br, —CF$_3$, —OCF$_3$, —OC$_m$H$_{(2m+1)}$,

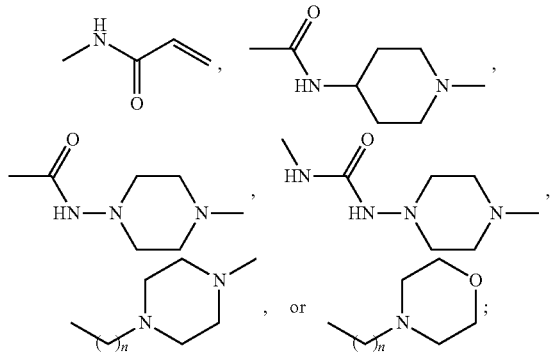

R$_{15}$ represents

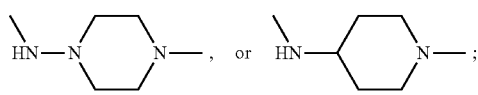

m=1-8; and
n=0-4.

Preferably, the arylamino purine derivative is represented by formula (II), wherein R$_1$ represents —H, —C$_m$H$_{(2m+1)}$, —C$_m$H$_{(2m+1)}$ substituted by C$_3$-C$_7$cycloalkyl, or C$_3$-C$_7$cycloalkyl;

R$_2$ represents —H, NH$_2$, OH, —F, —Cl, —Br, —CF$_3$, —C$_m$H$_{(2m+1)}$, —OC$_m$H$_{(2m+1)}$, or —NHC$_m$H$_{(2m+1)}$;

R$_3$ represents

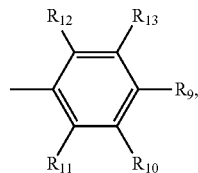

pyrimidinyl, halopyrimidinyl, C$_3$-C$_7$cycloalkyl, or C$_3$-C$_7$cycloalkyl substituted by —C$_m$H$_{(2m+1)}$;

R$_5$-R$_8$ respectively represent —H, —F, —Cl, —Br, —CF$_3$, —OC$_m$H$_{(2m+1)}$,

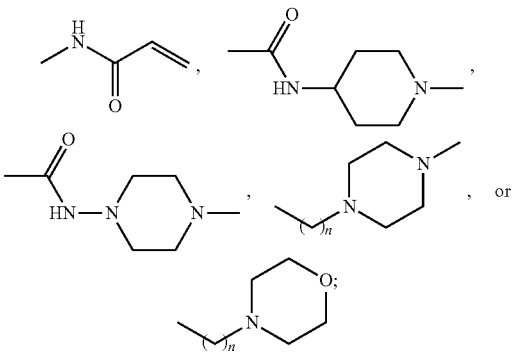

R$_9$-R$_{13}$ respectively represent —H, —F, —Cl, —Br, —CF$_3$, —CN, —C$_m$H$_{(2m+1)}$,

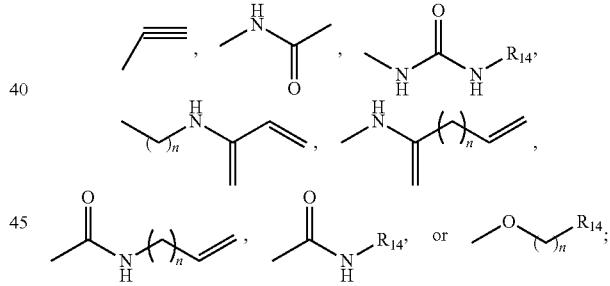

R$_{14}$ represents aryl or heteroaryl containing 6-10 carbon atoms; said heteroaryl contains 1-3 heteroatoms selected from N, O and S;

R$_{15}$ represents

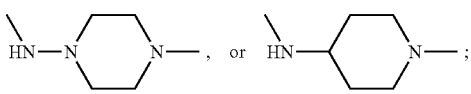

m=1-8; and
n=0-4.

Preferably, the arylamino purine derivative is represented by formula (II), wherein R$_1$ represents —H, —C$_m$H$_{(2m+1)}$, or C$_3$-C$_7$cycloalkyl;

R$_2$ represents —H, —F, —Cl, —Br, —CF$_3$, —C$_m$H$_{(2m+1)}$, —OC$_m$H$_{(2m+1)}$, or —NHC$_m$H$_{(2m+1)}$;

$R_3$ represents

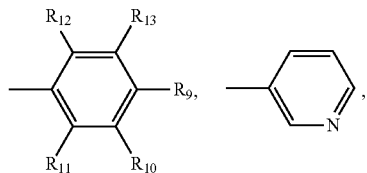

halopyrimidin-3-yl, $C_3$-$C_7$cycloalkyl, or $C_3$-$C_7$cycloalkyl substituted by —$C_mH_{(2m+1)}$;

$R_5$-$R_8$ respectively represent —H, —F, —Cl, —Br, —$CF_3$, —$OCF_3$, —$OC_mH_{(2m+1)}$,

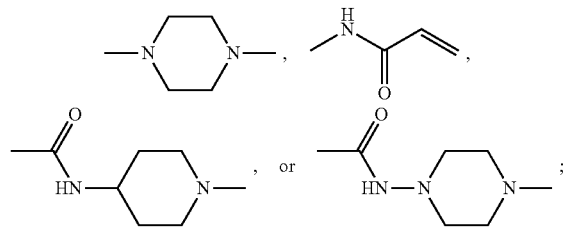

$R_9$-$R_{13}$ respectively represent —H, —F, —Cl, —Br, —$CF_3$, —CN, —$C_mH_{(2m+1)}$, —$OC_mH_{(2m+1)}$,

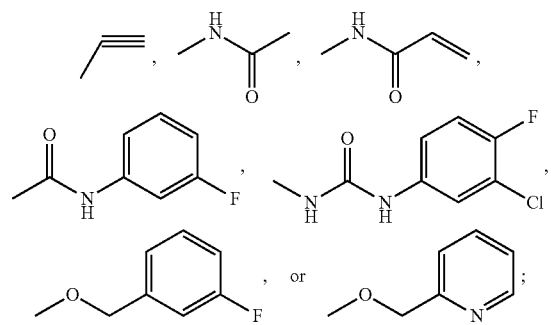

$R_{15}$ represents

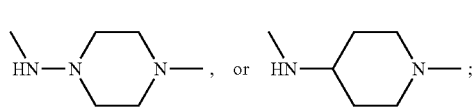

and
m=1-8.

Preferably, the arylamino purine derivative is represented by formula (II), wherein
$R_1$ represents —H, —$C_mH_{(2m+1)}$,

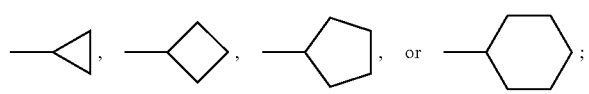

$R_2$ represents —H;

$R_3$ represents

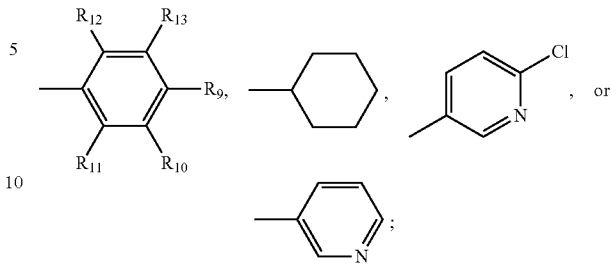

$R_5$-$R_8$ respectively represent —H, —F, —Cl, —Br, —$CF_3$, or —$OC_mH_{(2m+1)}$;
$R_9$-$R_{13}$ respectively represent —H, —F, —Cl, —Br, $CF_3$, —$C_mH_{(2m+1)}$, —$OC_mH_{(2m+1)}$,

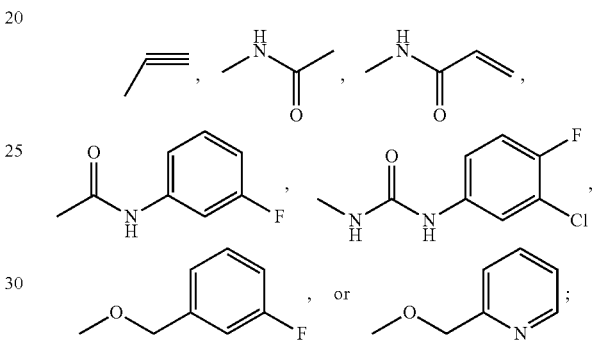

$R_{15}$ represents

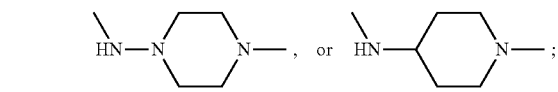

and
m=1-8.

Most preferably, the arylamino purine derivative is represented by formula (II), wherein
$R_1$ represents —H, —$C_mH_{(2m+1)}$,

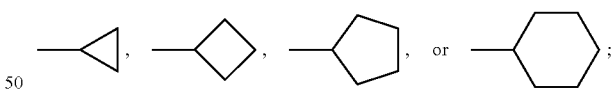

$R_2$ represents —H:
$R_3$ represents

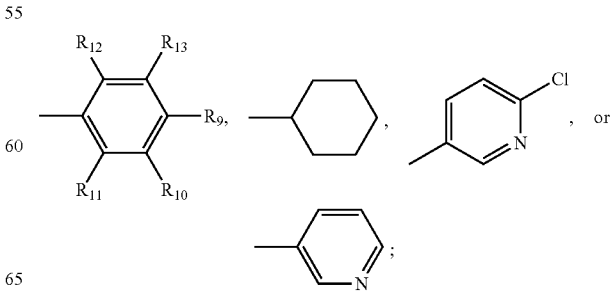

$R_5$-$R_8$ respectively represent —H, —F, —Cl, —Br, —CF$_3$, or —OC$_m$H$_{(2m+1)}$;

$R_8$-$R_{13}$ respectively represent —H, —F, —Cl, —Br, —CF$_3$, —C$_m$H$_{(2m+1)}$, —OC$_m$H$_{(2m+1)}$,

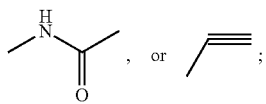, or 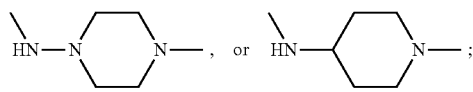 (partial);

$R_{15}$ represents

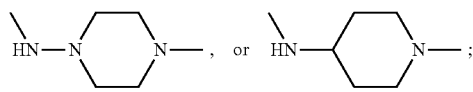

and
m=1-8.

Further, the arylamino purine derivative is represented by formula (III), wherein

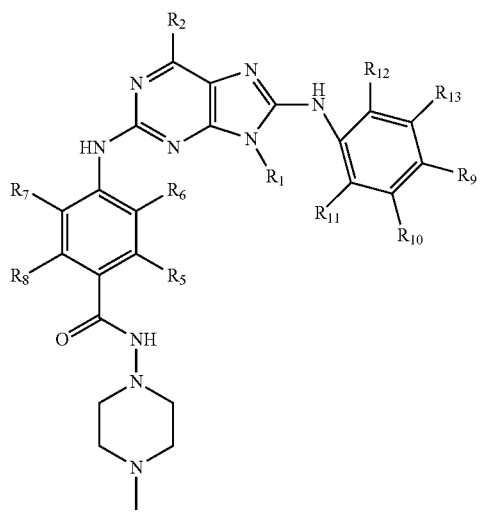

III $R_1$ represents —H, —C$_m$H$_{(2m+1)}$, —C$_6$H$_5$, —C$_m$H$_{(2m+1)}$ substituted by C$_3$-C$_7$cycloalkyl, C$_3$-C$_7$cycloalkyl, or C$_3$-C$_2$cycloalkyl substituted by —C$_m$H$_{(2m+1)}$;

$R_2$ represents —H, —NH$_2$, —OH, —F, —Cl, —Br, —CF$_3$, —C$_m$H$_{(2m+1)}$, —OC$_m$H$_{(2m+1)}$, —NHC$_m$H$_{(2m+1)}$, aryloxy containing 6-12 carbon atoms, or arylamino containing 6-12 carbon atoms.

$R_5$-$R_8$ respectively represent —H, —F, —Cl, —Br, —CF$_3$, —OCF$_3$, —OC$_m$H$_{(2m+1)}$,

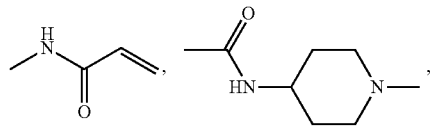

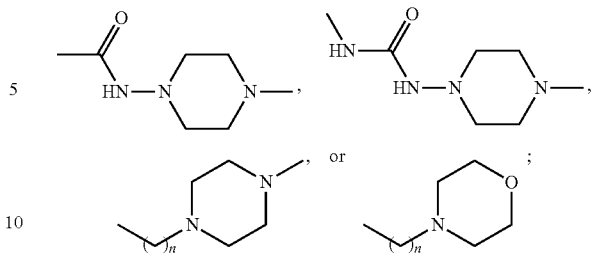

$R_9$-$R_{13}$ respectively represent —H, —F, —Cl, —Br, —CF$_3$, —OCF$_3$, —CN, —C$_m$H$_{(2m+1)}$, —OC$_m$H$_{(2m+1)}$,

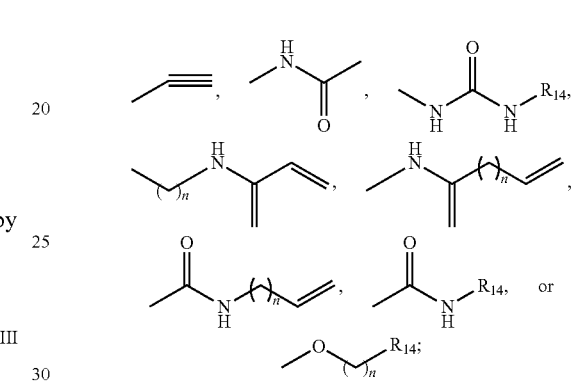

$R_{14}$ represents aryl or heteroaryl containing 6-10 carbon atoms; said heteroaryl contains 1-3 heteroatoms selected from N, O and S;

m=1-8; and n=0-4.

Preferably, the arylamino purine derivative is represented by formula (III), wherein $R_1$ represents —H, —C$_m$H$_{(2m+1)}$, C$_3$-C$_7$cycloalkyl, or C$_3$-C$_7$cycloalkyl substituted by —C$_m$H$_{(2m+1)}$;

$R_2$ represents —H, —NH$_2$, —OH, —F, —Cl, —Br, —CF$_3$, —C$_m$H$_{(2m+1)}$, —OC$_m$H$_{(2m+1)}$, or —NHC$_m$H$_{(2m+1)}$;

$R_5$-$R_8$ respectively represent —H, —F, —Cl, —Br, —CF$_3$, —OCF$_3$, —OC$_m$H$_{(2m+1)}$,

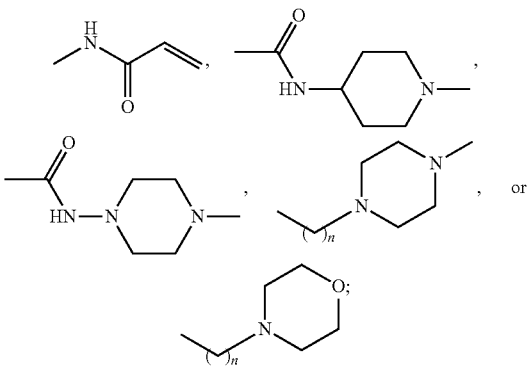

$R_9$-$R_{13}$ respectively represent —H, —F, —Cl, —Br, —CF$_3$, —OCF$_3$, —CN, —C$_m$H$_{(2m+1)}$, —OC$_m$H$_{(2m+1)}$,

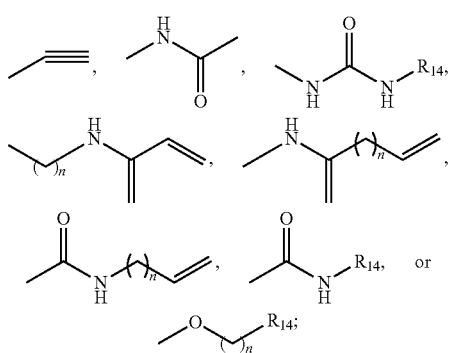

R$_{14}$ represents aryl or heteroaryl containing 6-10 carbon atoms; said heteroaryl contains 1-3 heteroatoms selected from N, O and S; m=1-8; and
n=0-4.

Preferably, the arylamino purine derivative is represented by formula (III), wherein
R$_1$ represents —H, —C$_m$H$_{(2m+1)}$, or C$_3$-C$_7$cycloalkyl;
R$_2$ represents —H, —F, —Cl, —Br, —CF$_3$, —C$_m$H$_{(2m+1)}$, —OC$_m$H$_{(2m+1)}$, or —NHC$_m$H$_{(2m+1)}$;
R$_5$-R$_8$ respectively represent —H, —F, —Cl, —Br, —CF$_3$, or —OC$_m$H$_{(2m+1)}$;
R$_9$-R$_{13}$ respectively represent —H, —F, —Cl, —Br, —CF$_3$, —CN, —C$_m$H$_{(2m+1)}$, —OC$_m$H$_{(2m+1)}$,

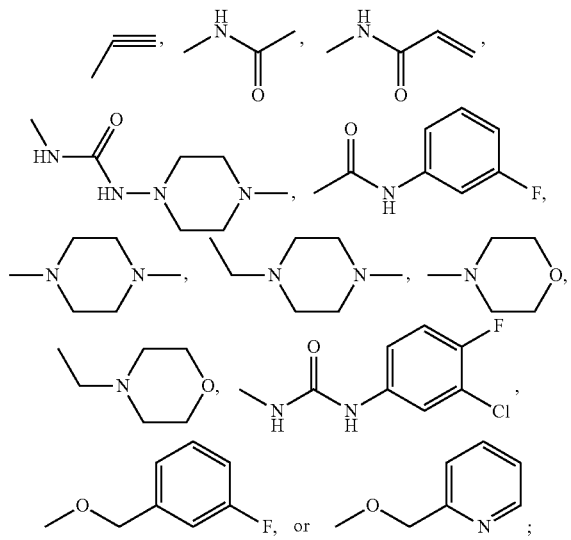

m=1-8.

Preferably, the arylamino purine derivative is represented by formula (III), wherein
R$_1$ represents —H, —C$_m$H$_{(2m+1)}$,

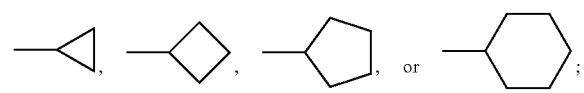

R$_2$ represents —H, —C$_m$H$_{(2m+1)}$, —C$_m$H$_{(2m+1)}$, or —NH-C$_m$H$_{(2m+1)}$;
R$_5$-R$_8$ respectively represent —H, —F, —Cl, —Br, —CF$_3$, —OCF$_3$, or —OC$_m$H$_{(2m+1)}$;
R$_9$-R$_{13}$ respectively represent —H, —F, —Cl, —Br, —CF$_3$, —OCF$_3$, —C$_m$H$_{(2m+1)}$, —OC$_m$H$_{(2m+1)}$,

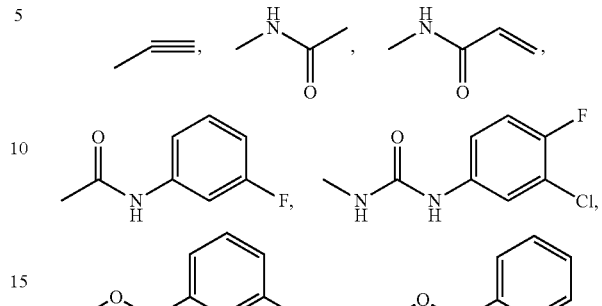

and
m=1-8.

Preferably, the arylamino purine derivative is represented by formula (III), wherein
R$_1$ represents —H, —C$_m$H$_{(2m+1)}$,

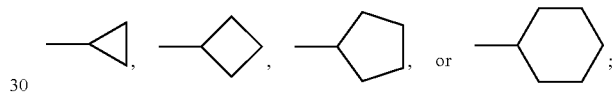

R$_2$ represents —H; R$_5$-R$_8$ respectively represent —H, —F, —Cl, —Br, —CF$_3$, or —OC$_m$H$_{(2m+1)}$;
R$_9$-R$_{13}$ respectively represent —H, —F, —Cl, —Br, —CF$_3$, —C$_m$H$_{(2m+1)}$, —OC$_m$H$_{(2m+1)}$,

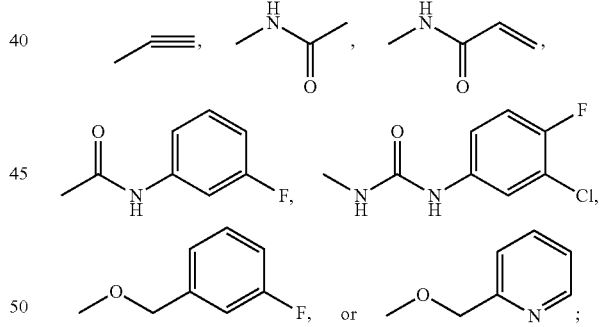

m=1-8.

Most preferably, the arylamino purine derivative is represented by formula (III), wherein
R$_1$ represents —H, —C$_m$H$_{(2m+1)}$,

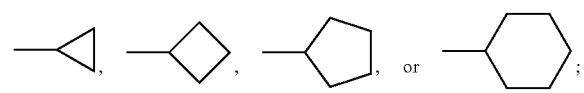

R$_2$ represents —H; R$_5$-R$_8$ represent —H;
R$_9$-R$_{13}$ respectively represent —H, —F, —Cl, —Br, —CF$_3$, —C$_m$H$_{(2m+1)}$, —OC$_m$H$_{(2m+1)}$,

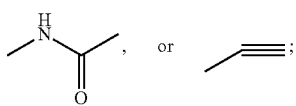

m=1-8.

Further, the arylamino purine derivative is represented by formula (IV), wherein

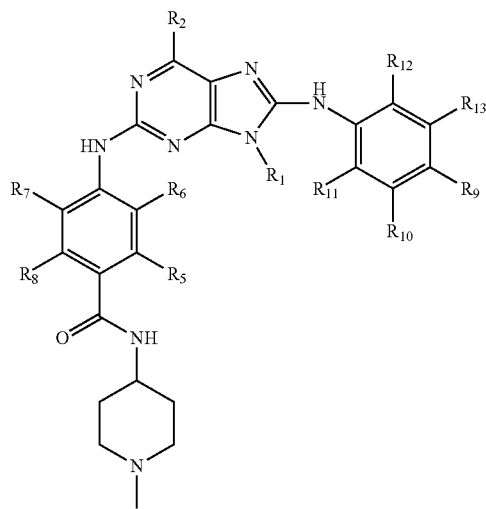

IV $R_1$ represents —H, —$C_{11}H_{(2m+1)}$, —$C_6H_5$, —$C_mH_{(2m+1)}$ substituted by $C_3$-$C_7$cycloalkyl, $C_3$-$C_7$cycloalkyl, or $C_3$-$C_2$cycloalkyl substituted by —$C_mH_{(2m+1)}$;

$R_2$ represents —H, —$NH_2$, —OH, —F, —Cl, —Br, —$CF_3$, —$C_mH_{(2m+1)}$, —$OC_mH_{(2m+1)}$, —$NHC_mH_{(2m+1)}$, aryloxy containing 6-12 carbon atoms, or arylamino containing 6-12 carbon atoms;

$R_5$-$R_8$ respectively represent —H, —F, —Cl, —Br, —$CF_3$, —$OCF_3$, —$OC_mH_{(2m+1)}$,

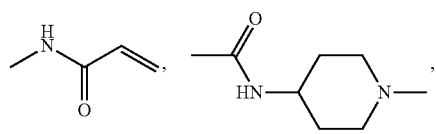

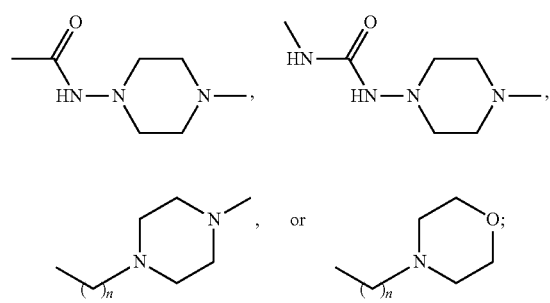

$R_9$-$R_{13}$ respectively represent —H, —F, —Cl, —Br, —$CF_3$, —$OCF_3$, —CN, —$C_mH_{(2m+1)}$, —$OC_mH_{(2m+1)}$,

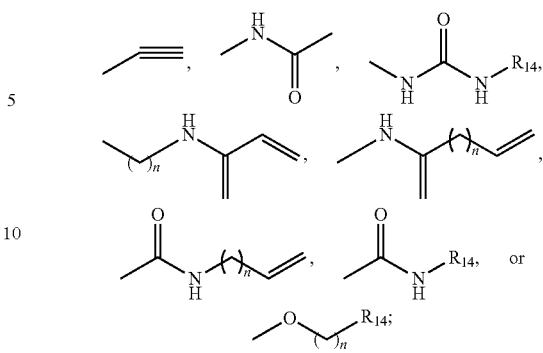

$R_{14}$ represents aryl or heteroaryl containing 6-10 carbon atoms; said heteroaryl contains 1-3 heteroatoms selected from N, O and S; m=1-8; and n=0-4.

Preferably, the arylamino purine derivative is represented by formula (IV), wherein $R_1$ represents —H, —$C_mH_{(2m+1)}$, —$C_mH_{(2m+1)}$ substituted by $C_3$-$C_7$cycloalkyl, $C_3$-$C_7$cycloalkyl, or $C_3$-$C_2$cycloalkyl substituted by —$C_mH_{(2m+1)}$;

$R_2$ represents —H, —$NH_2$, —OH, —F, —Cl, —Br, —$CF_3$, —$C_mH_{(2m+1)}$, —$OC_mH_{(2m+1)}$, or —$NHC_mH_{(2m+1)}$;

$R_5$-$R_8$ respectively represent —H, —F, —Cl, —Br, —$CF_3$, —$OCF_3$, —$OC_mH_{(2m+1)}$,

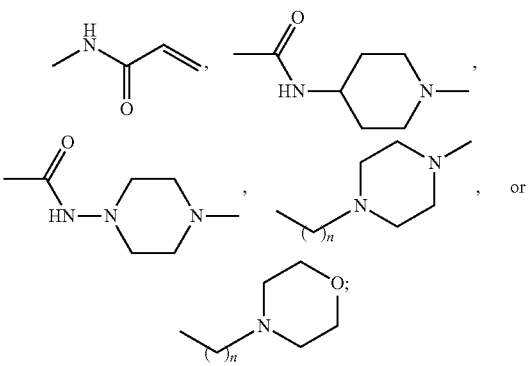

$R_9$-$R_{13}$ respectively represent —H, —F, —Cl, —Br, —$CF_3$, —$OCF_3$, —CN, —$C_mH_{(2m+1)}$, —$OC_mH_{(2m+1)}$,

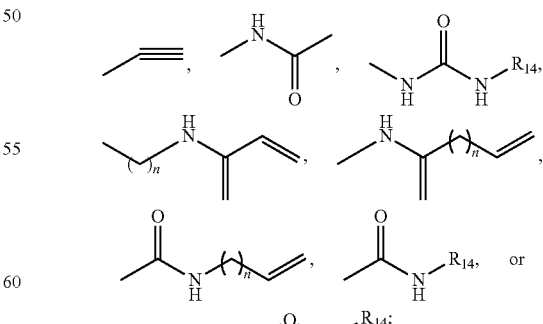

$R_{14}$ represents aryl or heteroaryl containing 6-10 carbon atoms; said heteroaryl contains 1-3 heteroatoms selected from N, O and S; m=1-8; and n=0-4.

Preferably, the arylamino purine derivative is represented by formula (IV), wherein $R_1$ represents —H, —$C_mH_{(2m+1)}$, $C_3$-$C_2$cycloalkyl, or $C_3$-$C_7$cycloalkyl substituted by —$C_mH_{(2m+1)}$;

$R_2$ represents —H, —F, —Cl, —Br, —$CF_3$, —$C_mH_{(2m+1)}$, —$OC_mH_{(2m+1)}$, or —$NHC_mH_{(2m+1)}$;

$R_5$-$R_8$ respectively represent —H, —F, —Cl, —Br, —$CF_3$, —$OCF_3$, —$OC_mH_{(2m+1)}$,

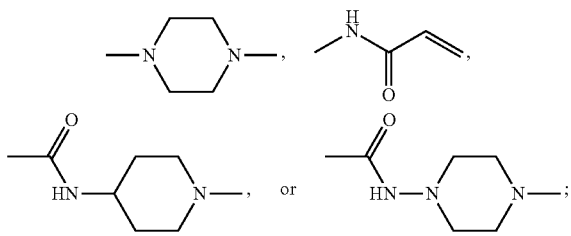

$R_9$-$R_{13}$ respectively represent —H, —F, —Cl, —Br, —$CF_3$, —CN, —$C_mH_{(2m+1)}$, —$OC_mH_{(2m+1)}$,

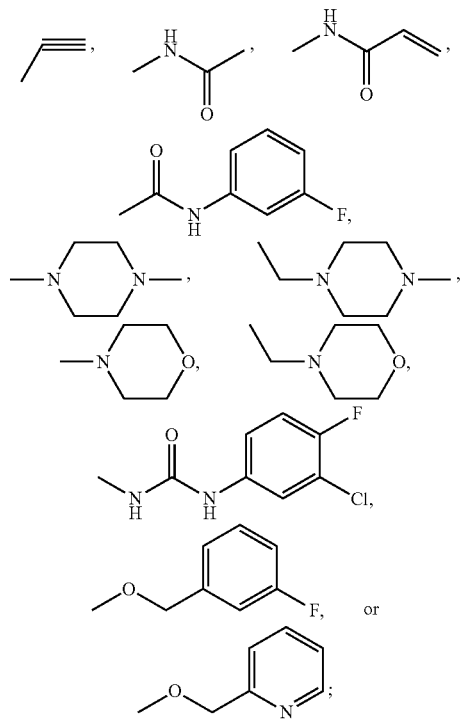

and
m=1-8.

Preferably, the arylamino purine derivative is represented by formula (IV), wherein $R_1$ represents —H, —$C_mH_{(2m+1)}$, or $C_3$-$C_7$cycloalkyl;

$R_2$ represents —H, —F, —Cl, —Br, —$C_mH_{(2m+1)}$, —$OC_mH_{(2m+1)}$, or —$NHC_mH_{(2m+1)}$;

$R_5$-$R_8$ respectively represent —H, —F, —Cl, —Br, —$CF_3$, —$OCF_3$, or —$OC_mH_{(2m+1)}$;

$R_9$-$R_{13}$ respectively represent —H, —F, —Cl, —Br, $CF_3$, —$C_mH_{(2m+1)}$, —$OC_mH_{(2m+1)}$,

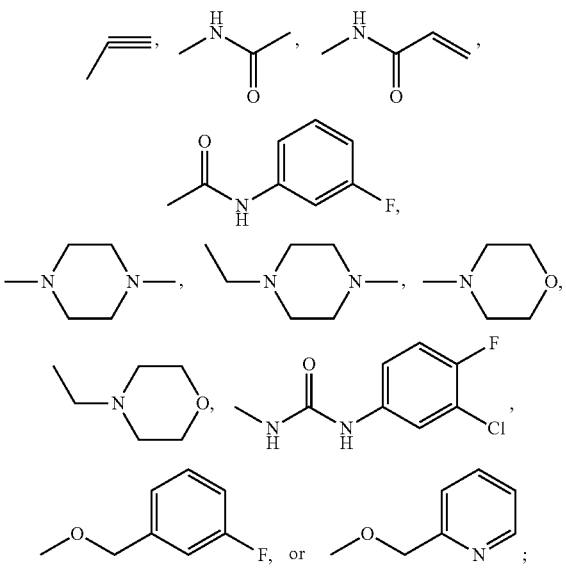

and
m=1-8.

Preferably, the arylamino purine derivative is represented by formula (IV), wherein $R_1$ represents —H, —$C_mH_{(2m+1)}$,

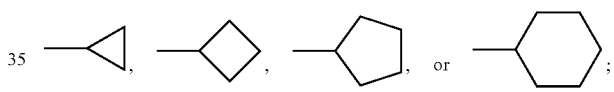

$R_2$ represents —H, —$C_mH_{(2m+1)}$, —$OC_mH_{(2m+1)}$, —$NHC_mH_{(2m+1)}$;

$R_5$-$R_8$ respectively represent —H, —F, —Cl, —Br, —$CF_3$, —$OCF_3$, or —$C_mH_{(2m+1)}$;

$R_9$-$R_{13}$ respectively represent —H, —F, —Cl, —Br, —$CF_3$, —$OCF_3$, —$C_mH_{(2m+1)}$, —$OC_mH_{(2m+1)}$,

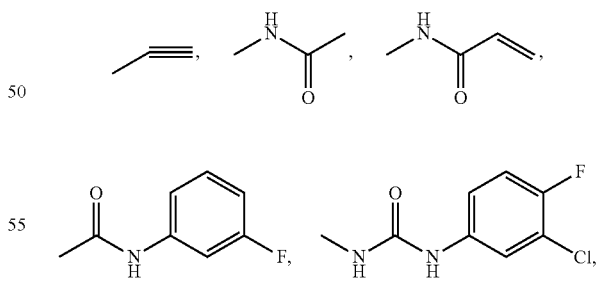

and
m=1-8.

Preferably, the arylamino purine derivative is represented by formula (IV), wherein $R_1$ represents —H, —$C_mH_{(2m+1)}$,

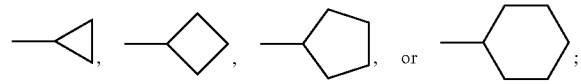

$R_2$ represents —H;

$R_5$-$R_8$ respectively represent —H, —F, —Cl, —Br, —$CF_3$, or —$OC_mH_{(2m+1)}$;

$R_9$-$R_{13}$ respectively represent —H, —F, —Cl, —Br, —$CF_3$, —$C_mH_{(2m+1)}$, —$OC_mH_{(2m+1)}$,

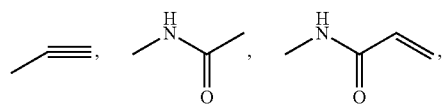

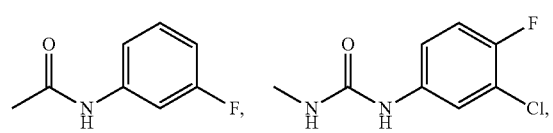

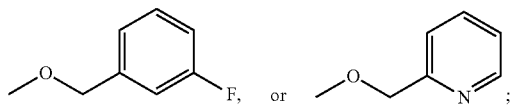

and
m=1-8.

Most preferably, the arylamino purine derivative is represented by formula (IV), wherein $R_1$ represents —H, —$C_mH_{(2m+1)}$,

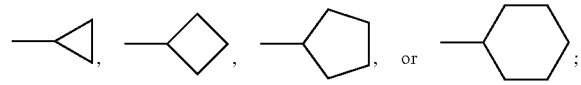

$R_2$ represents —H;
$R_5$-$R_8$ represent H;
$R_9$-$R_{13}$ respectively represent —H, —F, —Cl, —Br, —$CF_3$, —$C_mH_{(2m+1)}$, —$OC_mH_{(2m+1)}$, or

m=1-8.

Further, the arylamino purine derivative is represented by formula (V), wherein

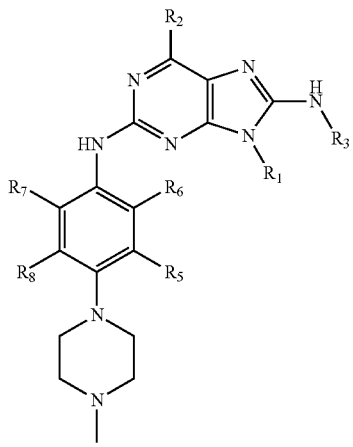

V $R_1$ represents —H, —$C_mH_{(2m+1)}$, —$C_6H_5$, $C_3$-$C_7$cycloalkyl, —$C_mH_{(2m+1)}$ substituted by $C_3$-$C_7$cycloalkyl, or $C_3$-$C_2$cycloalkyl substituted by —$C_mH_{(2m+1)}$;

$R_2$ represents —H, —$NH_2$, —OH, —F, —Cl, —Br, —$CF_3$, —$C_mH_{(2m+1)}$, —$OC_mH_{(2m+1)}$, —$NHC_mH_{(2m+1)}$, aryloxy containing 6-12 carbon atoms, or arylamino containing 6-12 carbon atoms;

$R_3$ represents $C_3$-$C_7$cycloalkyl, $C_3$-$C_7$cycloalkyl substituted by —$C_mH_{(2m+1)}$, aryl containing 6-80 carbon atoms or heteroaryl containing 6-80 carbon atoms; said heteroaryl contains 1-15 heteroatoms selected from N, O and S;

$R_5$-$R_8$ respectively represent —H, —F, —Cl, —Br, —$CF_3$, —$OCF_3$, —$OC_mH_{(2m+1)}$,

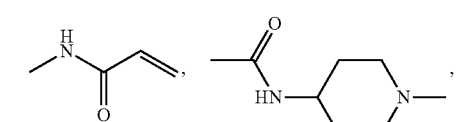

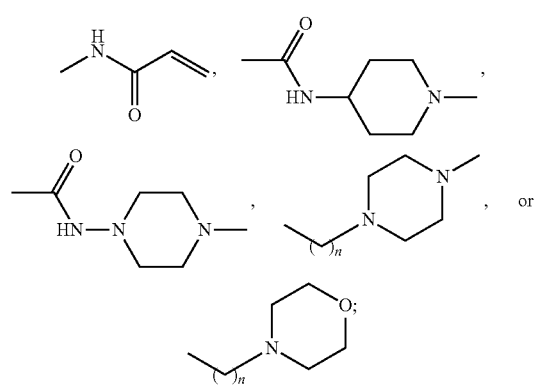

m=1-8; and
n=0-4.

Preferably, the arylamino purine derivative is represented by formula (V), wherein $R_1$ represents —H, —$C_mH_{(2m+1)}$, $C_3$-$C_7$cycloalkyl, —$C_mH_{(2m+1)}$ substituted by $C_3$-$C_7$cycloalkyl, or $C_3$-$C_2$cycloalkyl substituted by —$C_mH_{(2m+1)}$;

$R_2$ represents —H, —$NH_2$, —OH, —F, —Cl, —Br, —$CF_3$, —$C_mH_{(2m+1)}$, —$OC_mH_{(2m+1)}$, or —$NHC_mH_{(2m+1)}$;

$R_3$ represents

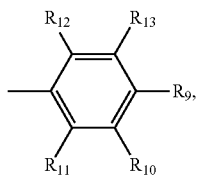

pyrimidinyl, halopyrimidinyl, $C_3$-$C_7$cycloalkyl, or $C_3$-$C_2$cycloalkyl substituted by —$C_mH_{(2m+1)}$;

$R_5$-$R_8$ respectively represent —H, —F, —Cl, —Br, —$CF_3$, —$OCF_3$, —$OC_mH_{(2m+1)}$,

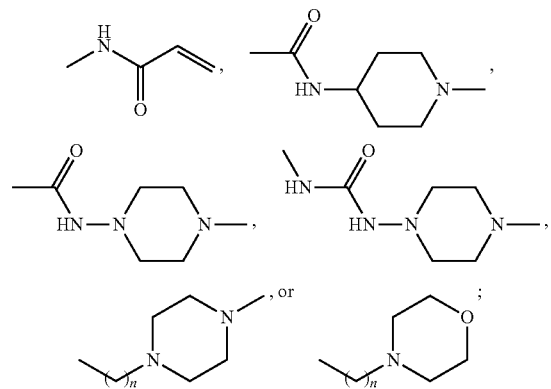

$R_9$-$R_{13}$ respectively represent —H, —F, —Cl, —Br, —$CF_3$, —$OCF_3$, —CN, —$C_mH_{(2m+1)}$, —$OC_mH_{(2m+1)}$,

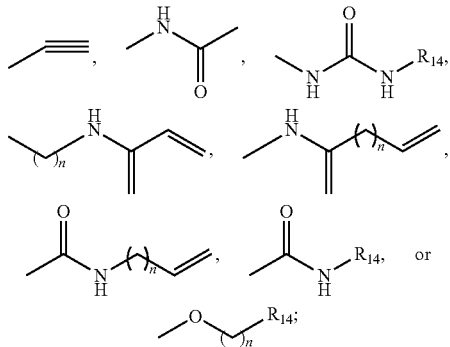

$R_{14}$ represents aryl or heteroaryl containing 6-10 carbon atoms; said heteroaryl contains 1-3 heteroatoms selected from N, O and S; m=1-8; and n=0-4.

Preferably, the arylamino purine derivative is represented by formula (V), wherein $R_1$ represents —H, —$C_mH_{(2m+1)}$, $C_3$-$C_7$cycloalkyl, —$C_mH_{(2m+1)}$ substituted by $C_3$-$C_7$cycloalkyl, or $C_3$-$C_7$cycloalkyl substituted by —$C_mH_{(2m+1)}$;

$R_2$ represents —H, —F, —Cl, —Br, —$CF_3$, —$C_mH_{(2m+1)}$, —$OC_mH_{(2m+1)}$, or —$NHC_mH_{(2m+1)}$;

$R_3$ represents

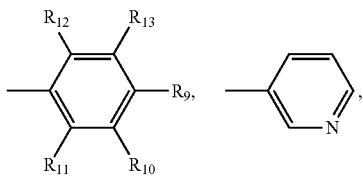

halopyrimidin-3-yl, $C_3$-$C_7$cycloalkyl, or $C_3$-$C_7$cycloalkyl substituted by —$C_mH_{(2m+1)}$;

$R_5$-$R_8$ respectively represent —H, —F, —Cl, —Br, —$CF_3$, —$OCF_3$, —$OC_mH_{(2m+1)}$,

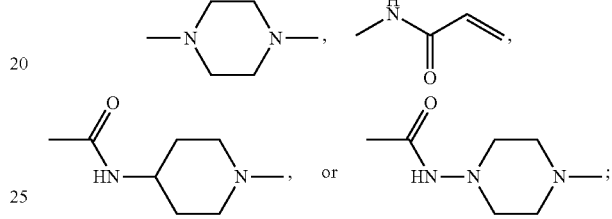

$R_9$-$R_{13}$ respectively represent —H, —F, —Cl, —Br, —$CF_3$, —CN, —$C_mH_{(2m+1)}$, —$OC_mH_{(2m+1)}$,

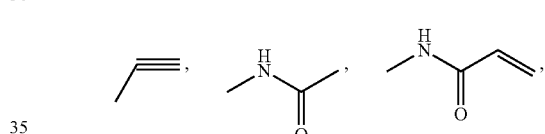

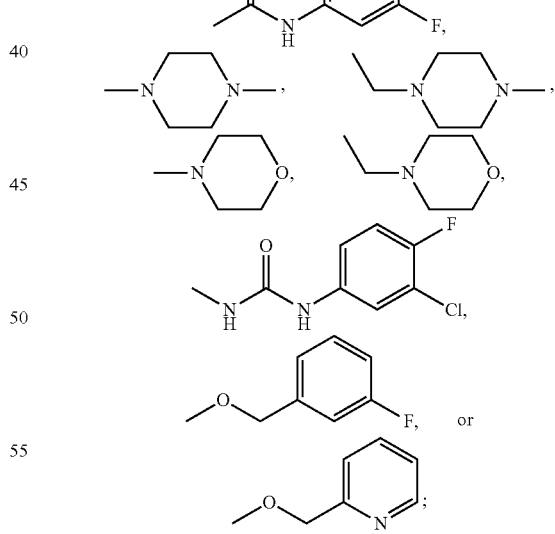

and m=1-8.

Preferably, the arylamino purine derivative is represented by formula (V), wherein $R_1$ represents —H, —$C_mH_{(2m+1)}$, —$C_mH_{(2m+1)}$ substituted by $C_3$-$C_7$cycloalkyl, or $C_3$-$C_7$cycloalkyl;

$R_2$ represents —H, —F, —Cl, —Br, —$C_mH_{(2m+1)}$, —$OC_mH_{(2m+1)}$, or —$NHC_mH_{(2m+1)}$;

$R_3$ represents

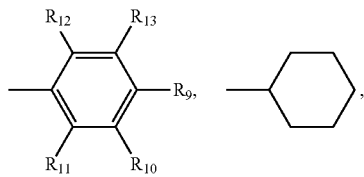

halopyrimidin-3-yl, or

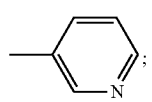;

$R_5$-$R_8$ respectively represent —H, —F, —Cl, —Br, —CF$_3$, or —OC$_m$H$_{(2m+1)}$;

$R_9$-$R_{13}$ respectively represent —H, —F, —Cl, —Br, —CF$_3$, —C$_m$F$_{(2m+1)}$, —OC$_m$H$_{(2m+1)}$,

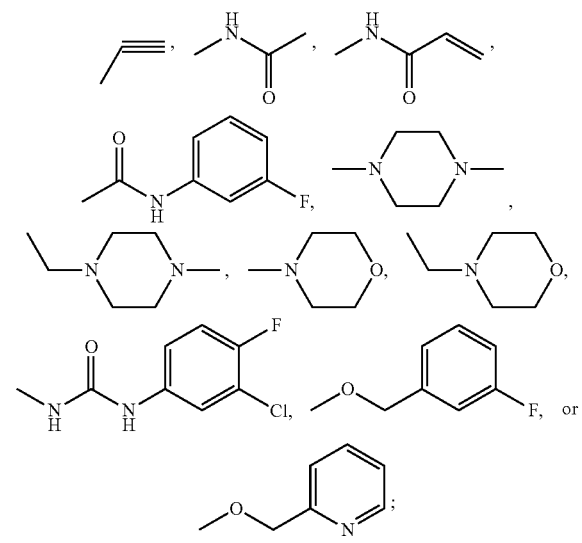

and
m=1-8.

Preferably, the arylamino purine derivative is represented by formula (V), wherein
$R_1$ represents —H, —C$_m$H$_{(2m+1)}$,

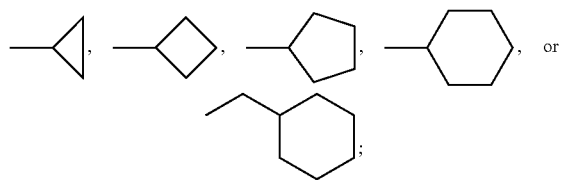

$R_2$ represents —H, —C$_m$H$_{(2m+1)}$, —OC$_m$H$_{(2m+1)}$, —NHC$_m$H$_{(2m+1)}$;

$R_3$ represents

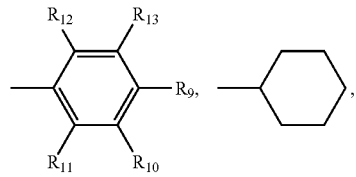

halopyrimidin-3-yl, or

;

$R_5$-$R_8$ respectively represent —H, —F, —Cl, —Br, —CF$_3$, or —OC$_m$H$_{(2m+1)}$;

$R_9$-$R_{13}$ respectively represent —H, —F, —Cl, —Br, —CF$_3$, —C$_m$Fl$_{(2m+1)}$, —OC$_m$H$_{(2m+1)}$,

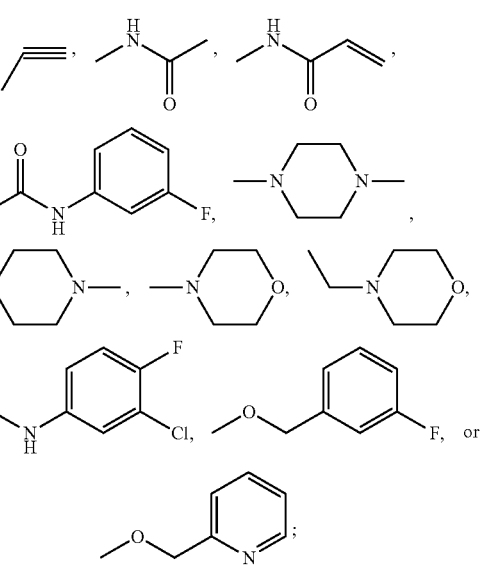

and
m=1-8.

Preferably, the arylamino purine derivative is represented by formula (V), wherein
$R_1$ represents —H, —C$_m$H$_{(2m+1)}$,

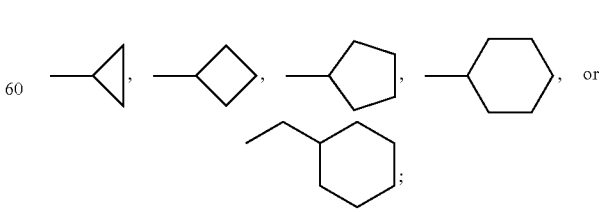

$R_2$ represents -H;

$R_3$ represents

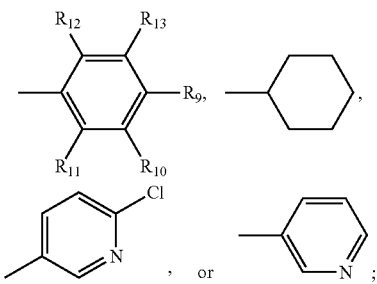

$R_5$-$R_8$ respectively represent —H, —F, —Cl, —Br, —CF$_3$, or —OC$_m$H$_{(2m+1)}$;
$R_9$-$R_{13}$ respectively represent —H, —F, —Cl, —Br, —CF$_3$, —OCF$_3$, —C$_m$H$_{(2m+1)}$, —OC$_m$H$_{(2m+1)}$,

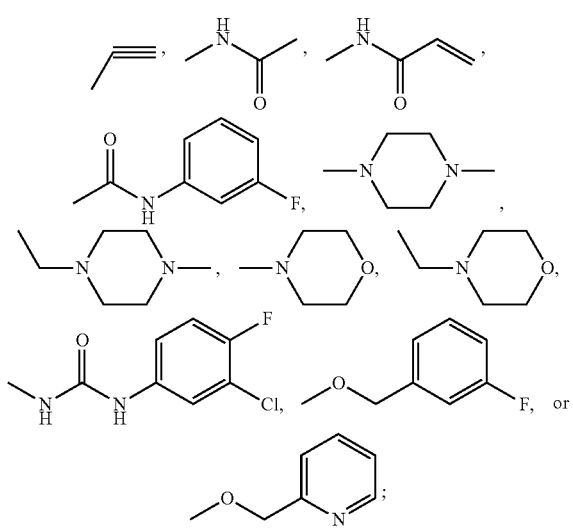

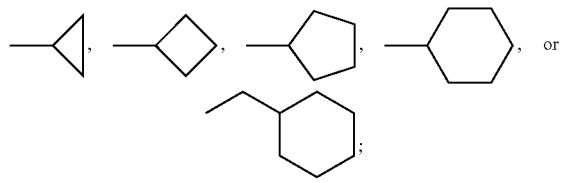

and
m=1-8.

Most preferably, $R_1$ represents —H, —C$_m$H$_{(2m+1)}$,

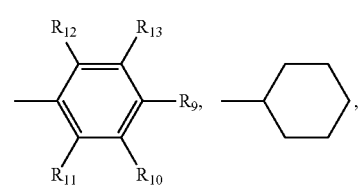

$R_2$ represents —H;
$R_3$ represents

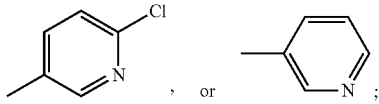

$R_5$-$R_8$ represent —H;
$R_9$-$R_{13}$ respectively represent —H, —F, —Cl, —Br, —CF$_3$, —OC$_m$H$_{(2m+1)}$,

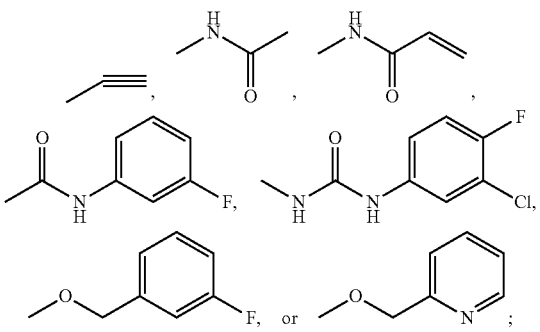

and
m=1-8.

Further, the arylamino purine derivative is represented by formula (VI), wherein

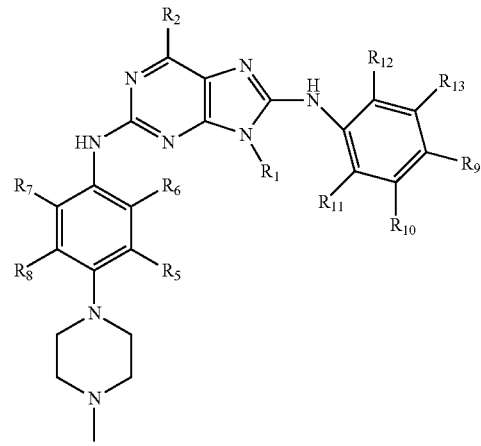

$R_1$ represents —H, —C$_m$H$_{(2m+1)}$, —C$_6$H$_5$, C$_3$-C$_7$cycloalkyl, —C$_m$H$_{(2m+1)}$ substituted by C$_3$-C$_7$cycloalkyl, or C$_3$-C$_2$cycloalkyl substituted by —C$_m$H$_{(2m+1)}$;
$R_2$ represents —H, —NH$_2$, —OH, —F, —Cl, —Br, —CF$_3$, —C$_m$H$_{(2m+1)}$, —OC$_m$H$_{(2m+1)}$, —NHC$_m$H$_{(2m+1)}$, aryloxy containing 6-12 carbon atoms, or arylamino containing 6-12 carbon atoms;
$R_5$-$R_8$ respectively represent —H, —F, —Cl, —Br, —CF$_3$, —OCF$_3$, —OC$_m$H$_{(2m+1)}$,

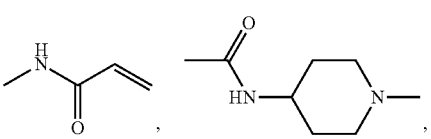

-continued

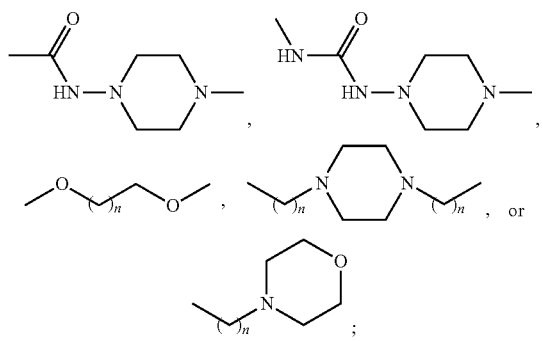

$R_9$-$R_{13}$ respectively represent —H, —F, —Cl, —Br, —CF$_3$, —OCF$_3$, —CN, —C$_m$H$_{(2m+1)}$, —OC$_m$H$_{(2m+1)}$,

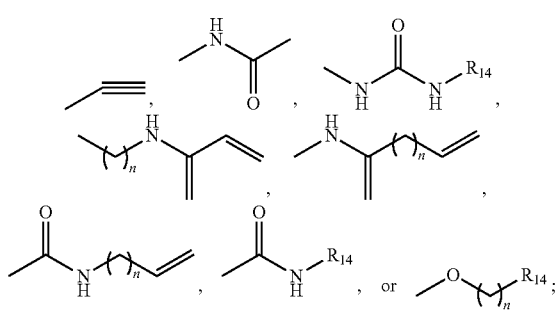

$R_{14}$ represents aryl or heteroaryl containing 6-10 carbon atoms; said heteroaryl contains 1-3 heteroatoms selected from N, O and S; m=1-8; and
n=0-4.

Preferably, the arylamino purine derivative is represented by formula (VI), wherein $R_1$ represents —H, —C$_m$H$_{(2m+1)}$, C$_3$-C$_7$cycloalkyl, —C$_m$H$_{(2m+1)}$ substituted by C$_3$-C$_7$cycloalkyl, or C$_3$-C$_2$cycloalkyl substituted by —C$_m$H$_{(2m+1)}$;

$R_2$ represents —H, —NH$_2$, —OH, —F, —Cl, —Br, —CF$_3$, —C$_m$H$_{(2m+1)}$, —OC$_m$H$_{(2m+1)}$, or —NHC$_m$H$_{(2m+1)}$;

$R_5$-$R_8$ respectively represent —H, —F, —Cl, —Br, —CF$_3$, —OCF$_3$, —OC$_m$H$_{(2m+1)}$,

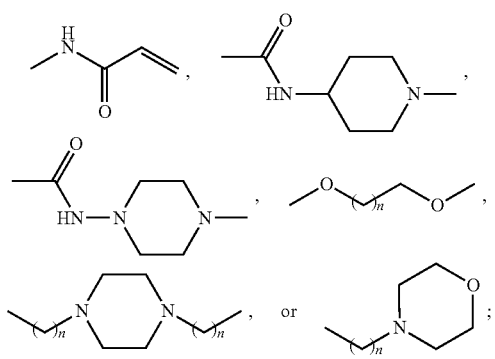

$R_9$-$R_{13}$ respectively represent —H, —F, —Cl, —Br, —CF$_3$, —OCF$_3$, —CN, —C$_m$H$_{(2m+1)}$,

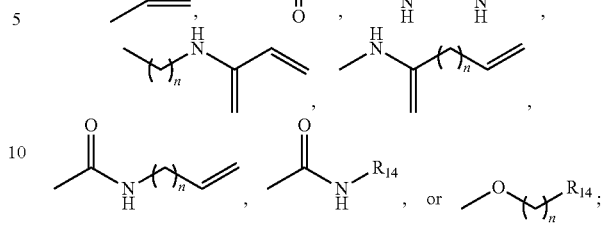

$R_{14}$ represents aryl or heteroaryl containing 6-10 carbon atoms; said heteroaryl contains 1-3 heteroatoms selected from N, O and S; m=1-8; and
n=0-4.

Preferably, the arylamino purine derivative is represented by formula (VI), wherein $R_1$ represents —H, —C$_m$H$_{(2m+1)}$, C$_3$-C$_7$cycloalkyl, —C$_m$H$_{(2m+1)}$ substituted by C$_3$-C$_7$cycloalkyl, or C$_3$-C$_7$cycloalkyl substituted by —C$_m$H$_{(2m+1)}$;

$R_2$ represents —H, —F, —Cl, —Br, —CF$_3$, —C$_m$H$_{(2m+1)}$, —C$_m$H$_{(2m+1)}$, or —NHC$_m$H$_{(2m+1)}$;

$R_5$-$R_8$ respectively represent —H, —F, —Cl, —Br, —CF$_3$, —OCF$_3$, —OC$_m$H$_{(2m+1)}$,

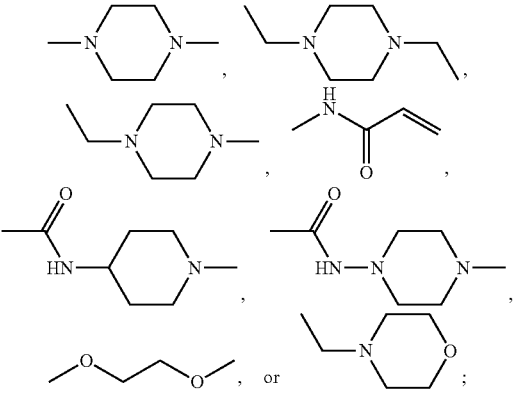

$R_9$-$R_{13}$ respectively represent —H, —F, —Cl, —Br, —CF$_3$, —OCF$_3$, —CN, —C$_m$H$_{(2m+1)}$, —OC$_m$H$_{(2m+1)}$,

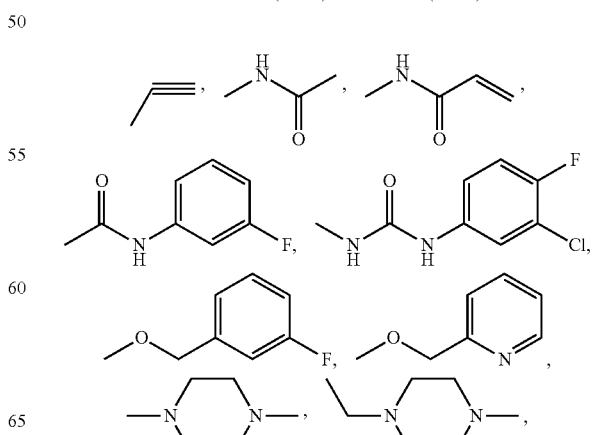

-continued

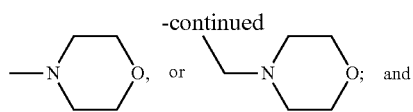

m=1-8.

Preferably, the arylamino purine derivative is represented by formula (VI), wherein
$R_1$ represents —H, —$C_mH_{(2m+1)}$, —$C_mH_{(2m+1)}$ substituted by $C_3$-$C_7$cycloalkyl, or $C_3$-$C_7$cycloalkyl;
$R_2$ represents —H, —F, —Cl, —Br, —$C_mH_{(2m+1)}$, —$OC_mH_{(2m+1)}$, or —$NHC_mH_{(2m+1)}$;
$R_5$-$R_8$ respectively represent —H, —F, —Cl, —Br, —$CF_3$, —$OCF_3$, or —$OC_mH_{(2m+1)}$;
$R_9$-$R_{13}$ respectively represent —H, —F, —Cl, —Br, —$CF_3$, —$OCF_3$, —$C_mH_{(2m+1)}$, —$OC_mH_{(2m+1)}$,

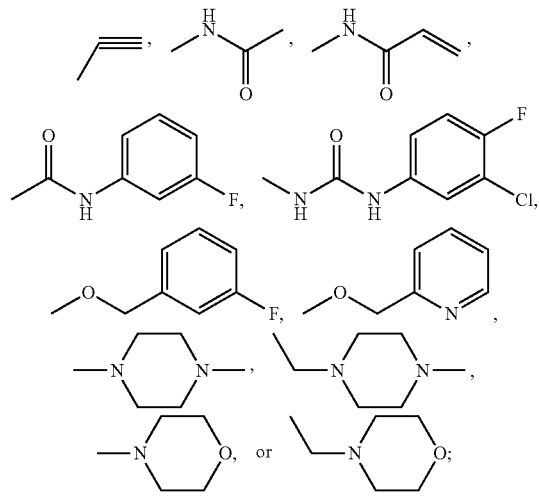

and
m=1-8.

Preferably, the arylamino purine derivative is represented by formula (VI), wherein
$R_1$ represents —H, —$C_mH_{(2m+1)}$,

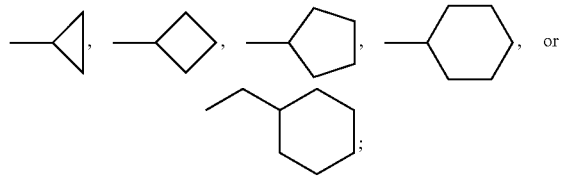

$R_2$ represents —H, —$C_mH_{(2m+1)}$, —$OC_mH_{(2m+1)}$, —$NHC_mH_{(2m+1)}$;
$R_5$-$R_8$ respectively represent —H, —F, —Cl, —Br, —$CF_3$, —$OCF_3$, or —$OC_mH_{(2m+1)}$;
$R_9$-$R_{13}$ respectively represent —H, —F, —Cl, —Br, —$CF_3$, —$OCF_3$, —$C_mH_{(2m+1)}$, —$OC_mH_{(2m+1)}$,

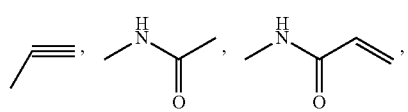

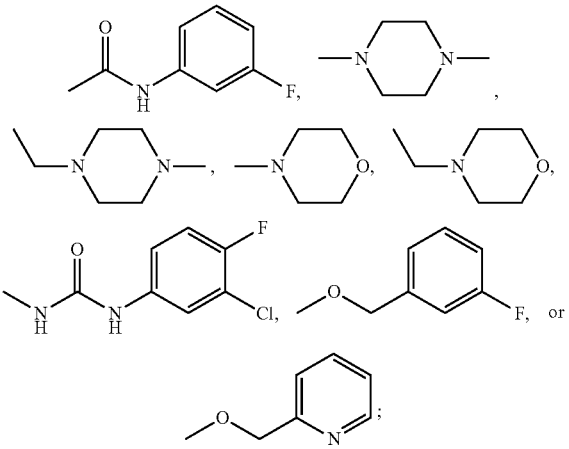

and
m=1-8.

Preferably, the arylamino purine derivative is represented by formula (VI), wherein
$R_1$ represents —H, —$C_mH_{(2m+1)}$,

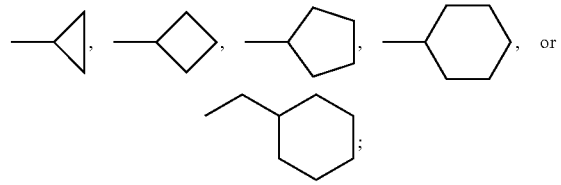

$R_2$ represents —H; $R_5$-$R_8$ respectively represent —H, —F, —Cl, —Br, —$CF_3$, or —$OC_mH_{(2m+1)}$;
$R_9$-$R_{13}$ respectively represent —H, —F, —Cl, —Br, —$CF_3$, —$OCF_3$, —$C_mH_{(2m+1)}$, —$OC_mH_{(2m+1)}$,

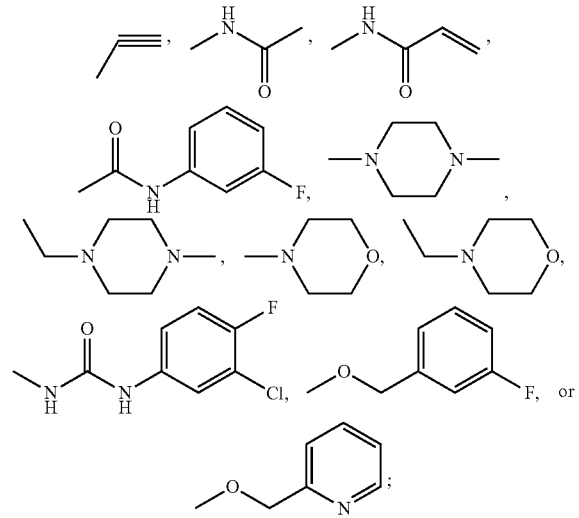

and
m=1-8.

Most preferably, the arylamino purine derivative is represented by formula (VI), wherein
$R_1$ represents —H, —$C_mH_{(2m+1)}$,

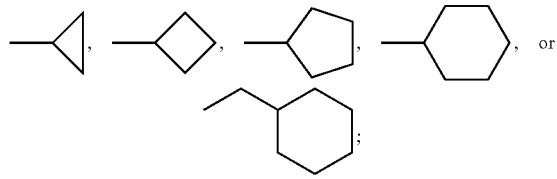, or

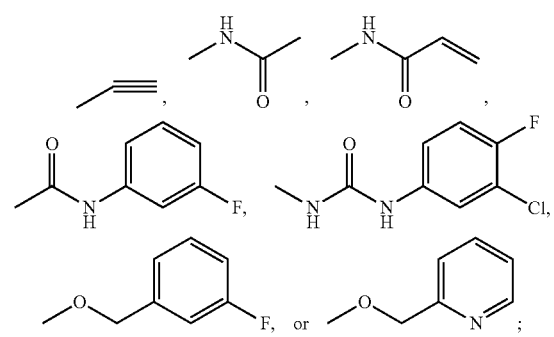;

$R_2$ represents —H; $R_5$-$R_8$ represent —H;
$R_9$-$R_{13}$ respectively represent —H, —F, —Cl, —Br, —CF$_3$, —OC$_m$H$_{(2m+1)}$,

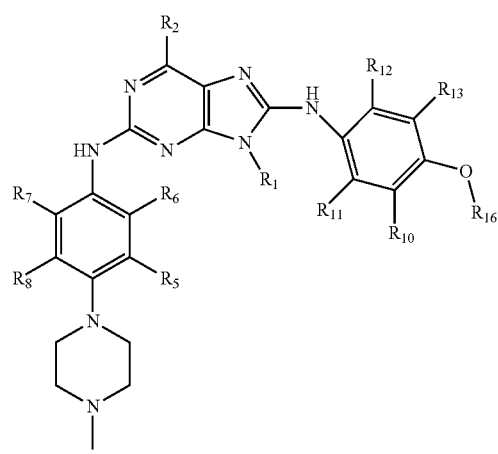;

and
m=1-8.

Preferably, the arylamino purine derivative is represented by formula (VII), wherein

VII

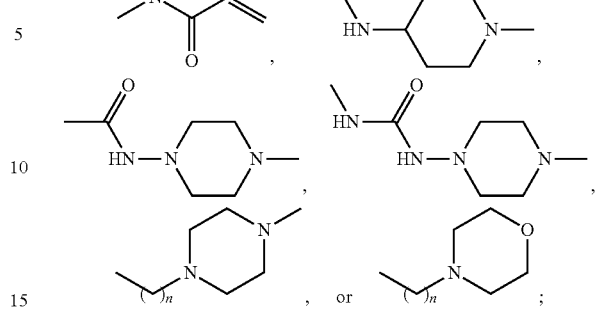

$R_1$ represents —H, —$C_mH_{(2m+1)}$, —$C_6H_5$, $C_3$-$C_7$cycloalkyl, —$C_mH_{(2m+1)}$ substituted by $C_3$-$C_7$cycloalkyl, or $C_3$-$C_7$cycloalkyl substituted by —$C_mH_{(2m+1)}$;
$R_2$ represents —H, —NH$_2$, —OH, —F, —Cl, —Br, —CF$_3$, —$C_mH_{(2m+1)}$, —OC$_mH_{(2m+1)}$, —NHC$_m$H$_{(2m+1)}$, aryloxy containing 6-12 carbon atoms, or arylamino containing 6-12 carbon atoms;
$R_5$-$R_8$ respectively represent —H, —F, —Cl, —Br, —CF$_3$, —OCF$_3$, —OC$_m$H$_{(2m+1)}$,

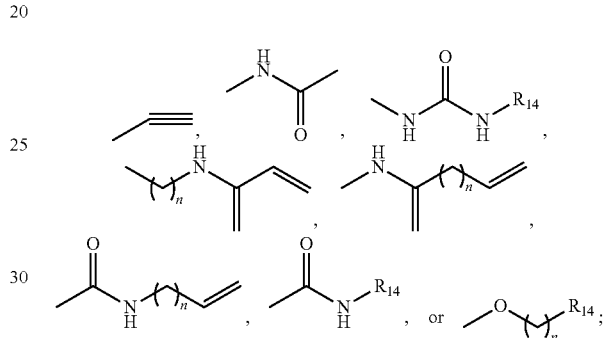

$R_{10}$-$R_{13}$ respectively represent —H, —F, —Cl, —Br, —CF$_3$, —OCF$_3$, —CN, —$C_mH_{(2m+1)}$, —OC$_m$H$_{(2m+1)}$,

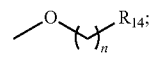

$R_{16}$ represents

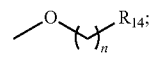

$R_{14}$ represents —$C_mH_{(2m+1)}$, aryl or heteroaryl containing 6-10 carbon atoms; said heteroaryl contains 1-3 heteroatoms selected from N, O and S; m=1-8; and
n=0-4.

Preferably, the arylamino purine derivative is represented by formula (VII), wherein
$R_1$ represents —H, —$C_mH_{(2m+1)}$, —$C_mH_{(2m+1)}$ substituted by $C_3$-$C_2$cycloalkyl, or $C_3$-$C_2$cycloalkyl;
$R_2$ represents —H, —NH$_2$, —OH, —F, —Cl, —Br, —CF$_3$, —$C_mH_{(2m+1)}$, —OC$_mH_{(2m+1)}$, or —NHC$_m$H$_{(2m+1)}$;
$R_5$-$R_8$ respectively represent —H, —F, —Cl, —Br, —CF$_3$, —OCF$_3$, —OC$_m$H$_{(2m+1)}$,

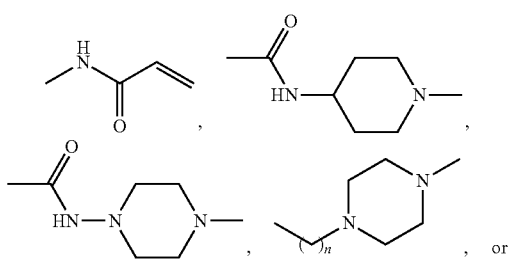

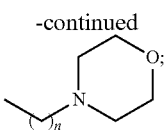

$R_{10}$-$R_{13}$ respectively represent —H, —F, —Cl, —Br, —CF$_3$, —OCF$_3$, —CN, —C$_m$H$_{(2m+1)}$, —OC$_m$H$_{(2m+1)}$,

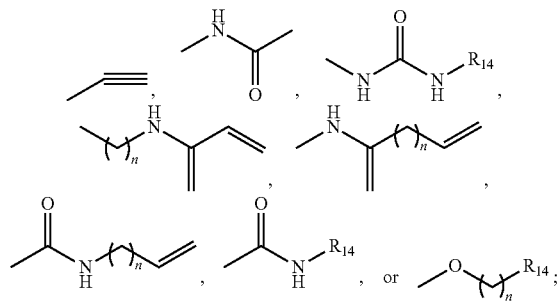

$R_{14}$ represents aryl or heteroaryl containing 6-10 carbon atoms; said heteroaryl contains 1-3 heteroatoms selected from N, O and S;
$R_{16}$ represents

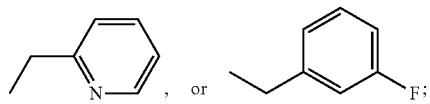

m=1-8; and
n=0-4.

Preferably, the arylamino purine derivative is represented by formula (VII), wherein
$R_1$ represents —H, —C$_m$H$_{(2m+1)}$, —C$_m$H$_{(2m+1)}$ substituted by C$_3$-C$_2$cycloalkyl, or C$_3$-C$_2$cycloalkyl;
$R_2$ represents —H, —F, —Cl, —Br, —CF$_3$, —C$_m$H$_{(2m+1)}$, —OC$_m$H$_{(2m+1)}$, or —NHC$_m$H$_{(2m+1)}$;
$R_5$-$R_8$ respectively represent —H, —F, —Cl, —Br, —CF$_3$, —OC$_m$H$_{(2m+1)}$,

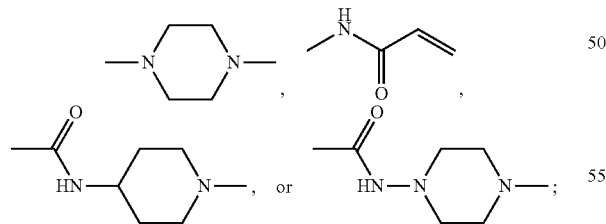

$R_{10}$-$R_{13}$ respectively represent —H, —F, —Cl, —Br, —CF$_3$, —OCF$_3$, —CN, —C$_m$H$_{(2m+1)}$, —OC$_m$H$_{(2m+1)}$,

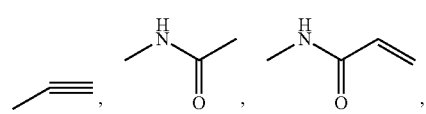

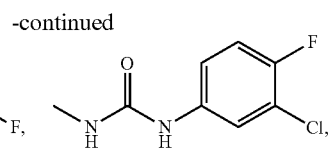

$R_{16}$ represents and

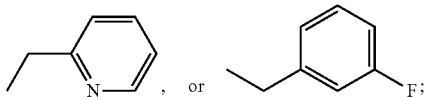

m=1-8.

Preferably, the arylamino purine derivative is represented by formula (VII), wherein
$R_1$ represents —H, —C$_m$H$_{(2m+1)}$, —C$_m$H$_{(2m+1)}$ substituted by C$_3$-C$_7$cycloalkyl, or C$_3$-C$_7$cycloalkyl;
$R_2$ represents —H, —C$_m$H$_{(2m+1)}$, —OC$_m$H$_{(2m+1)}$, or —NH-C$_m$H$_{(2m+1)}$;
$R_5$-$R_8$ respectively represent —H, —F, —Cl, —Br, —CF$_3$, —OCF$_3$, or —OC$_m$H$_{(2m+1)}$;
$R_{10}$-$R_{13}$ respectively represent —H, —F, —Cl, —Br, —CF$_3$, —OCF$_3$, —C$_m$H$_{(2m+1)}$, —OC$_m$H$_{(2m+1)}$,

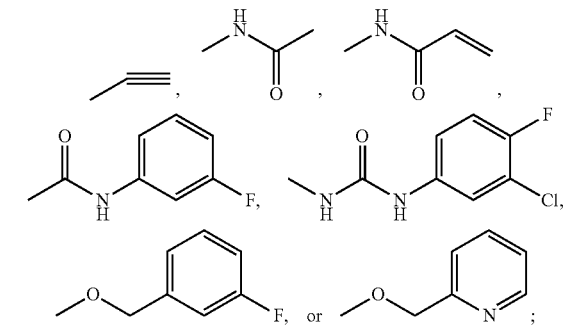

$R_{16}$ represents

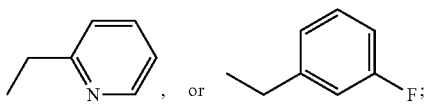

and
m=1-8.

Preferably, the arylamino purine derivative is represented by formula (VII), wherein
$R_1$ represents —H, —C$_m$H$_{(2m+1)}$, -continued

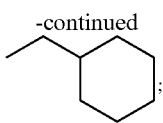
;

$R_2$ represents —H; $R_5$-$R_8$ respectively represent —H, —F, —Cl, —Br, —CF$_3$, —OCF$_3$, —C$_m$H$_{(2m+1)}$, or —OC$_m$H$_{(2m+1)}$;
$R_{10}$-$R_{13}$ respectively represent —H, —F, —Cl, —Br, —CF$_3$, —OCF$_3$, —C$_m$H$_{(2m+1)}$, —OC$_m$H$_{(2m+1)}$,

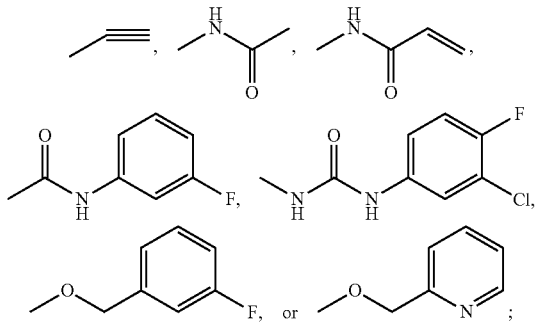

$R_{16}$ represents

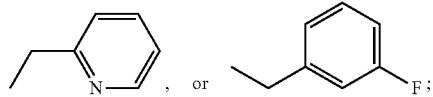
;

and
m=1-8.

Preferably, the arylamino purine derivative is represented by formula (VII), wherein
$R_1$ represents —H, —C$_m$H$_{(2m+1)}$,

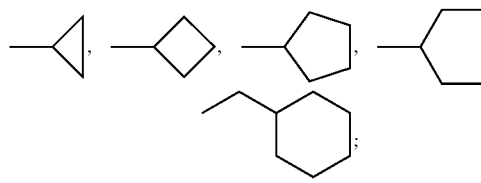
;

$R_2$ represents —H; $R_5$-$R_8$ respectively represent —H, —F, —Cl, —Br, —CF$_3$, —OCF$_3$, —C$_m$H$_{(2m+1)}$, or —OC$_m$H$_{(2m+1)}$;
$R_{10}$-$R_{13}$ respectively represent —H, —F, —Cl, —Br, —CF$_3$, —OCF$_3$, —C$_m$H$_{(2m+1)}$, or —OC$_m$H$_{(2m+1)}$;
$R_{16}$ represents

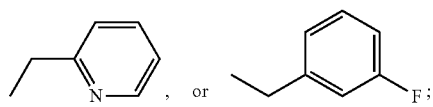
;

and
m=1-8.

Most preferably, the arylamino purine derivative is represented by formula (VII), wherein
$R_1$ represents —H, —C$_m$H$_{(2m+1)}$,

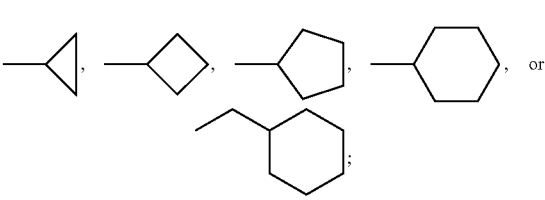
;

$R_2$ represents-H;
$R_5$-$R_8$ represent —H;
$R_{10}$-$R_{13}$ respectively represent —H, —F, —Cl, or —Br;
$R_{16}$ represents

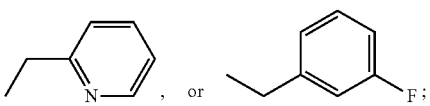
;

and
m=1-8.

Further, the arylamino purine derivative is represented by formula (VIII), wherein

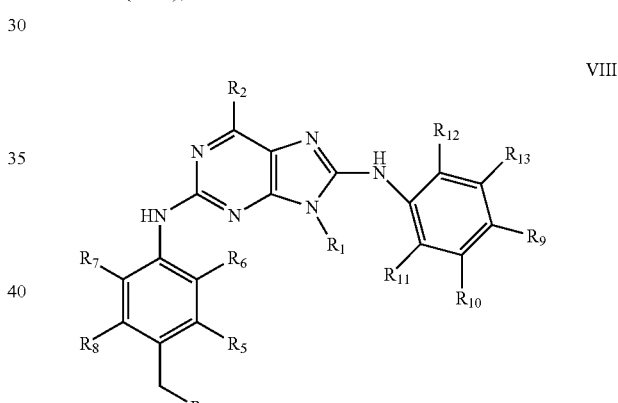

VIII $R_1$ represents —H, —C$_m$H$_{(2m+1)}$, C$_3$-C$_7$cycloalkyl, —C$_m$H$_{(2m+1)}$ substituted by C$_3$-C$_7$cycloalkyl, C$_3$-C$_7$cycloalkyl substituted by —C$_m$H$_{(2m+1)}$, heterocyclyl containing 3-8 carbon atoms, amino substituted by heterocyclyl containing 3-8 carbon atoms, aryl containing 6-8 carbon atoms, or heteroaryl containing 6-8 carbon atoms; said heteroaryl contains 1-3 heteroatoms selected from N, O and S;
$R_2$ represents —H, —NH$_2$, —OH, —F, —Cl, —Br, —CF$_3$, —C$_m$H$_{(2m+1)}$, —OC$_m$H$_{(2m+1)}$, —NHC$_m$H$_{(2m+1)}$, aryloxy containing 6-12 carbon atoms, or arylamino containing 6-12 carbon atoms;
$R_5$-$R_8$ respectively represent —H, —F, —Cl, —Br, —CF$_3$, —OCF$_3$, —OC$_m$H$_{(2m+1)}$,

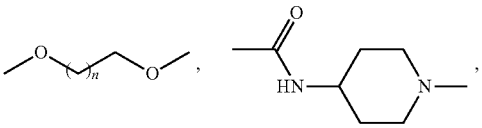
, $R_9$-$R_{13}$ respectively represent —H, —F, —Cl, —Br, —CF$_3$, —OCF$_3$, —CN, —C$_m$H$_{(2m+1)}$, —OC$_m$H$_{(2m+1)}$, or [alkynyl];

$R_{21}$ represents [morpholinyl], or [piperazinyl-alkyl];

m=1-8; and
n=0-4.

Preferably, the arylamino purine derivative is represented by formula (VIII), wherein
$R_1$ represents —H, —C$_m$H$_{(2m+1)}$, —C$_m$H$_{(2m+1)}$ substituted by C$_3$-C$_7$cycloalkyl, or C$_3$-C$_7$cycloalkyl;
$R_2$ represents —H, —C$_m$H$_{(2m+1)}$, —OC$_m$H$_{(2m+1)}$, or —NH-C$_m$H$_{(2m+1)}$;
$R_5$-$R_8$ respectively represent —H, —F, —Cl, —Br, —CF$_3$, —OCF$_3$, or —OC$_m$H$_{(2m+1)}$;
$R_9$-$R_{13}$ respectively represent —H, —F, —Cl, —Br, —CF$_3$, —C$_m$H$_{(2m+1)}$, or —OC$_m$H$_{(2m+1)}$;
$R_{21}$ represents [morpholinyl], or [piperazinyl-alkyl];

m=1-8; and
n=0-4.

Preferably, the arylamino purine derivative is represented by formula (VIII), wherein
$R_1$ represents —H, —C$_m$H$_{(2m+1)}$, [cyclopropyl], [cyclobutyl], [cyclopentyl], or [cyclohexyl];

$R_2$ represents —H; $R_5$-$R_8$ respectively represent —H, —F, —Cl, —Br, —CF$_3$, —C$_m$H$_{(2m+1)}$, or —OC$_m$H$_{(2m+1)}$;
$R_9$-$R_{13}$ respectively represent —H, —F, —Cl, —Br, —CF$_3$, —C$_m$H$_{(2m+1)}$, —OC$_m$H$_{(2m+1)}$;
$R_{21}$ represents [morpholinyl], or [piperazinyl-alkyl];

m=1-8; and
n=0-4.

Most preferably, the arylamino purine derivative is represented by formula (VIII), wherein
$R_1$ represents —H, —C$_m$H$_{(2m+1)}$, [cyclopropyl], [cyclobutyl], [cyclopentyl], or [cyclohexyl];

---

$R_9$-$R_{13}$ respectively represent —H, —F, —Cl, —Br, —CF$_3$, —OCF$_3$, —CN, —C$_m$H$_{(2m+1)}$, —OC$_m$H$_{(2m+1)}$,

[structures: alkynyl; acetamide; urea-R$_{14}$; enamine structures; acetamide-R$_{14}$; ether-R$_{14}$];

$R_{21}$ represents [morpholinyl], or [piperazinyl-alkyl];

$R_{14}$ represents aryl or heteroaryl containing 6-10 carbon atoms; said heteroaryl contains 1-3 heteroatoms selected from N, O and S; m=1-8; and
n=0-4.

Preferably, the arylamino purine derivative is represented by formula (VIII), wherein
$R_1$ represents —H, —C$_m$H$_{(2m+1)}$, —C$_m$H$_{(2m+1)}$ substituted by C$_3$-C$_7$cycloalkyl, or C$_3$-C$_7$cycloalkyl;
$R_2$ represents —H, —F, —Cl, —Br, —CF$_3$, —C$_m$H$_{(2m+1)}$, —OC$_m$H$_{(2m+1)}$, or —NHC$_m$H$_{(2m+1)}$;
$R_5$-$R_8$ respectively represent —H, —F, —Cl, —Br, —CF$_3$, —OCF$_3$, or —OC$_m$H$_{(2m+1)}$;

$R_2$ represents —H; $R_5$-$R_8$ represent —H; $R_9$-$R_{13}$ respectively represent —H, —F, —Cl, —Br, —CF$_3$, —C$_m$H$_{(2m+1)}$, or —OC$_m$H$_{(2m+1)}$;

$R_{21}$ represents

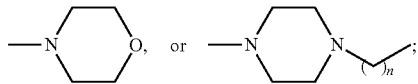

m=1-8, n=0-2.

Further, the arylamino purine derivative is represented by formula (IX), wherein

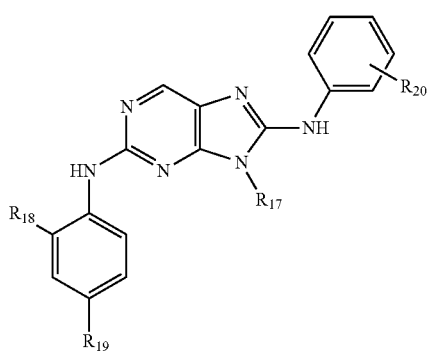

IX $R_{17}$ represents H, C$_{1-4}$alkyl, isopropyl, cyclopropyl, or cyclopentyl;

When $R_{18}$ represents H, $R_{19}$ represents 4-methylpiperazinyl-1-carbamoyl, 1-methylpiperidinyl-4-carbamoyl, 4-methyl piperazin-1-yl, 4-morpholinyl, 4-methylpiperazin-1-ylmethyl, 4-morpholinylmethyl, 3-(4-methylpiperazin-1-yl)ureido, or 3-(1-methylpiperidin-4-yl)ureido;

When $R_{18}$ represents fluoro, chloro, bromo, or methoxy, $R_{19}$ represents 4-methylpiperazinyl-1-carbamoyl, or 1-methylpiperidinyl-4-carbamoyl;

$R_{20}$ represents hydrogen, halogen, C$_{1-4}$alkyl, ethynyl, 3-chloro-4-(pyridin-2-yl)methoxy, or 3-chloro-4-(3-fluorophenyl)methoxy.

Preferably, $R_{17}$ represents H, C$_{1-4}$alkyl, isopropyl, cyclopropyl, or cyclopentyl;

When $R_{18}$ represents H, $R_{19}$ represents 4-methylpiperazinyl-1-carbamoyl, 1-methylpiperidinyl-4-carbamoyl, 4-methyl piperazin-1-yl, 4-morpholinyl, 4-methylpiperazin-1-ylmethyl, 4-morpholinylmethyl, 3-(4-methylpiperazin-1-yl)ureido, or 3-(1-methyl piperidin-4-yl)ureido;

When $R_{18}$ represents fluoro, chloro, bromo, or methoxy, $R_{19}$ represents 4-methylpiperazinyl-1-carbamoyl, or 1-methylpiperidinyl-4-carbamoyl;

$R_{20}$ represents hydrogen, halogen, C$_{1-4}$alkyl or ethynyl.

Further, the arylamino purine derivative is as below.

4-(9-isopropyl-8-phenylamino-9H-purin-2-ylamino)-N-(4-methylpiperidin-1-yl)benzamide,
4-(8-(3-chloro-4-fluorophenylamino)-9-isopropyl-9H-purin-2-ylamino)-N-(4-methylpiperidin-1-yl)benzamide,
4-(8-(3-acetamidophenylamino)-9-isopropyl-9H-purin-2-ylamino)-N-(4-methylpiperidin-1-yl)benzamide,
3-fluoro-4-(9-isopropyl-8-phenylamino-9H-purin-2-ylamino)-N-(4-methylpiperidin-1-yl)benzamide,
3-fluoro-4-(9-isopropyl-8-(3-chloro-4-fluorophenylamino)-9H-purin-2-ylamino)-N-(4-methylpiperidin-1-yl)benzamide,
3-fluoro-4-(9-isopropyl-8-phenylamino-9H-purin-2-ylamino)-N-(4-methylpiperazin-1-yl)benzamide,
3-methoxy-4-(9-isopropyl-8-phenylamino-9H-purin-2-ylamino)-N-(4-methylpiperazin-1-yl)benzamide,
4-(8-(3-chloro-4-fluorophenylamino)-9-isopropyl-9H-purin-2-ylamino)-3-methoxy-N-(1-methylpiperidin-4-yl)benzamide,
4-(8-phenylamino-9-isopropyl-9H-purin-2-ylamino)-N-(1-methylpiperidin-4-yl)benzamide,
9-isopropyl-2-(4-(4-methylpiperazin-1-yl)phenylamino)-8-phenylamino-9H-purine,
8-(3-bromophenylamino)-9-isopropyl-2-(4-(4-methylpiperazin-1-yl)phenylamino)-9H-purine,
8-(3-ethynylphenylamino)-9-isopropyl-2-(4-(4-methylpiperazin-1-yl)phenylamino)-9H-purine,
8-(3-chloro-4-fluorophenylamino)-9-isopropyl-2-(4-(4-methylpiperazin-1-yl)phenylamino)-9H-purine,
8-(3-bromophenylamino)-9-cyclopropyl-2-(4-(4-methylpiperazin-1-yl)phenylamino)-9H-purine,
8-(4-bromophenylamino)-9-isopropyl-2-(4-(4-methylpiperazin-1-yl)phenylamino)-9H-purine,
8-(3-trifluoromethylphenylamino)-9-isopropyl-2-(4-(4-methylpiperazin-1-yl)phenylamino)-9H-purine,
8-(3-methoxyphenylamino)-9-isopropyl-2-(4-(4-methylpiperazin-1-yl)phenylamino)-9H-purine,
8-(4-methoxyphenylamino)-9-isopropyl-2-(4-(4-methylpiperazin-1-yl)phenylamino)-9H-purine,
8-(3-chloro-4-(3-fluorobenzyloxy)phenylamino)-9-isopropyl-2-(4-(4-methylpiperazin-1-yl)phenylamino)-9H-purine,
8-(3-chloro-4-((pyridin-2-yl)methoxy)phenylamino)-9-isopropyl-2-(4-(4-methylpiperazin-1-yl)phenylamino)-9H-purine,
8-(3-(3-(3-chloro-4-fluorophenyl)ureido)phenylamino)-9-isopropyl-2-(4-(4-methylpiperazin-1-yl)phenylamino)-9H-purine,
8-(4-(3-fluorophenylcarbamoyl)phenylamino)-9-isopropyl-2-(4-(4-methylpiperazin-1-yl)phenylamino)-9H-purine,
8-phenylamino-9-cyclopropyl-2-(4-(4-methylpiperazin-1-yl)phenylamino)-9H-purine,
8-phenylamino-9-methyl-2-(4-(4-methylpiperazin-1-yl)phenylamino)-9H-purine,
8-phenylamino-2-(4-(4-methylpiperazin-1-yl)phenylamino)-9H-purine,
8-phenylamino-9-cyclopentyl-2-(4-(4-methylpiperazin-1-yl)phenylamino)-9H-purine,
8-(4-trifluoromethylphenylamino)-9-isopropyl-2-(4-(4-methylpiperazin-1-yl)phenylamino)-9H-purine,
8-(3-acrylylaminophenylamino)-9-isopropyl-2-(4-(4-methylpiperazin-1-yl)phenylamino)-9H-p urine,
9-isopropyl-2-(4-(4-methylpiperazin-1-yl)phenylamino)-8-(pyridin-3-yl)-9H-purine,
9-isopropyl-2-(4-(4-methylpiperazin-1-yl)phenylamino)-8-cyclohexyl-9H-purine,
9-cyclopentyl-6-methyl-2-(4-(4-methylpiperazin-1-yl)phenylamino)-8-phenyl-9H-purine,
9-isopropyl-6-methoxy-2-(4-(4-methylpiperazin-1-yl)phenylamino)-8-phenyl-9H-purine,
9-isopropyl-6-methylamino-2-(4-(4-methylpiperazin-1-yl)phenylamino)-8-phenyl-9H-purine,
9-isopropyl-6-methyl-2-(4-(4-methylpiperazin-1-yl)phenylamino)-8-phenyl-9H-purine,
9-isopropyl-6-methyl-2-(4-(4-methylpiperazin-1-yl)phenylamino)-8-phenyl-9H-purine,
9-cyclopentyl-2-(4-(4-methylpiperazin-1-yl)phenylamino)-8-(pyridin-3-yl)-9H-purine, 4-(9-cyclopentylamino-8-(pyridin-3-ylamino)-9H-purin-2-ylamino)-N-(4-methylpiperidin-1-yl)benzamide, N-(3-(9-isopropyl-8-phenylamino-9H-purin-2-ylamino)phenyl)acrylamide, 8-(4-bromophenylamino)-9-cyclopentyl-2-(4-(4-methylpiperazin-1-yl)phenylamino)-9H-purine, 8-(3-nitrophenylamino)-9-cyclopentyl-2-(4-(4-methylpiperazin-1-yl)phenylamino)-9H-purine, 8-benzylamino-9-cyclopentyl-2-(4-(4-methylpiperazin-1-yl)phenylamino)-9H-purine, 8-(3-ethynylphenylamino)-9-cyclopentyl-2-(4-(4-methylpiperazin-1-yl)phenylamino)-9H-purine, 8-(2-fluoro-4-bromophenylamino)-9-cyclopentyl-2-(4-(4-methylpiperazin-1-yl)phenylamino)-9H-purine, 8-phenylamino-9-cyclopentyl-2-(4-(4-morpholinylmethyl)phenylamino)-9H-purine, 8-(3-fluorophenylamino)-9-cyclopentyl-2-(4-(4-methylpiperazin-1-yl)phenylamino)-9H-purine, 8-phenylamino-9-cyclohexyl-2-(4-(4-methylpiperazin-1-yl)phenylamino)-9H-purine, 8-(3-hydroxyphenylamino)-9-cyclopentyl-2-(4-(4-methylpiperazin-1-yl)phenylamino)-9H-purine, 8-(3-chlorophenylamino)-9-cyclopentyl-2-(4-(4-methylpiperazin-1-yl)phenylamino)-9H-purine, 8-(3-methylphenylamino)-9-cyclopentyl-2-(4-(4-methylpiperazin-1-yl)phenylamino)-9H-purine, 8-(3,5-dichlorophenylamino)-9-cyclopentyl-2-(4-(4-methylpiperazin-1-yl)phenylamino)-9H-purine, 8-(2,5-difluorophenylamino)-9-cyclopentyl-2-(4-(4-methylpiperazin-1-yl)phenylamino)-9H-purine, 8-phenylamino-9-cyclopentyl-2-(4-(2-methoxyethoxy)phenylamino)-9H-purine, 8-(2,4,5-trichlorophenylamino)-9-cyclopentyl-2-(4-(4-methylpiperazin-1-yl)phenylamino)-9H-purine, 8-phenylamino-9-cyclopentyl-2-(4-((4-ethylpiperazin-1-yl)methyl)phenylamino)-9H-purine, 8-phenylamino-9-cyclopentyl-2-(4-((4-methylpiperazin-1-yl)methyl)phenylamino)-9H-purine, 8-(2,5-dichlorophenylamino)-9-cyclopentyl-2-(4-(4-methylpiperazin-1-yl)phenylamino)-9H-purine, 8-(2,6-dichlorophenylamino)-9-cyclopentyl-2-(4-(4-methylpiperazin-1-yl)phenylamino)-9H-purine, 8-(3-bromophenylamino)-9-cyclopentyl-2-(4-(4-methylpiperazin-1-yl)phenylamino)-9H-purine, 8-phenylamino-9-cyclohexylmethyl-2-(4-(4-methylpiperazin-1-yl)phenylamino)-9H-purine, 9-isopropylamino-2-(4-(2-morpholinoethoxy)phenylamino))-8-phenylamino-9H-purine, 9-isopropylamino-2-(4-(3-(4-methylpiperazin-1-yl)propylamino)phenylamino)-8-phenylamino-9H-purine, 8-(6-chloropyrimidin-3-yl)-9-isopropylamino-2-(4-(3-(4-methylpiperazin-1-yl)propylamino)phenylamino)-9H-purine, or 8-(3-chloro-4-(3-fluorobenzyloxy)phenylamino)-9-isopropyl-2-(4-morpholinophenylamino)-9H-purine.

A second technical solution to be solved in the present invention is to provide a process for synthesizing an arylamino purine derivative represented by formula I, which process comprises:

using 2,4-dichloro-5-nitropyrimidine substituted at 6-position by a substituent group as starting material; introducing a $R_1$-substituted amino at 4-position by a low temperature substituting process; then introducing

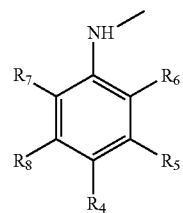

at 2-position by a high temperature substituting process; reducing the nitro at 5-position to amino; and finally forming a closed pyrazole ring with $R_3$NCS ($R_3$-substituted isothiocyanate), or

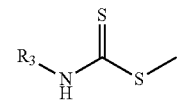

($R_3$-substituted methyl phenylcarbamodithioate) to obtain the targeted product.

The synthesis route is shown as below:

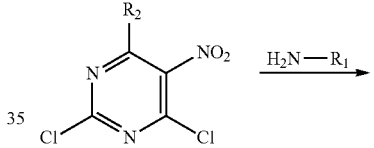

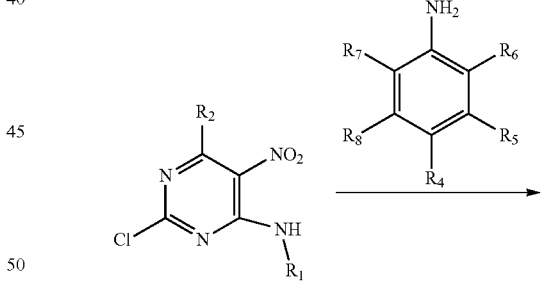

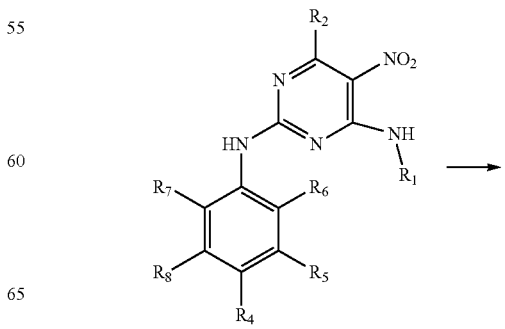

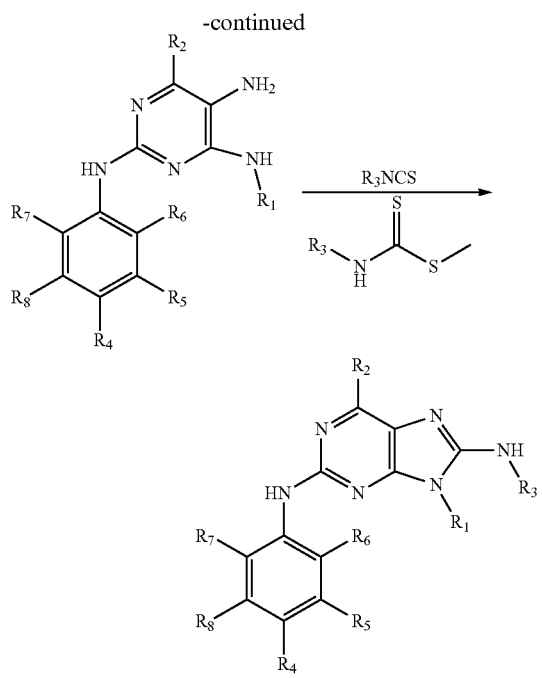

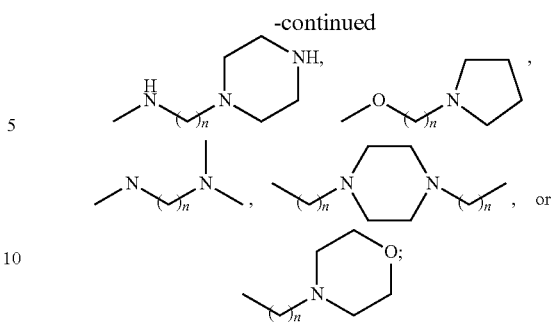

R$_1$ represents —H, —C$_{11}$H$_{(2m+1)}$, C$_3$-C$_2$cycloalkyl, —C$_m$H$_{(2m+1)}$ substituted by C$_3$-C$_2$cycloalkyl, C$_3$-C$_2$cycloalkyl substituted by —C$_m$H$_{(2m+1)}$, heterocyclyl containing 3-8 carbon atoms, amino substituted by heterocyclyl containing 3-8 carbon atoms, aryl containing 6-8 carbon atoms, or heteroaryl containing 6-8 carbon atoms; said heterocyclyl contains 1-3 heteroatoms selected from N, O and S; said heteroaryl contains 1-3 heteroatoms selected from N, O and S;

R$_2$ represents —H, —NH$_2$, —OH, —F, —Cl, —Br, —CF$_3$, —C$_m$H$_{(2m+1)}$, —OC$_m$H$_{(2m+1)}$, —NHC$_m$H$_{(2m+1)}$, aryloxy containing 6-12 carbon atoms, or arylamino containing 6-12 carbon atoms;

R$_3$ represents C$_3$-C$_2$cycloalkyl, C$_3$-C$_2$cycloalkyl substituted by —C$_m$H$_{(2m+1)}$, aryl containing 6-80 carbon atoms, or heteroaryl containing 6-80 carbon atoms; said heteroaryl contains 1-15 heteroatoms selected from N, O and S;

R$_4$-R$_8$ respectively represent —H, —F, —Cl, —Br, —CF$_3$, —OCF$_3$, —OC$_m$H$_{(2m+1)}$,

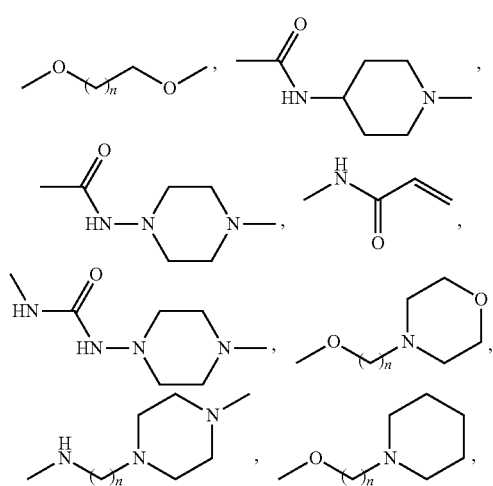

m=1-8; and
n=0-4.

The advantages of said process lie in the short reaction step and the cheap and easily obtainable starting materials and agents.

A third technical solution to be solved in the present invention is to provide a use of the above-mentioned arylamino purine derivative represented by formula I in the manufacture of a medicament for the treatment of tumors.

The present invention also provides a pharmaceutical composition containing an arylamino purine derivative represented by formula I or its pharmaceutical acceptable salt. Said pharmaceutical composition can be used to prepare antitumor drugs.

The advantages of the present inventions lie in that it is proved by experiment that the present arylamino purine derivative is a multiple-kinase inhibitor that targets the kinases such as EGFR, VEGFR and MET. The present arylamino purine derivative has not only a good inhibitory effect on the non-small cell lung carcinoma with deletion mutation of exon 19 and L858R point mutation of exon 21 in EGFR, but also a good inhibitory effect on the non-small cell lung carcinoma that is resistant to Gefitinib. The present arylamino purine derivative also has a good inhibitory effect on other types of tumors. Therefore, the present arylamino purine derivative can be useful to prepare a pharmaceutical composition against these tumors. The present invention provides a new option in the field of preparing antitumor drugs, and has a good market prospect.

DETAILED DESCRIPTION OF THE INVENTION

Figure 1:
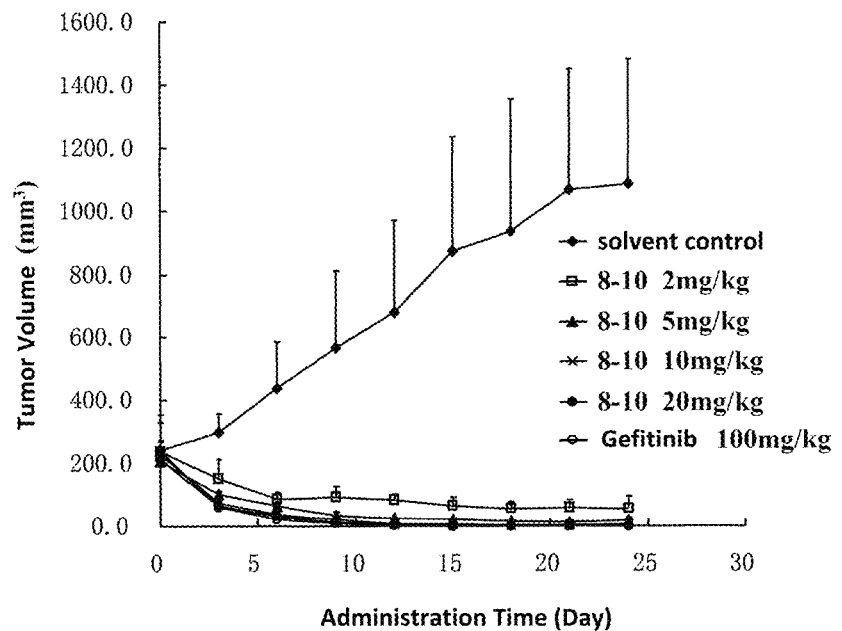
FIG. 1 illustrates the in-vivo anti-tumor effect of Compound 8-10 and provides the tumor growth curves in a nude mouse subcutaneously transplanted human non-small cell lung carcinoma (HCC827 cell strain) model.

Hereinafter, the present invention will be further illustrated with reference to the following examples. However, these examples are only provided for illustration purposes, and are not to limit the scope of the present invention. All of the modifications made based on the above disclosures will fall into the scope of the present invention.

The reaction formulae in the Example are summarized as follows:

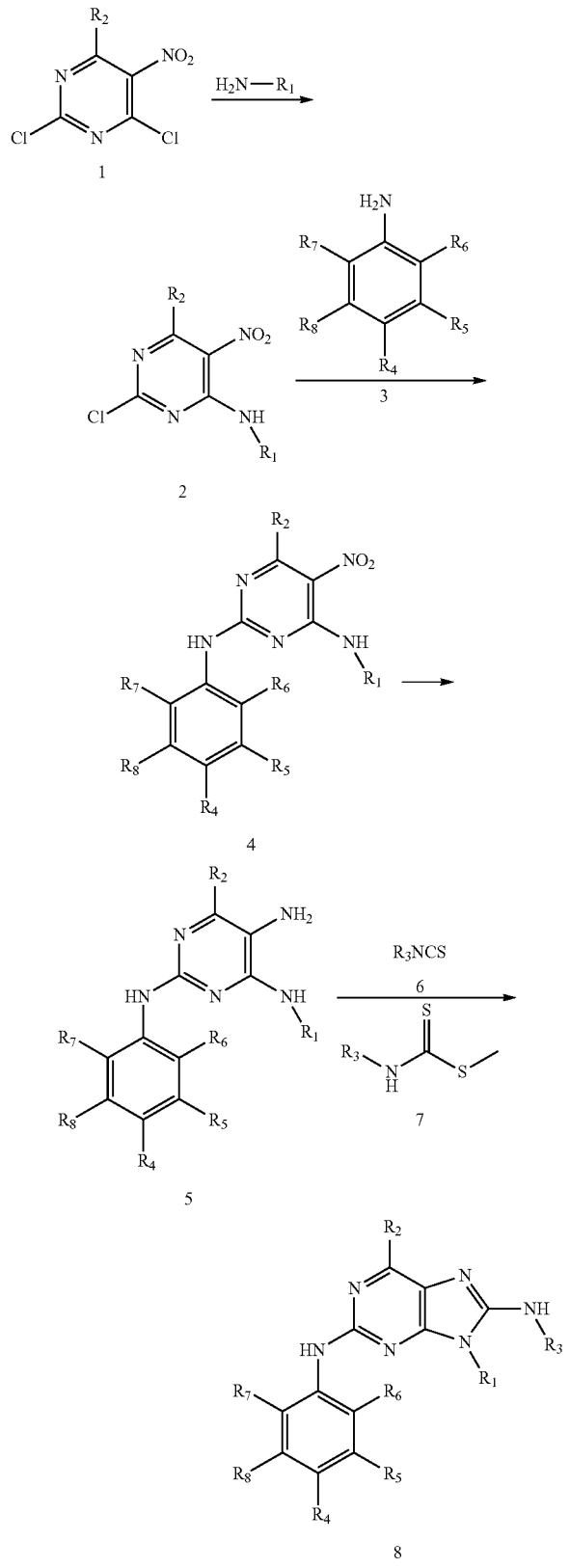

$R_1$ represents —H, —$C_mH_{(2m+1)}$, $C_3$-$C_2$cycloalkyl, —$C_mH_{(2m+1)}$ substituted by $C_3$-$C_2$cycloalkyl, $C_3$-$C_2$cycloalkyl substituted by —$C_mH_{(2m+1)}$, heterocyclyl containing 3-8 carbon atoms, amino substituted by heterocyclyl containing 3-8 carbon atoms, aryl containing 6-8 carbon atoms, or heteroaryl containing 6-8 carbon atoms; said heterocyclyl contains 1-3 heteroatoms selected from N, O and S; said heteroaryl contains 1-3 heteroatoms selected from N, O and S;

$R_2$ represents —H, —$NH_2$, —OH, —F, —Cl, —Br, —$CF_3$, —$C_mH_{(2m+1)}$, —$OC_mH_{(2m+1)}$, —$NHC_mH_{(2m+1)}$, aryloxy containing 6-12 carbon atoms, or arylamino containing 6-12 carbon atoms;

$R_3$ represents $C_3$-$C_2$cycloalkyl, $C_3$-$C_2$cycloalkyl substituted by —$C_mH_{(2m+1)}$, aryl containing 6-80 carbon atoms, or heteroaryl containing 6-80 carbon atoms; said heteroaryl contains 1-15 heteroatoms selected from N, O and S;

$R_4$-$R_8$ respectively represent —H, —F, —Cl, —Br, —$CF_3$, —$OCF_3$, —$OC_mH_{(2m+1)}$,

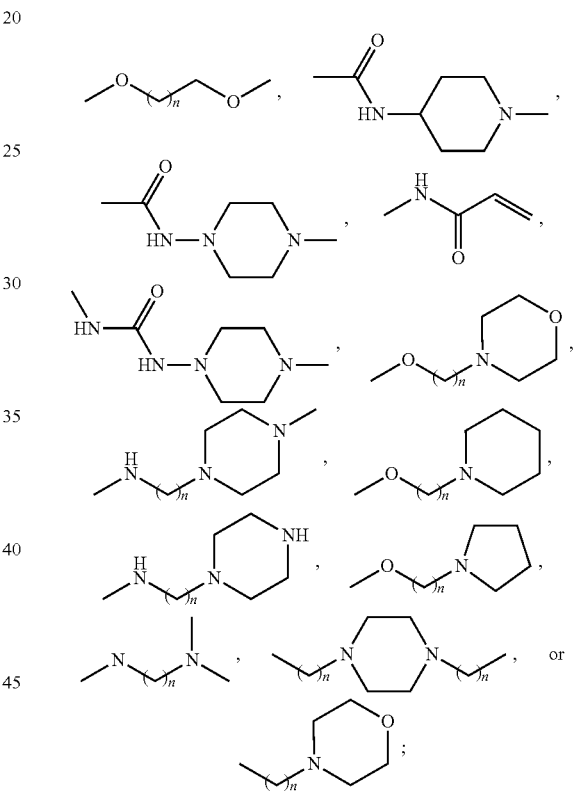

m=1-8; and
n=0-4.

Example 1

The Preparation of 2-chloro-4-amino-5-nitropyrimidine 2-1

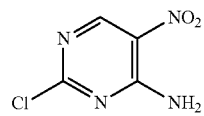

Aqueous ammonia (8.0 ml) and N,N-diisopropylethylamine (13.2 ml) were dissolved into 150 ml dichloromethane. The mixture was added dropwise to a solution of 2,4-dichloro-5-nitropyrimidine (10.0 g) in dichloromethane (30 ml) at 0° C. After the completion of the dropwise addition, the mixture was kept at the same temperature to react for 1 hour. The precipitate was filtered off. The filter cake was recrystallized to obtain a yellow solid (8.1 g) in a yield of 90.1%. $^1$H NMR (400 MHz, DMSO-$d_6$): δ 9.20 (s, 1H), 9.02 (s, 1H), 8.60 (s, 1H) ppm.

Example 2

The Preparation of
2-chloro-4-methylamino-5-nitropyrimidine

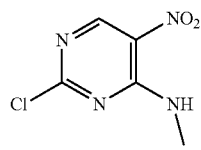

2-2

A solution of methyl amine-ethanol (7.6 ml) and N,N-diisopropylethylamine (13.2 ml) were dissolved into 150 ml dichloromethane. The mixture was added dropwise to a solution of 2,4-dichloro-5-nitropyrimidine (10.0 g) in dichloromethane (30 ml) at 0° C. After the completion of the dropwise addition, the mixture was kept at the same temperature to react for half an hour. Purification was conducted by a column chromatography to obtain a yellow solid (8.3 g) in a yield of 85.4%. $^1$H NMR (400 MHz, CDCl$_3$): δ 9.05 (s, 1H), 8.41 (s, 1H), 3.22 (s, 3H) ppm.

Example 3

The Preparation of
2-chloro-4-isopropylamino-5-nitropyrimidine

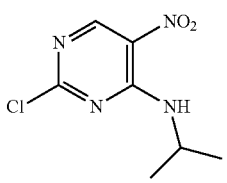

2-3

Isopropylamine (4.5 ml) and N,N-diisopropylethylamine (13.2 ml) were dissolved into 150 ml dichloromethane. The mixture was added dropwise to a solution of 2,4-dichloro-5-nitropyrimidine (10.0 g) in dichloromethane (30 ml) at 0° C. After the completion of the dropwise addition, the mixture was kept at the same temperature to react for half an hour. Purification was conducted by a column chromatography to obtain a bright-yellow solid (10.1 g) in a yield of 90.4%. $^1$H NMR (400 MHz, CDCl$_3$): δ 9.03 (s, 1H), 8.24 (s, 1H), 4.53 (m, 1H), 1.34 (d, J=6.8 Hz, 6H) ppm.

Example 4

The Preparation of
2-chloro-4-cyclopropylamino-5-nitropyrimidine

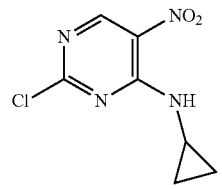

2-4

Cyclopropylamine (1.8 ml) and N,N-diisopropylethylamine (6.6 ml) were dissolved into 75 ml dichloromethane. The mixture was added dropwise to a solution of 2,4-dichloro-5-nitropyrimidine (5.0 g) in dichloromethane (15 ml) at 0° C. After the completion of the dropwise addition, the mixture was kept at the same temperature to react for 40 min. Purification was conducted by a column chromatography to obtain a bright-yellow solid (2.6 g) in a yield of 47%. $^1$H NMR (400 MHz, CDCl$_3$): δ 8.84 (s, 1H), 7.35 (s, 1H), 3.84 (m, 1H), 1.36 (m, 4H) ppm.

Example 5

The Preparation of
2-chloro-4-cyclopentylamino-5-nitropyrimidine

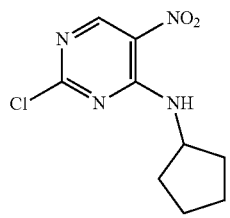

2-5

Cyclopentylamine (5.17 ml) and N,N-diisopropylethylamine (12.4 ml) were dissolved into 125 ml dichloromethane. The mixture was added dropwise to a solution of 2,4-dichloro-5-nitropyrimidine (9.7 g) in dichloromethane (30 ml) at 0° C. After the completion of the dropwise addition, the mixture was kept at the same temperature to react for 80 min. Purification was conducted by a column chromatography to obtain a bright-yellow solid (7.9 g) in a yield of 65.13%. $^1$H NMR (400 MHz, CDCl$_3$): δ 9.03 (s, 1H), 8.38 (s, 1H), 4.59 (m, 1H), 2.13-2.21 (m, 2H), 1.72-1.85 (m, 4H), 1.53-1.71 (m, 2H) ppm.

Example 6

The Preparation of 2-chloro-4-cyclopentylamino-5-nitro-6-methylpyrimidine

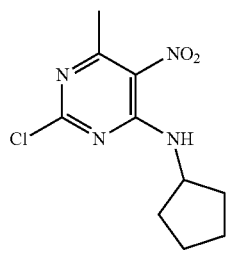

2-6

Cyclopentylamine (5.2 ml) and N,N-diisopropylethylamine (13.2 ml) were dissolved into 150 ml dichloromethane. The mixture was added dropwise to a solution of 2,4-dichloro-5-nitro-6-methylpyrimidine (10.7 g) in dichloromethane (30 ml) at 0° C. After the completion of the dropwise addition, the mixture was kept at the same temperature to react for 1 hour. Purification was conducted by a column chromatography to obtain a bright-yellow solid (11.2 g) in a yield of 84.8%. $^1$H NMR (400 MHz, CDCl$_3$): δ 8.44 (s, 2H), 4.41 (m, 1H), 2.64 (s, 3H), 2.01-2.15 (m, 2H), 1.61-1.76 (m, 4H), 1.45-1.63 (m, 2H) ppm.

Example 7

The Preparation of 2-chloro-4-isopropylamino-5-nitro-6-methoxypyrimidine

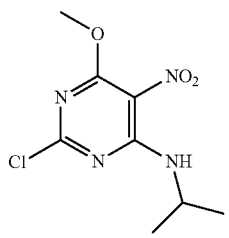

2-7

Isopropylamine (4.5 ml) and N,N-diisopropylethylamine (13.2 ml) were dissolved into 150 ml dichloromethane. The mixture was added dropwise to a solution of 2,4-dichloro-5-nitro-6-methoxypyrimidine (11.5 g) in dichloromethane (30 ml) at 0° C. After the completion of the dropwise addition, the mixture was kept at the same temperature to react for 45 min. Purification was conducted by a column chromatography to obtain a yellow solid (10.9 g) in a yield of 86.1%. $^1$H NMR (400 MHz, CDCl$_3$): δ 8.25 (s, 1H), 4.42 (m, 1H), 4.01 (s, 3H), 1.23 (d, J=6.8 Hz, 6H) ppm.

Example 8

The Preparation of 2-chloro-4-isopropylamino-5-nitro-6-methylaminopyrimidine

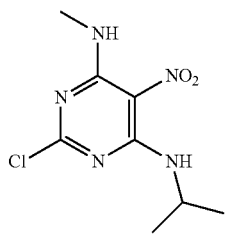

2-8

Isopropylamine (4.5 ml) and N,N-diisopropylethylamine (13.2 ml) were dissolved into 150 ml dichloromethane. The mixture was added dropwise to a solution of 2,4-dichloro-5-nitro-6-methylaminopyrimidine (11.5 g) in dichloromethane (30 ml) at 0° C. After the completion of the dropwise addition, the mixture was kept at the same temperature to react for half an hour. Purification was conducted by a column chromatography to obtain a yellow solid (10.4 g) in a yield of 82.1%. $^1$H NMR (400 MHz, CDCl$_3$): δ8.17 (s, 1H), 4.48 (m, 1H), 2.78 (s, 3H), 1.31 (d, J=6.8 Hz, 6H) ppm.

Example 9

The Preparation of 2-chloro-4-isopropylamino-5-nitro-6-methylpyrimidine

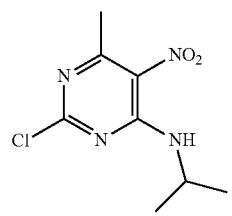

2-9

Isopropylamine (4.5 ml) and N,N-diisopropylethylamine (13.2 ml) were dissolved into 150 ml dichloromethane. The mixture was added dropwise to a solution of 2,4-dichloro-5-nitro-6-methylpyrimidine (10.7 g) in dichloromethane (30 ml) at 0° C. After the completion of the dropwise addition, the mixture was kept at the same temperature to react for half an hour. Purification was conducted by a column chromatography to obtain a bright-yellow solid (10.2 g) in a yield of 86.8%. $^1$H NMR (400 MHz, CDCl$_3$): δ 8.01 (s, 1H), 4.48 (m, J=4.1, 1H), 2.72 (s, 3H), 1.32 (d, J=6.8 Hz, 6H) ppm.

Example 10

The Preparation of 2-chloro-4-cyclohexylamino-5-nitropyrimidine

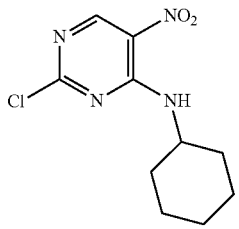

2-10

Cyclohexylamine (5.72 ml) and N,N-diisopropylethylamine (12.4 ml) were dissolved into 125 ml dichloromethane. The mixture was added dropwise to a solution of 2,4-dichloro-5-nitropyrimidine (9.7 g) in dichloromethane (30 ml) at 0° C. After the completion of the dropwise addition, the mixture was kept at the same temperature to react for 80 min. Purification was conducted by a column chromatography to obtain a bright-yellow solid (9.1 g) in a yield of 71.2%. ESI-MS (m/z, %) 258 (M−H)$^+$; $^1$H NMR (400 MHz, CDCl$_3$): δ9.04 (s, 1H), 8.35 (s, 1H), 4.34 (m, 1H), 2.03 (m, 2H), 1.79 (m, 2H), 1.53-1.25 (m, 6H).

Example 11

The Preparation of 2-chloro-4-cyclohexylmethylamino-5-nitropyrimidine

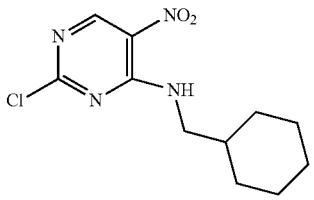

2-11

Cyclohexylmethylamine (3.11 g) and N,N-diisopropylethylamine (6.2 ml) were dissolved into 45 ml dichloromethane. The mixture was added dropwise to a solution of 2,4-dichloro-5-nitropyrimidine (4.85 g) in dichloromethane (30 ml) at 0° C. After the completion of the dropwise addition, the mixture was kept at the same temperature to react for 20 min. Purification was conducted by a column chromatography to obtain a bright-yellow sheet-like solid (1.73 g) in a yield of 26%. ESI-MS (m/z, %) 272 (M−H)$^+$. $^1$H NMR (400 MHz, CDCl$_3$): δ 9.03 (s, 1H), 8.48 (s, 1H), 3.52 (m, 2H), 1.78-1.64 (m, 7H), 1.33-1.14 (m, 4H), 1.08-1.00 (m, 2H).

Example 12

The Preparation of 4-(4-isopropylamino-5-nitropyrimidin-2-ylamino)-N-(4-methylpiperazin-1-yl)benzamide

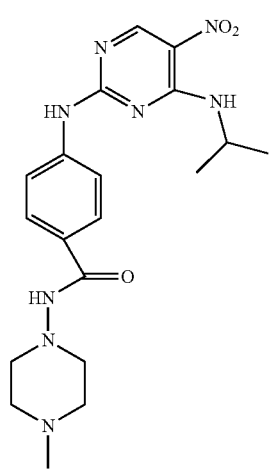

4-1

4-amino-N-(4-methylpiperazin-1-yl)benzamide (4.7 g) was added to a solution of Compound 2-3 (4.3 g) in n-butanol (150 ml). The mixture was reacted at 90° C. for 3.5 hours, cooled to room temperature, filtered, washed and dried to obtain a yellow solid (5.9 g) in a yield of 71.2%. $^1$H NMR (400 MHz, DMSO-d$_6$): δ 10.01 (s, 1H), 9.32 (s, 1H), 8.78 (s, 1H), 8.21 (m, 2H), 7.84 (s, 1H), 7.63 (m, 2H), 4.31 (m, 1H), 2.75 (t, J=4.8 Hz, 4H), 2.38 (br, 4H), 2.13 (s, 3H), 1.19 (d, J=6.8 Hz, 6H) ppm.

Example 13

The Preparation of 3-fluoro-4-(4-isopropylamino-5-nitropyrimidin-2-ylamino)-N-(4-methylpiperazin-1-yl)benzamide

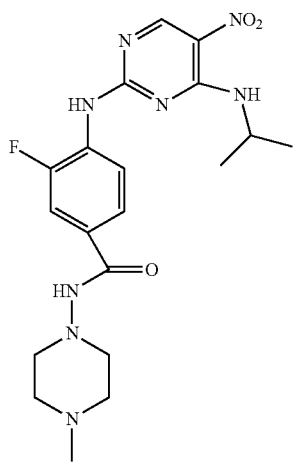

4-2

4-amino-3-fluoro-N-(4-methylpiperazin-1-yl)benzamide (5.0 g) was added to a solution of Compound 2-3 (4.3 g) in n-butanol (150 ml). The mixture was reacted at 90° C. for 4 hours, cooled to room temperature, filtered, washed and dried to obtain a yellow solid (6.5 g) in a yield of 75.7%. $^1$H NMR (400 MHz, DMSO-d$_6$): δ 10.11 (s, 1H), 9.47 (s, 1H), 8.99 (s, 1H), 8.38 (d, J=7.6 Hz, 1H), 7.86 (m, 1H), 7.65 (m, 2H), 4.27 (m, 1H), 2.89 (t, J=4.8 Hz, 4H), 2.42 (br, 4H), 2.19 (s, 3H), 1.23 (d, J=6.4 Hz, 6H) ppm.

Example 14

The Preparation of 3-methoxy-4-(4-isopropylamino-5-nitropyrimidin-2-ylamino)-N-(4-methylpiperazin-1-yl)benzamide

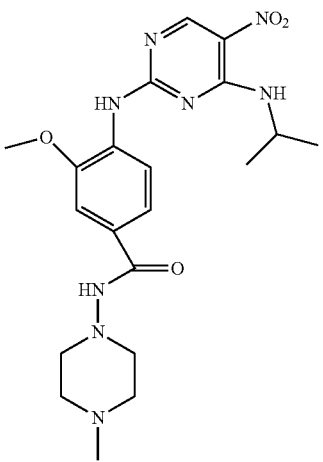

4-3

4-amino-3-methoxy-N-(4-methylpiperazin-1-yl)benzamide (5.3 g) was added to a solution of Compound 2-3 (4.3 g) in n-butanol (150 ml). The mixture was reacted at 90° C. for 4.5 hours, cooled to room temperature, filtered, washed and dried to obtain a yellow solid (6.8 g) in a yield of 77.1%. $^1$H NMR (400 MHz, DMSO-$d_6$): δ 9.13 (s, 1H), 8.38 (d, J=6.8 Hz, 1H), 7.93 (m, 1H), 7.63 (d, J=8.0 Hz, 1H), 7.46 (m, 1H), 7.08 (m, 1H), 7.01 (m, 1H), 4.31 (m, 1H), 3.86 (s, 3H), 3.55 (br, 4H), 2.52 (br, 4H), 2.32 (s, 3H), 1.24 (d, J=6.4 Hz, 6H) ppm.

Example 15

The Preparation of 4-(4-isopropylamino-5-nitropyrimidin-2-ylamino)-N-(1-methylpiperidin-4-yl)benzamide

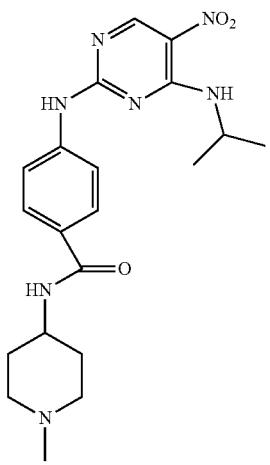

4-4

4-amino-N-(4-methylpiperidin-1-yl)benzamide (4.6 g) was added to a solution of Compound 2-3 (4.3 g) in n-butanol (150 ml). The mixture was reacted at 90° C. for 4.5 hours, cooled to room temperature, filtered, washed and dried to obtain a yellow solid (5.7 g) in a yield of 70.0%. $^1$H NMR (400 MHz, DMSO-$d_6$): δ 10.58 (s, 1H), 9.02 (s, 1H), 8.48 (d, J=5.6 Hz, 1H), 8.20 (d, J=6.8 Hz, 1H), 7.86 (m, 4H), 4.45 (m, 1H), 3.80 (m, 1H), 2.94 (br, 4H), 2.32 (s, 3H), 1.62-1.83 (m, 4H), 1.33 (d, J=6.4 Hz, 6H) ppm.

Example 16

The Preparation of 4-amino-2-(4-(4-methylpiperazin-1-yl)phenylamino)-5-nitropyrimidine

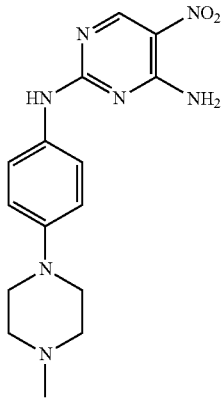

4-5

4-(4-methylpiperazinyl)phenylamine (3.8 g) was added to a solution of Compound 2-1 (3.5 g) in n-butanol (150 ml). The mixture was reacted at 90° C. for 4.5 hours, cooled to room temperature, filtered, washed and dried to obtain a red solid (5.2 g) in a yield of 79.5%. $^1$H NMR (400 MHz, CDCl$_3$): δ 9.07 (s, 1H), 8.52 (s, 2H), 8.40 (s, 1H), 7.57 (s, 1H), 7.51 (s, 1H), 7.10 (m, 2H), 3.31 (t, J=4.8 Hz, 4H), 2.81 (t, J=4.8 Hz, 4H), 2.30 (s, 3H) ppm.

Example 17

The Preparation of 4-methylamino-2-(4-(4-methylpiperazin-1-yl)phenylamino)-5-nitropyrimidine

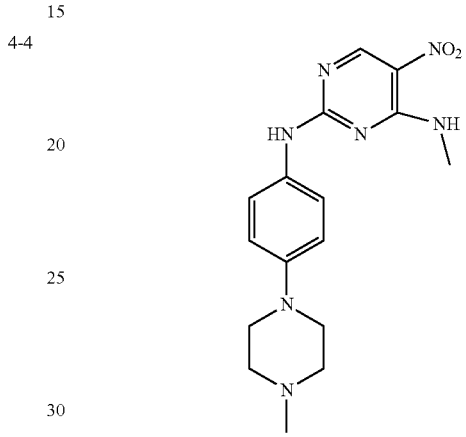

4-6

4-(4-methylpiperazinyl)phenylamine (3.8 g) was added to a solution of Compound 2-2 (3.8 g) in n-butanol (150 ml). The mixture was reacted at 90° C. for 3.5 hours, cooled to room temperature, filtered, washed and dried to obtain a red solid (5.1 g) in a yield of 74.8%. $^1$H NMR (400 MHz, CDCl$_3$): δ 9.11 (s, 1H), 8.34 (s, 1H), 7.59 (s, 1H), 7.51 (m, 2H), 7.23 (m, 2H), 4.21 (s, 3H), 3.15 (t, J=4.8 Hz, 4H), 2.87 (t, J=4.8 Hz, 4H), 2.48 (s, 3H) ppm.

Example 18

The Preparation of 4-isopropylamino-2-(4-(4-methylpiperazin-1-yl)phenylamino)-5-nitropyrimidine

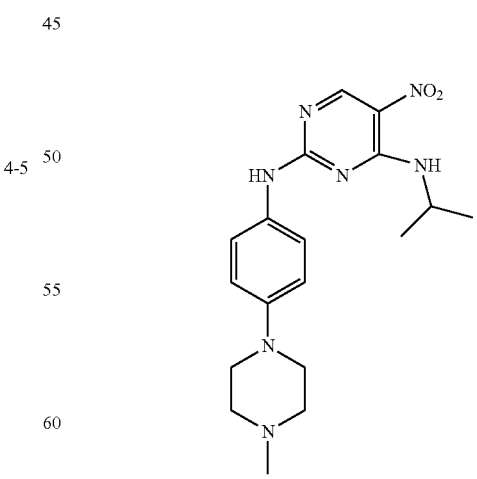

4-7

4-(4-methylpiperazinyl)phenylamine (3.8 g) was added to a solution of Compound 2-3 (4.3 g) in n-butanol (150 ml). The mixture was reacted at 90° C. for 3 hours, cooled to room temperature, filtered, washed and dried to obtain a red solid (6.2 g) in a yield of 84.1%. ¹H NMR (400 MHz, CDCl₃): δ 9.02 (s, 1H), 8.42 (s, 1H), 7.63 (s, 1H), 7.51 (s, 2H), 6.95 (m, 2H), 4.41 (m, 1H), 3.22 (t, J=4.8 Hz, 4H), 2.61 (t, J=4.8 Hz, 4H), 2.37 (s, 3H), 1.33 (d, J=6.4 Hz, 6H) ppm.

Example 19

The Preparation of 4-cyclopropylamino-2-(4-(4-methylpiperazin-1-yl)phenylamino)-5-nitropyrimidine

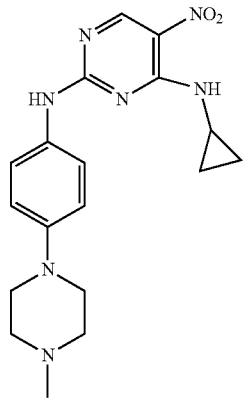

4-8

4-(4-methylpiperazinyl)phenylamine (3.8 g) was added to a solution of Compound 2-4 (4.3 g) in n-butanol (150 ml). The mixture was reacted at 90° C. for 3.5 hours, cooled to room temperature, filtered, washed and dried to obtain a red solid (6.4 g) in a yield of 87.2%. ¹H NMR (400 MHz, CDCl₃): δ 9.08 (s, 1H), 8.39 (s, 1H), 7.90 (s, 1H), 7.58 (m, 2H), 6.94 (m, 2H), 4.32 (m, 1H), 3.05 (t, J=4.8 Hz, 4H), 2.90 (t, J=4.8 Hz, 4H), 2.67 (s, 3H), 1.39 (m, 4H) ppm.

Example 20

The Preparation of 4-cyclopentylamino-2-(4-(4-methylpiperazin-1-yl)phenylamino)-5-nitropyrimidine

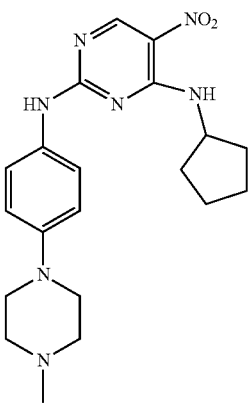

4-9

4-(4-methylpiperazinyl)phenylamine (3.8 g) was added to a solution of Compound 2-5 (4.8 g) in n-butanol (150 ml). The mixture was reacted at 90° C. for 3 hours, cooled to room temperature, filtered, washed and dried to obtain a red solid (6.0 g) in a yield of 76.0%. ¹H NMR (400 MHz, CDCl₃): δ 9.03 (s, 1H), 8.47 (s, 1H), 7.69 (s, 1H), 7.51 (m, 2H), 7.11 (m, 2H), 4.43 (m, 1H), 3.28 (t, J=4.8 Hz, 4H), 2.67 (t, J=4.8 Hz, 4H), 2.45 (s, 3H), 2.15-2.23 (m, 2H), 1.74-1.86 (m, 4H), 1.50-1.72 (m, 2H) ppm.

Example 21

The Preparation of 4-cyclopentylamino-2-(4-(4-methylpiperazin-1-yl)phenylamino)-5-nitro-6-methylpyrimidine

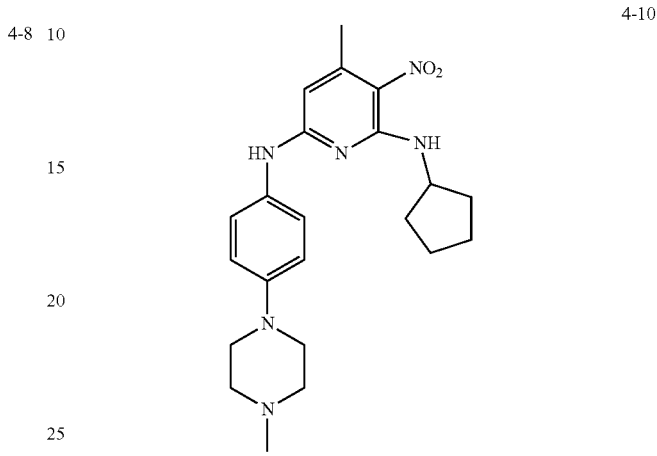

4-10

4-(4-methylpiperazinyl)phenylamine (3.8 g) was added to a solution of Compound 2-6 (5.1 g) in n-butanol (150 ml). The mixture was reacted at 90° C. for 5 hours, cooled to room temperature, filtered, washed and dried to obtain a red solid (6.4 g) in a yield of 78.3%. ¹H NMR (400 MHz, CDCl₃): δ 8.42 (s, 1H), 7.62 (s, 1H), 7.41 (s, 2H), 6.98 (m, 2H), 4.21 (m, 1H), 3.14 (t, J=4.8 Hz, 4H), 2.56 (t, J=4.8 Hz, 4H), 2.51 (s, 3H), 2.34 (s, 3H), 1.47-1.85 (m, 8H) ppm.

Example 22

The Preparation of 4-isopropylamino-2-(4-(4-methylpiperazin-1-yl)phenylamino)-5-nitro-6-methoxypyrimidine

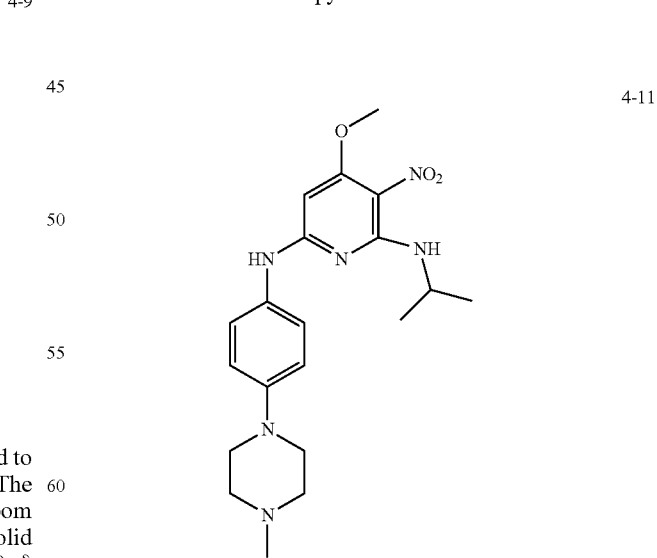

4-11

4-(4-methylpiperazinyl)phenylamine (3.8 g) was added to a solution of Compound 2-7 (4.9 g) in n-butanol (150 ml). The mixture was reacted at 90° C. for 5.5 hours, cooled to room temperature, filtered, washed and dried to obtain a reddish-brown solid (6.5 g) in a yield of 81.5%. $^1$H NMR (400 MHz, CDCl$_3$): δ 8.51 (s, 1H), 7.86 (s, 1H), 7.43 (s, 2H), 7.01 (m, 2H), 4.32 (m, 1H), 3.94 (s, 3H), 3.08 (t, J=4.8 Hz, 4H), 2.64 (t, J=4.8 Hz, 4H), 2.53 (s, 3H), 1.43 (d, J=6.4 Hz, 6H) ppm.

Example 23

The Preparation of 4-isopropylamino-2-(4-(4-methylpiperazin-1-yl)phenylamino)-5-nitro-6-methylaminopyrimidine

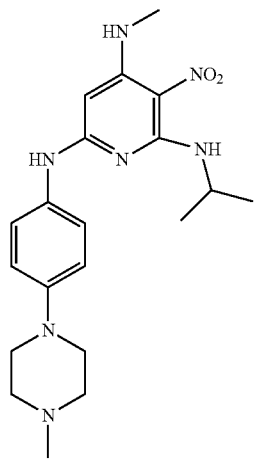

4-12

4-(4-methylpiperazinyl)phenylamine (3.8 g) was added to a solution of Compound 2-8 (4.9 g) in n-butanol (150 ml). The mixture was reacted at 90° C. for 6 hours, cooled to room temperature, filtered, washed and dried to obtain a reddish-brown solid (6.0 g) in a yield of 75.4%. $^1$H NMR (400 MHz, CDCl$_3$): δ 8.58 (s, 1H), 7.81 (s, 1H), 7.47 (s, 2H), 7.08 (m, 2H), 4.45 (m, 1H), 3.14 (t, J=4.8 Hz, 4H), 2.79 (s, 3H), 2.54 (t, J=4.8 Hz, 4H), 2.42 (s, 3H), 1.45 (d, J=6.4 Hz, 6H) ppm.

Example 24

The Preparation of 4-isopropylamino-2-(4-(4-methylpiperazin-1-yl)phenylamino)-5-nitro-6-methylpyrimidine

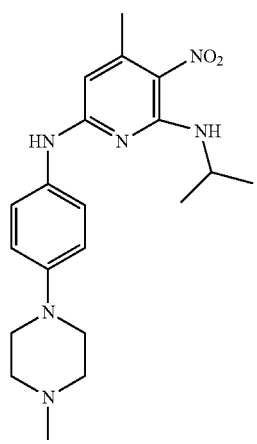

4-13

4-(4-methylpiperazinyl)phenylamine (3.8 g) was added to a solution of Compound 2-9 (4.6 g) in n-butanol (150 ml). The mixture was reacted at 90° C. for 3.5 hours, cooled to room temperature, filtered, washed and dried to obtain a red solid (6.3 g) in a yield of 82.3%. $^1$H NMR (400 MHz, DMSO-d$_6$): δ 11.01 (s, 1H), 10.15 (s, 1H), 7.66 (d, J=8.4, 2H), 6.99 (d, J=9.2, 2H), 4.35 (s, 1H), 3.76 (d, J=11.2, 2H), 3.46 (d, J=10.8, 2H), 3.11 (m, J=13.6, 4H), 2.79 (s, 3H), 2.60 (s, 3H), 1.27 (d, J=6.4, 6H) ppm.

Example 25

The Preparation of 4-(4-cyclopentylamino-5-nitropyrimidin-2-ylamino)-N-(4-methylpiperazin-1-yl)benzamide

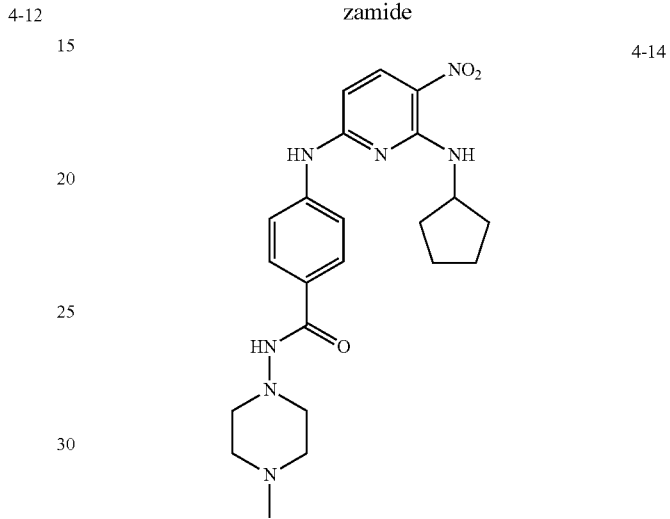

4-14

4-amino-N-(4-methylpiperazin-1-yl)benzamide (4.85 g) was added to a solution of Compound 2-5 (4.7 g) in n-butanol (150 ml). The mixture was reacted at 90° C. for 4.5 hours, cooled to room temperature, filtered, washed and dried to obtain a yellow solid (6.4 g) in a yield of 72.6%. MS m/z (ESI): 441 [M+H]$^+$.

Example 26

The Preparation of 4-(4-isopropylamino-5-nitropyrimidin-2-ylamino)-N-(1-methylpiperidin-4-yl)benzamide

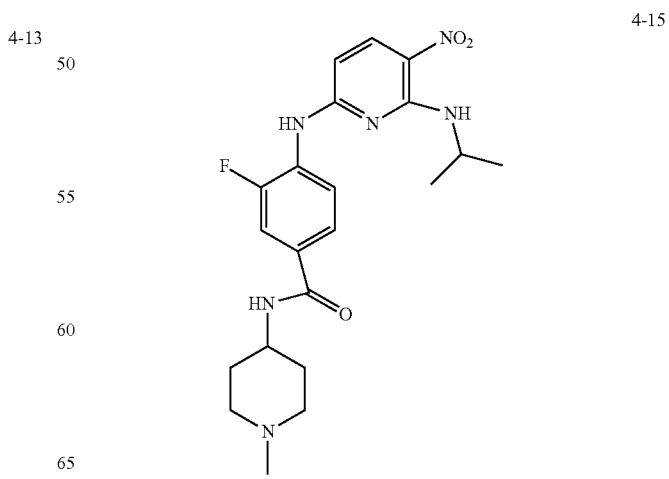

4-15

4-amino-3-fluoro-N-(4-methylpiperidin-1-yl)benzamide (5.0 g) was added to a solution of Compound 2-3 (4.3 g) in n-butanol (150 ml). The mixture was reacted at 90° C. for 4.0 hours, cooled to room temperature, filtered, washed and dried to obtain a yellow solid (6.3 g) in a yield of 72.8%. MS m/z (ESI): 432 [M+H]⁺.

Example 27

The Preparation of N-(3-(4-isopropylamino-5-nitro-pyrimidin-2-ylamino)phenyl)acrylamide

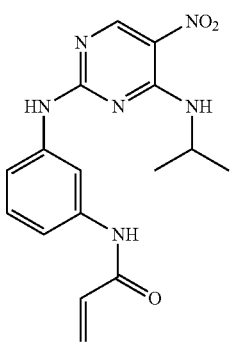

4-16

N-(3-aminophenyl)acrylamide (3.2 g) was added to a solution of Compound 2-3 (4.3 g) in n-butanol (150 ml). The mixture was reacted at 90° C. for 3 hours, cooled to room temperature, filtered, washed and dried to obtain a red solid (6.0 g) in a yield of 88.3%. MS m/z (ESI): 344 [M+H]⁺.

Example 28

The Preparation of 4-isopropylamino-2-(4-(2-morpholinoethoxy)phenylamino)-5-nitropyrimidine

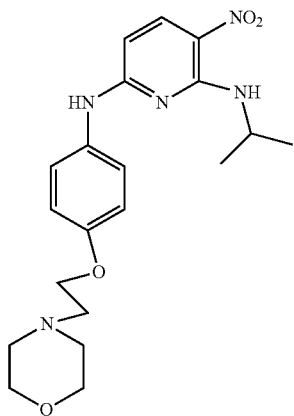

4-17

4-(2-morpholinoethoxy)phenylamine (4.4 g) was added to a solution of Compound 2-3 (4.3 g) in n-butanol (150 ml). The mixture was reacted at 90° C. for 3.5 hours, cooled to room temperature, filtered, washed and dried to obtain a red solid (6.4 g) in a yield of 80.0%. MS m/z (ESI): 403 [M+H]⁺.

Example 29

The Preparation of 4-isopropylamino-2-(4-(3-(4-methylpiperazin-1-yl)propylamino)phenylamino)-5-nitropyrimidine

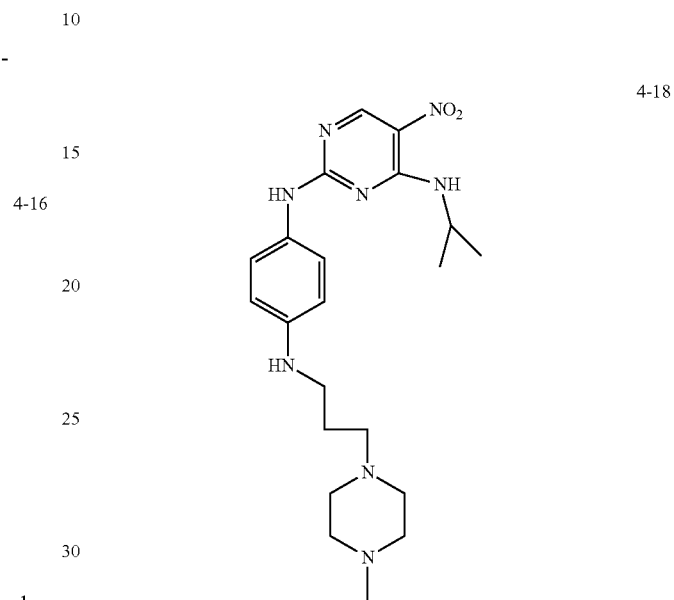

4-18

4-(3-(4-methylpiperazin-1-yl)propylamino)phenylamine (4.9 g) was added to a solution of Compound 2-3 (4.3 g) in n-butanol (150 ml). The mixture was reacted at 90° C. for 4 hours, cooled to room temperature, filtered, washed and dried to obtain a red solid (6.8 g) in a yield of 79.9%. MS m/z (ESI): 429 [M+H]⁺.

Example 30

The Preparation of 4-isopropylamino-2-(4-morpholinophenylamino)-5-nitropyrimidine

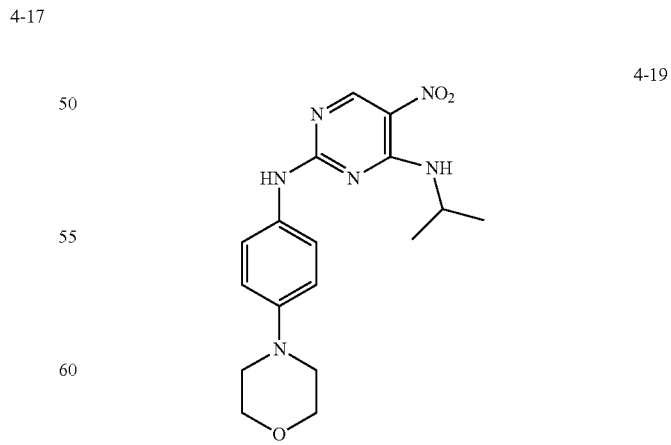

4-19

4-morpholinophenylamine (3.6 g) was added to a solution of Compound 2-3 (4.3 g) in n-butanol (150 ml). The mixture was reacted at 90° C. for 4 hours, cooled to room temperature, filtered, washed and dried to obtain a red solid (5.3 g) in a yield of 74.7%. MS m/z (ESI): 359 [M+H]⁺.

Example 31

The Preparation of 4-cyclopentylamino-2-(4-(4-morpholinylmethyl)phenylamino)-5-nitropyrimidine

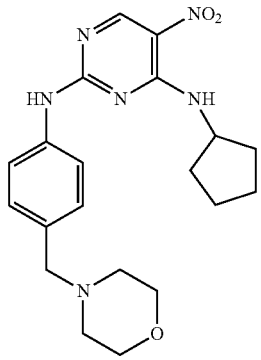

4-20

4-morpholinomethylphenylamine (3.8 g) was added to a solution of Compound 2-5 (4.8 g) in n-butanol (150 ml). The mixture was reacted at 90° C. for 4.0 hours, cooled to room temperature, filtered, washed and dried to obtain a yellow solid (6.3 g) in a yield of 80.6%. MS m/z (ESI): 399 [M+H]⁺.

Example 32

The Preparation of 4-cyclohexylamino-2-(4-(4-methylpiperazin-1-yl)phenylamino)-5-nitropyrimidine

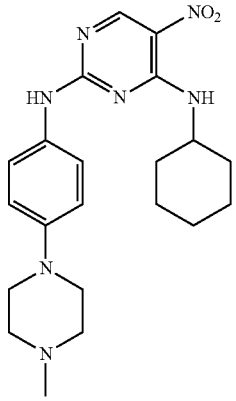

4-21

4-(4-methylpiperazinyl)phenylamine (3.1 g) was added to a solution of Compound 2-10 (2.3 g) in n-butanol (40 ml). The mixture was reacted at 90° C. for 4.0 hours, cooled to room temperature, filtered, washed and dried to obtain a red solid (4.13 g) in a yield of 83.8%. MS m/z (ESI): 412 [M+H]⁺. ¹H NMR (400 MHz, DMSO-d₆): δ 10.71 (s, 1H), 10.35 (s, 1H), 8.96 (s, 1H), 8.48 (d, J=6.8 Hz, 1H), 7.71 (d, J=8.8 Hz, 1H), 6.99 (d, J=9.2 Hz, 2H), 4.04 (m, 1H), 3.78 (m, 2H), 3.46 (m, 2H), 3.15 (m, 2H), 3.04 (m, 2H), 2.83 (s, 1H), 1.98 (m, 2H), 1.65 (m, 1H), 1.43 (m, 4H), 1.26 (m, 1H) ppm.

Example 33

The Preparation of 4-cyclopentylamino-2-(4-(2-methoxyethoxy)phenylamino)-5-nitropyrimidine

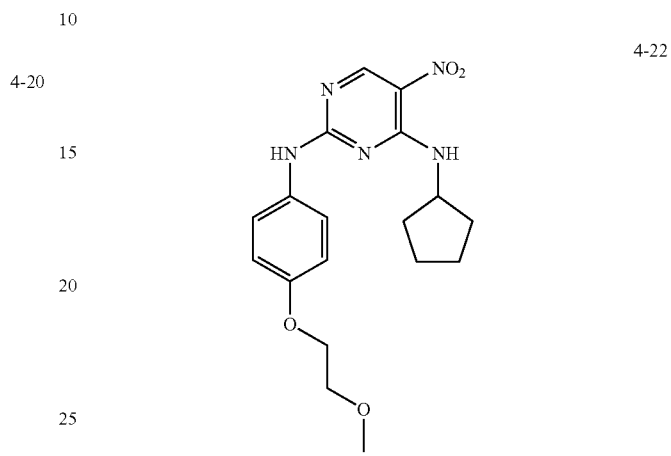

4-22

4-(2-methoxyethoxy)phenylamine (2.7 g) was added to a solution of Compound 2-5 (3.7 g) in n-butanol (80 ml). The mixture was reacted at 90° C. for 4.0 hours, cooled to room temperature, filtered, washed and dried to obtain a yellow floc-like solid (4.53 g) in a yield of 80.9%. MS m/z (ESI): 374 [M+H]⁺; ¹H NMR (400 MHz, DMSO-d₆): δ10.34 (s, 1H), 8.95 (s, 1H), 8.50 (s, 1H), 7.70 (d, J=6.0 Hz, 2H), 6.93 (d, J=8.8 Hz, 2H), 4.43 (m, 1H), 4.07 (m, 2H), 3.64 (m, 2H), 3.30 (s, 3H), 2.03 (m, 2H), 1.72 (m, 2H), 1.61 (m, 4H) ppm.

Example 34

The Preparation of 4-cyclopentylamino-2-(4-((4-ethyl piperazin-1-yl)methyl)phenylamino)-5-nitropyrimidine

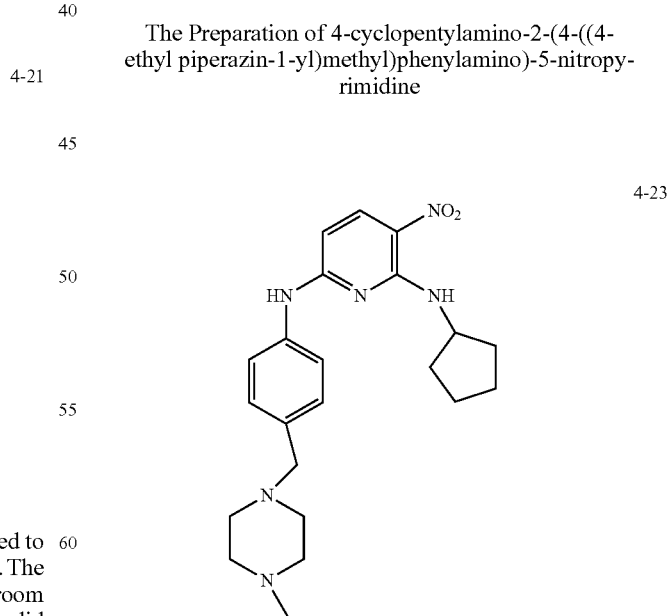

4-23

4-((4-ethylpiperazin-1-yl)methyl)phenylamine (3.6 g) was added to a solution of Compound 2-5 (6.0 g) in n-butanol (130 ml). The mixture was reacted at 90° C. for 4.0 hours, cooled

Example 35

The Preparation of 4-cyclopentylamino-2-(4-((4-methylpiperazin-1-yl)methyl)phenylamino)-5-nitropyrimidine

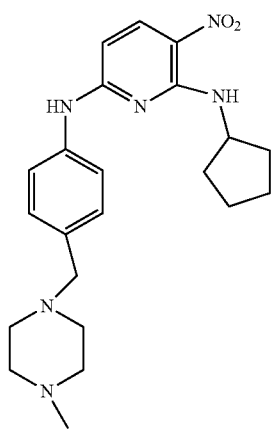

4-24

4-((4-methylpiperazin-1-yl)methyl)phenylamine (4.7 g) was added to a solution of Compound 2-5 (5.28 g) in n-butanol (130 ml). The mixture was reacted at 90° C. for 4.0 hours, cooled to room temperature, filtered, washed and dried to obtain a red solid in a yield of 85.7%. MS m/z (ESI): 412 [M+H]$^+$.

Example 36

The Preparation of 4-cyclohexylmethylamino-2-(4-(4-methylpiperazin-1-yl)phenylamino)-5-nitropyrimidine

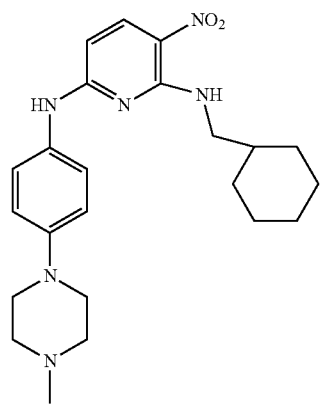

4-25

4-(4-methylpiperazinyl)phenylamine (1.13 g) was added to a solution of Compound 2-11 (1.6 g) in n-butanol (25 ml). The mixture was reacted at 90° C. for 4.0 hours, cooled to room temperature, filtered, washed and dried to obtain an orange-red solid (4.13 g) in a yield of 87.6%. MS m/z (ESI): 426 [M+H]$^+$.

Example 37

The Preparation of 4-(4-isopropylamino-5-aminopyrimidin-2-ylamino)-N-(4-methylpiperazin-1-yl)benzamide

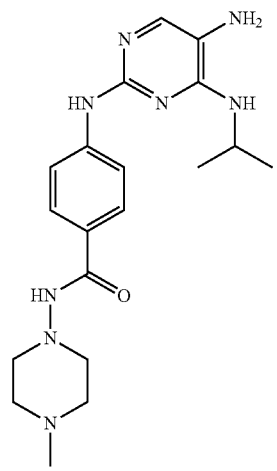

5-1

A solution of rongalite (sodium dithionite) (9.6 g) in water (30 ml) was added to a solution of 4-1 (2.1 g) in tetrahydrofuran (25 ml). The mixture was stirred at room temperature for 6-12 hours, adjusted to a pH of 7-8 by adding a saturated potassium carbonate solution, and then extracted with dichloromethane (5×20 ml). The organic phase was dried over anhydrous sodium sulfate, and rotary evaporated to dryness to obtain a jade-green solid (1.2 g) in a yield of 63.2%. $^1$H NMR (400 MHz, DMSO-d$_6$): δ 10.01 (s, 1H), 9.32 (s, 1H), 8.78 (s, 1H), 8.01 (m, 2H), 7.83 (s, 1H), 7.72 (m, 2H), 4.29 (m, 1H), 4.08 (s, 2H), 2.87 (t, J=4.8 Hz, 4H), 2.47 (br, 4H), 2.24 (s, 3H), 1.22 (d, J=6.8 Hz, 6H) ppm.

Example 38

The Preparation of 3-fluoro-4-(4-isopropylamino-5-aminopyrimidin-2-ylamino)-N-(4-methylpiperazin-1-yl)benzamide

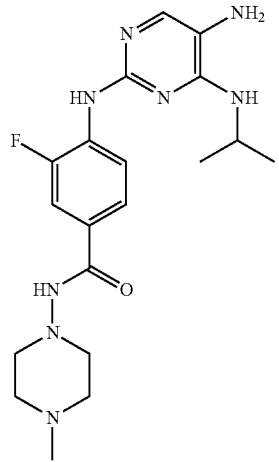

5-2

A solution of rongalite (9.6 g) in water (30 ml) was added to a solution of 4-2 (2.2 g) in tetrahydrofuran (25 ml). The mixture was stirred at room temperature for 6-12 hours, adjusted to a pH of 7-8 by adding a saturated potassium carbonate solution, and then extracted with dichloromethane (5×20 ml). The organic phase was dried over anhydrous sodium sulfate, and rotary evaporated to dryness to obtain a jade-green solid (1.4 g) in a yield of 68.4%. $^1$H NMR (400 MHz, DMSO-$d_6$): δ9.26 (s, 1H), 8.44 (m, 1H), 7.81 (s, 1H), 7.56 (d, J=10.8 Hz, 2H), 7.40 (s, 1H), 6.24 (d, J=7.2 Hz, 1H), 4.31 (s, 2H), 4.22 (m, 1H), 2.86 (t, J=4.8 Hz, 4H), 2.41 (br, 4H), 2.18 (s, 3H), 1.22 (d, J=6.4 Hz, 6H) ppm.

Example 39

The Preparation of 3-methoxy-4-(4-isopropylamino-5-aminopyrimidin-2-ylamino)-N-(4-methylpiperazin-1-yl)benzamide

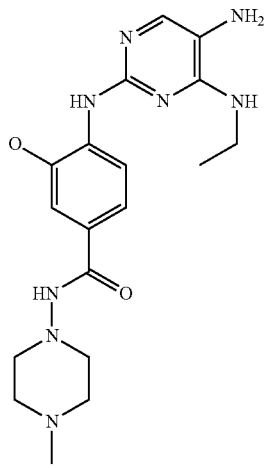

5-3

In a 500 ml round-bottom flask, Compound 4-3 (4.0 g) was dissolved into 150 ml ethanol, and then 40 ml water and 5.0 g NH$_4$Cl were added thereto. The mixture was stirred at room temperature for 10 minutes, and warmed to 90° C. 2.7 g Fe powder was added to the mixture in three portions. TLC detection indicated the completion of the reaction of the starting material. The reaction time was 3.5 hours. The mixture was filtered while hot, rotary evaporated to dryness, and subjected to a column chromatography to obtain a bluish-black solid (2.8 g) in a yield of 75.0%. MS m/z (ESI): 415 [M+H]$^+$.

Example 40

The Preparation of 4-(4-isopropylamino-5-aminopyrimidin-2-ylamino)-N-(1-methylpiperidin-4-yl)benzamide

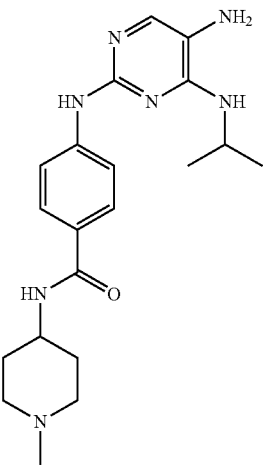

5-4

In a 500 ml round-bottom flask, Compound 4-4 (4.0 g) was dissolved into 150 ml ethanol, and then 40 ml water and 5.0 g NH$_4$Cl were added thereto. The mixture was stirred at room temperature for 10 minutes, and warmed to 90° C. 2.7 g Fe powder was added to the mixture in three portions. TLC detection indicated the completion of the reaction of the starting material. The reaction time was 4.2 hours. The mixture was filtered while hot, rotary evaporated to dryness, and subjected to a column chromatography to obtain a bluish-black solid (2.6 g) in a yield of 70.8%. MS m/z (ESI): 384 [M+H]$^+$.

Example 41

The Preparation of 4-amino-2-(4-(4-methylpiperazin-1-yl)phenylamino)-5-aminopyrimidine

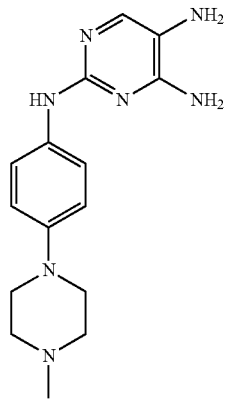

5-5

In a 500 ml round-bottom flask, Compound 4-5 (6.6 g) was dissolved into 160 ml ethanol, and then 40 ml water and 5.35 g NH$_4$Cl were added thereto. The mixture was stirred at room temperature for 10 minutes, and warmed to 90° C. 6.6 g Fe powder was added to the mixture in three portions. TLC detection indicated the completion of the reaction of the starting material. The reaction time was 4.5 hours. The mixture was filtered while hot, rotary evaporated to dryness, and recrystallized to obtain a bluish-black solid in a yield of 71.0%. $^1$H NMR (400 MHz, DMSO-$d_6$): δ 8.18 (s, 1H), 7.56 (d, J=9.2 Hz, 2H), 6.79 (d, J=8.8 Hz, 2H), 6.00 (d, J=7.6 Hz, 1H), 4.24 (m, 1H), 4.01 (s, 2H), 2.99 (t, J=4.4 Hz, 4H), 2.43 (t, J=4.8 Hz, 4H), 2.21 (s, 3H), 1.21 (d, J=6.4 Hz, 6H) ppm.

Example 42

The Preparation of 4-methylamino-2-(4-(4-methylpiperazin-1-yl)phenylamino)-5-aminopyrimidine

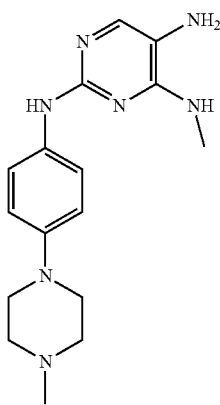

5-6

In a 100 ml round-bottom flask, Compound 4-6 (1.0 g) was dissolved into 60 ml ethanol, and then 15 ml water and 0.8 g NH$_4$Cl were added thereto. The mixture was stirred at room temperature for 10 minutes, and warmed to 90° C. 0.84 g Fe powder was added to the mixture in three portions. TLC detection indicated the completion of the reaction of the starting material. The reaction time was 1.5 hours. The mixture was filtered while hot, rotary evaporated to dryness, and subjected to a column chromatography to obtain a bluish-black solid (0.7 g) in a yield of 70.2%. MS m/z (ESI): 314 [M+H]$^+$.

Example 43

The Preparation of 4-isopropylamino-2-(4-(4-methylpiperazin-1-yl)phenylamino)-5-aminopyrimidine

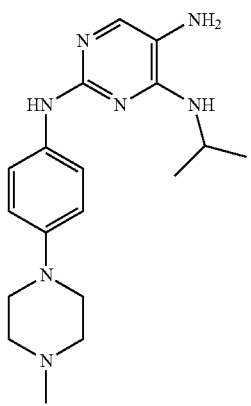

5-7

In a 500 ml round-bottom flask, Compound 4-7 (3.7 g) was dissolved into 200 ml ethanol, and then 50 ml water and 2.7 g NH$_4$Cl were added thereto. The mixture was stirred at room temperature for 10 minutes, and warmed to 90° C. 2.8 g Fe powder was added to the mixture in three portions. TLC detection indicated the completion of the reaction of the starting material. The reaction time was 3 hours. The mixture was filtered while hot, rotary evaporated to dryness, and subjected to a column chromatography to obtain a bluish-black solid (2.4 g) in a yield of 70.6%. $^1$H NMR (400 MHz, DMSO-$d_6$): δ 8.18 (s, 1H), 7.56 (d, J=9.2 Hz, 2H), 6.79 (d, J=8.8 Hz, 2H), 6.00 (d, J=7.6 Hz, 1H), 4.24 (m, 1H), 4.01 (s, 2H), 2.99 (t, J=4.4 Hz, 4H), 2.43 (t, J=4.8 Hz, 4H), 2.21 (s, 3H), 1.21 (d, J=6.4 Hz, 6H) ppm.

Example 44

The Preparation of 4-cyclopropylamino-2-(4-(4-methylpiperazin-1-yl)phenylamino)-5-aminopyrimidine

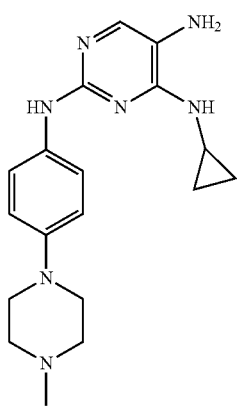

5-8

In a 100 ml round-bottom flask, Compound 4-8 (1.1 g) was dissolved into 60 ml ethanol, and then 15 ml water and 0.8 g NH$_4$Cl were added thereto. The mixture was stirred at room temperature for 10 minutes, and warmed to 90° C. 0.84 g Fe powder was added to the mixture in three portions. TLC detection indicated the completion of the reaction of the starting material. The reaction time was 1.5 hours. The mixture was filtered while hot, rotary evaporated to dryness, and subjected to a column chromatography to obtain a column chromatography to obtain bluish-black solid (0.8 g) in a yield of 79.2%. MS m/z (ESI): 340 [M+H]$^+$.

Example 45

The Preparation of 4-cyclopentylamino-2-(4-(4-methylpiperazin-1-yl)phenylamino)-5-aminopyrimidine

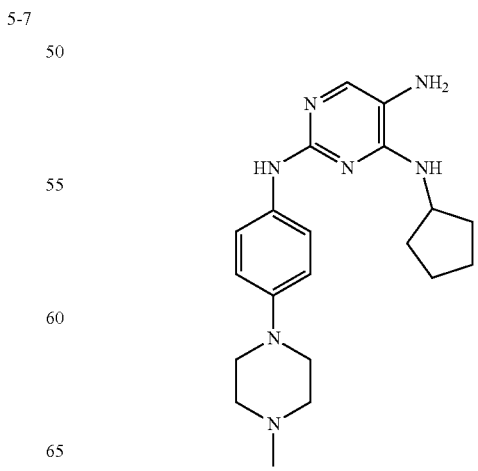

5-9

In a 250 ml round-bottom flask, Compound 4-9 (2.0 g) was dissolved into 100 ml ethanol, and then 25 ml water and 1.4 g NH₄Cl were added thereto. The mixture was stirred at room temperature for 10 minutes, and warmed to 90° C. 1.4 g Fe powder was added to the mixture in three portions. TLC detection indicated the completion of the reaction of the starting material. The reaction time was 2.5 hours. The mixture was filtered while hot, rotary evaporated to dryness, and recrystallized to obtain a bluish-black solid (1.1 g) in a yield of 59.3%. MS m/z (ESI): 368 [M+H]⁺.

Example 46

The Preparation of 4-cyclopentylamino-2-(4-(4-methylpiperazin-1-yl)phenylamino)-5-amino-6-methylpyrimidine

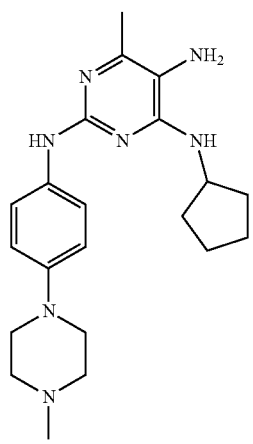

5-10

In a 500 ml round-bottom flask, Compound 4-10 (3.7 g) was dissolved into 200 ml ethanol, and then 50 ml water and 2.7 g NH₄Cl were added thereto. The mixture was stirred at room temperature for 10 minutes, and warmed to 90° C. 2.8 g Fe powder was added to the mixture in three portions. TLC detection indicated the completion of the reaction of the starting material. The reaction time was 3 hours. The mixture was filtered while hot, rotary evaporated to dryness, and subjected to a column chromatography to obtain a bluish-black solid (2.6 g) in a yield of 75.7%. MS m/z (ESI): 382 [M+H]⁺.

Example 47

The Preparation of 4-isopropylamino-2-(4-(4-methylpiperazin-1-yl)phenylamino)-5-amino-6-methoxypyrimidine

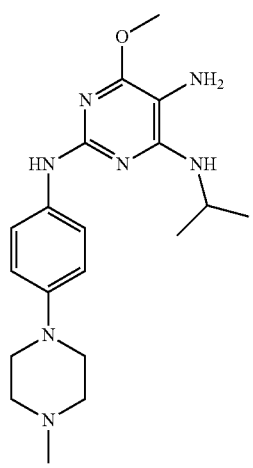

5-11

In a 500 ml round-bottom flask, Compound 4-11 (3.9 g) was dissolved into 200 ml ethanol, and then 50 ml water and 2.7 g NH₄Cl were added thereto. The mixture was stirred at room temperature for 10 minutes, and warmed to 90° C. 2.8 g Fe powder was added to the mixture in three portions. TLC detection indicated the completion of the reaction of the starting material. The reaction time was 3 hours. The mixture was filtered while hot, rotary evaporated to dryness, and subjected to a column chromatography to obtain a bluish-black solid (2.5 g) in a yield of 70.0%. MS m/z (ESI): 372 [M+H]⁺.

Example 48

The Preparation of 4-isopropylamino-2-(4-(4-methylpiperazin-1-yl)phenylamino)-5-amino-6-methylaminopyrimidine

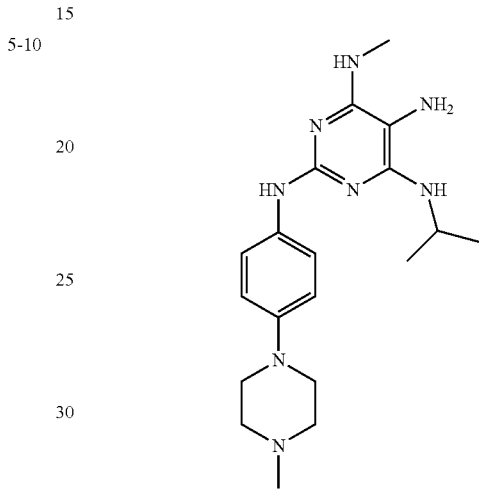

5-12

In a 500 ml round-bottom flask, Compound 4-12 (3.8 g) was dissolved into 200 ml ethanol, and then 50 ml water and 2.7 g NH₄Cl were added thereto. The mixture was stirred at room temperature for 10 minutes, and warmed to 90° C. 2.8 g Fe powder was added to the mixture in three portions. TLC detection indicated the completion of the reaction of the starting material. The reaction time was 3 hours. The mixture was filtered while hot, rotary evaporated to dryness, and subjected to a column chromatography to obtain a bluish-black solid (2.4 g) in a yield of 67.3%. MS m/z (ESI): 371 [M+H]⁺.

Example 49

The Preparation of 4-isopropylamino-2-(4-(4-methylpiperazin-1-yl)phenylamino)-5-amino-6-methylpyrimidine

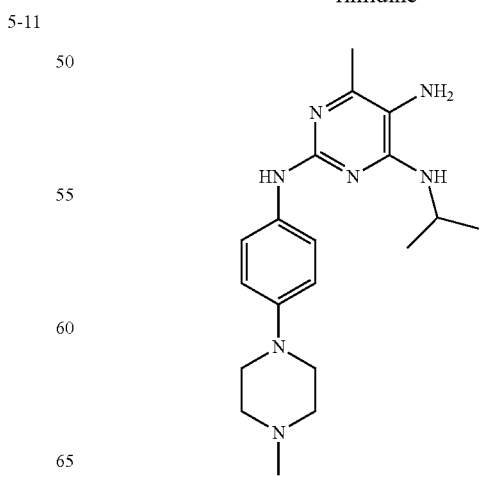

5-13

In a 500 ml round-bottom flask, Compound 4-13 (3.7 g) was dissolved into 200 ml ethanol, and then 50 ml water and 2.7 g NH$_4$Cl were added thereto. The mixture was stirred at room temperature for 10 minutes, and warmed to 90° C. 2.8 g Fe powder was added to the mixture in three portions. TLC detection indicated the completion of the reaction of the starting material. The reaction time was 3 hours. The mixture was filtered while hot, rotary evaporated to dryness, and subjected to a column chromatography to obtain a bluish-black solid (2.5 g) in a yield of 73.3%. $^1$H NMR (400 MHz, CDCl$_3$): δ 7.51 (d, J=8.8, 2H), 6.89 (d, J=8.8, 2H), 6.59 (s, 1H), 5.17 (d, J=7.2, 1H), 4.63 (s, 2H), 4.22 (m, J=6.72, 1H), 3.14 (t, J=5.0, 4H), 2.59 (t, J=4.8, 4H), 2.35 (s, 3H), 2.25 (s, 3H), 1.26 (d, J=6.4, 6H) ppm.

Example 50

The Preparation of 4-(4-cyclopentylamino-5-aminopyrimidin-2-ylamino)-N-(4-methylpiperazin-1-yl)benzamide

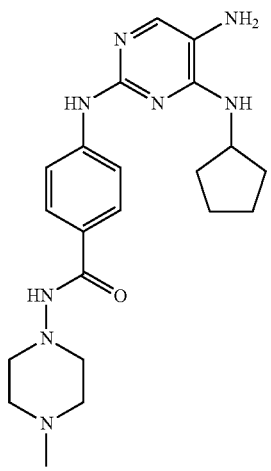

5-14

In a 500 ml round-bottom flask, Compound 4-14 (4.4 g) was dissolved into 150 ml ethanol, and then 40 ml water and 5.0 g NH$_4$Cl were added thereto. The mixture was stirred at room temperature for 10 minutes, and warmed to 90° C. 2.7 g Fe powder was added to the mixture in three portions. TLC detection indicated the completion of the reaction of the starting material. The reaction time was 3.5 hours. The mixture was filtered while hot, rotary evaporated to dryness, and recrystallized to obtain a bluish-black solid (3.2 g) in a yield of 77.9%. MS m/z (ESI): 411 [M+H]$^+$.

Example 51

The Preparation of 4-(4-isopropylamino-5-aminopyrimidin-2-ylamino)-N-(1-methylpiperidin-4-yl)benzamide

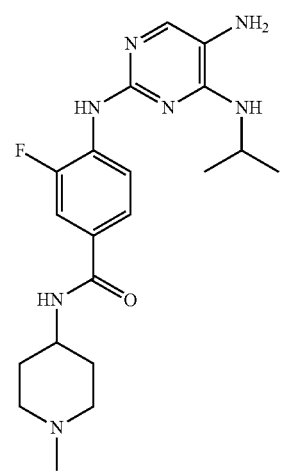

5-15

A solution of rongalite (9.6 g) in water (30 ml) was added to a solution of 4-15 (2.2 g) in tetrahydrofuran (25 ml). The mixture was stirred at room temperature for 6-12 hours, adjusted to a pH of 7-8 by adding a saturated potassium carbonate solution, and then extracted with dichloromethane (5×20 ml). The organic phase was dried over anhydrous sodium sulfate, and rotary evaporated to dryness to obtain a jade-green solid (1.5 g) in a yield of 69.6%. MS m/z (ESI): 402 [M+H]$^+$.

Example 52

The Preparation of N-(3-(4-isopropylamino-5-nitropyrimidin-2-ylamino)phenyl)acrylamide

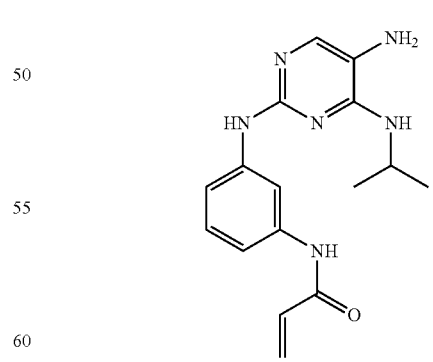

5-16

N-(3-aminophenyl)acrylamide (3.2 g) was added to a solution of Compound 2-3 (4.3 g) in n-butanol (150 ml). The mixture was reacted at 90° C. for 3 hours, cooled to room temperature, filtered, washed and dried to obtain a red solid (6.0 g) in a yield of 88.3%. MS m/z (ESI): 344 [M+H]$^+$.

Example 53

The Preparation of 4-isopropylamino-2-(4-(2-morpholinoethoxy)phenylamino)-5-aminopyrimidine

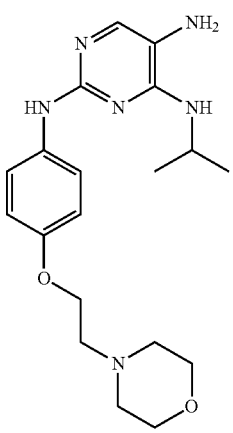

5-17

In a 100 ml round-bottom flask, Compound 4-17 (1.21 g) was dissolved into 60 ml ethanol, and then 15 ml water and 0.8 g NH$_4$Cl were added thereto. The mixture was stirred at room temperature for 10 minutes, and warmed to 90° C. 0.84 g Fe powder was added to the mixture in three portions. TLC detection indicated the completion of the reaction of the starting material. The reaction time was 1.5 hours. The mixture was filtered while hot, rotary evaporated to dryness, and subjected to a column chromatography to obtain a bluish-black solid in a yield of 75.2%. MS m/z (ESI): 373 [M+H]$^+$.

Example 54

The Preparation of 4-isopropylamino-2-(4-(3-(4-methylpiperazin-1-yl)propylamino)phenylamino)-5-aminopyrimidine

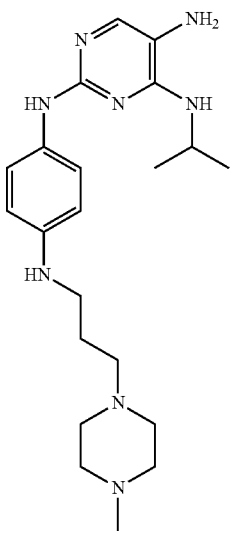

5-18

In a 100 ml round-bottom flask, Compound 4-18 (1.3 g) was dissolved into 60 ml ethanol, and then 15 ml water and 0.8 g NH$_4$Cl were added thereto. The mixture was stirred at room temperature for 10 minutes, and warmed to 90° C. 0.84 g Fe powder was added to the mixture in three portions. TLC detection indicated the completion of the reaction of the starting material. The reaction time was 1.5 hours. The mixture was filtered while hot, rotary evaporated to dryness, and subjected to a column chromatography to obtain a bluish-black solid in a yield of 78.9%. MS m/z (ESI): 399 [M+H]$^+$.

Example 55

The Preparation of 4-isopropylamino-2-(4-morpholinophenylamino)-5-aminopyrimidine

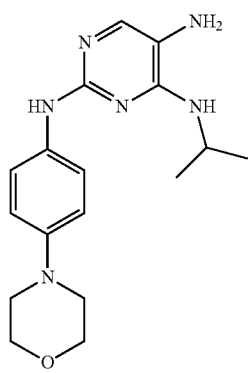

5-19

In a 100 ml round-bottom flask, Compound 4-19 (1.1 g) was dissolved into 60 ml ethanol, and then 15 ml water and 0.8 g NH$_4$Cl were added thereto. The mixture was stirred at room temperature for 10 minutes, and warmed to 90° C. 0.84 g Fe powder was added to the mixture in three portions. TLC detection indicated the completion of the reaction of the starting material. The reaction time was 2.5 hours. The mixture was filtered while hot, rotary evaporated to dryness, and subjected to a column chromatography to obtain a bluish-black solid in a yield of 74.1%. MS m/z (ESI): 329 [M+H]$^+$.

Example 56

The Preparation of 4-cyclopentylamino-2-(4-(4-morpholinylmethyl)phenylamino)-5-aminopyrimidine

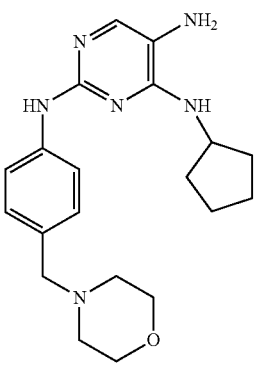

5-20

In a 500 ml round-bottom flask, Compound 4-20 (3.85 g) was dissolved into 150 ml ethanol, and then 40 ml water and 5.0 g NH₄Cl were added thereto. The mixture was stirred at room temperature for 10 minutes, and warmed to 90° C. 2.7 g Fe powder was added to the mixture in three portions. TLC detection indicated the completion of the reaction of the starting material. The reaction time was 3.5 hours. The mixture was filtered while hot, rotary evaporated to dryness, and subjected to a column chromatography to obtain a bluish-black solid in a yield of 74.5%. MS m/z (ESI): 369 [M+H]⁺.

Example 57

The Preparation of 4-cyclohexylamino-2-(4-(4-methylpiperazin-1-yl)phenylamino)-5-aminopyrimidine

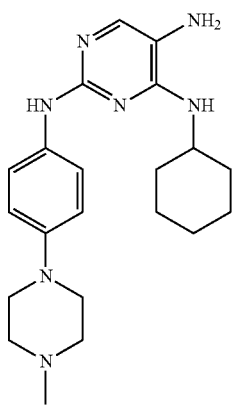

5-21

In a 100 ml round-bottom flask, Compound 4-21 (1.03 g) was dissolved into 40 ml ethanol, and then 10 ml water and 0.67 g NH₄Cl were added thereto. The mixture was stirred at room temperature for 10 minutes, and warmed to 90° C. 0.7 g Fe powder was added to the mixture in three portions. TLC detection indicated the completion of the reaction of the starting material. The reaction time was 3.7 hours. The mixture was filtered while hot, and rotary-evaporated to dryness to obtain a crude product in a yield of 78.9%. MS m/z (ESI): 382 [M+H]⁺.

Example 58

The Preparation of 4-cyclopentylamino-2-(4-(2-methoxyethoxy)phenylamino)-5-aminopyrimidine

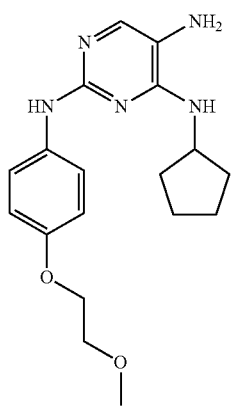

5-22

In a 250 ml round-bottom flask, Compound 4-22 (3.73 g) was dissolved into 120 ml ethanol, and then 30 ml water and 2.67 g NH₄Cl were added thereto. The mixture was stirred at room temperature for 10 minutes, and warmed to 90° C. 2.8 g Fe powder was added to the mixture in three portions. TLC detection indicated the completion of the reaction of the starting material. The reaction time was 4 hours. The mixture was filtered while hot, and rotary-evaporated to dryness to obtain a crude product in a yield of 84.6%. MS m/z (ESI): 344 [M+H]⁺.

Example 59

The Preparation of 4-cyclopentylamino-2-(4-((4-ethyl piperazin-1-yl)methyl)phenylamino)-5-aminopyrimidine

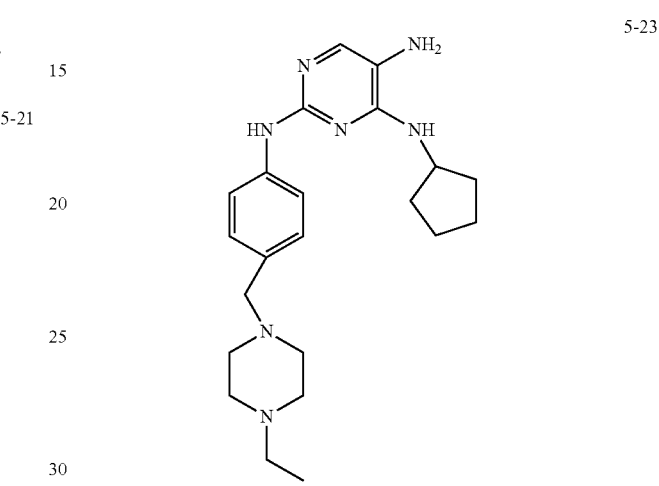

5-23

In a 500 ml round-bottom flask, Compound 4-23 (10 g) was dissolved into 240 ml ethanol, and then 60 ml water and 2.67 g NH₄Cl were added thereto. The mixture was stirred at room temperature for 10 minutes, and warmed to 90° C. 6.6 g Fe powder was added to the mixture in three portions. TLC detection indicated the completion of the reaction of the starting material. The reaction time was 4 hours. The mixture was filtered while hot, and rotary-evaporated to dryness to obtain a crude product in a yield of 82.7%. MS m/z (ESI): 396 [M+H]⁺.

Example 60

The Preparation of 4-cyclopentylamino-2-(4-((4-methyl piperazin-1-yl)methyl)phenylamino)-5-aminopyrimidine

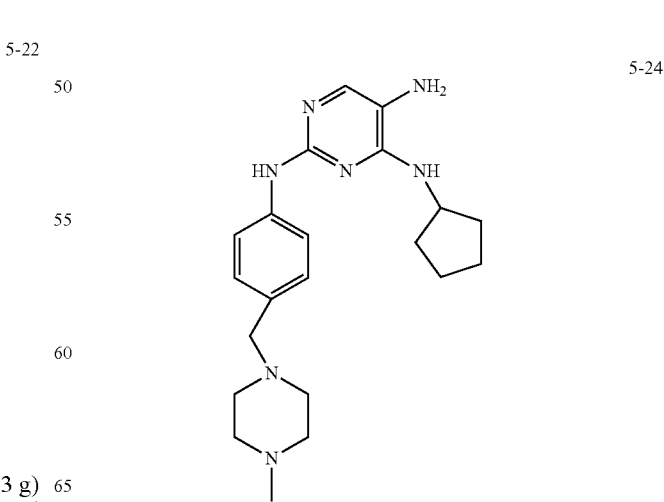

5-24

In a 500 ml round-bottom flask, Compound 4-24 (9.42 g) was dissolved into 240 ml ethanol, and then 60 ml water and 1.92 g NH₄Cl were added thereto. The mixture was stirred at room temperature for 10 minutes, and warmed to 90° C. 6.85 g Fe powder was added to the mixture in three portions. TLC detection indicated the completion of the reaction of the starting material. The reaction time was 4 hours. The mixture was filtered while hot, and rotary-evaporated to dryness to obtain a crude product in a yield of 80.6%. MS m/z (ESI): 382 [M+H]⁺.

Example 61

The Preparation of 4-cyclohexylmethylamino-2-(4-(4-methylpiperazin-1-yl)phenylamino)-5-aminopyrimidine

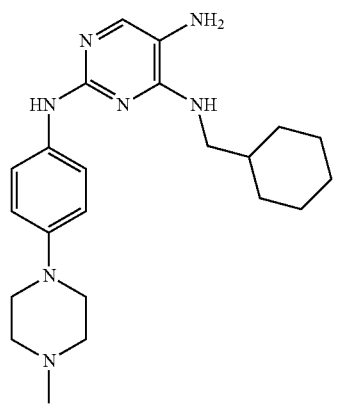

5-25

In a 100 ml round-bottom flask, Compound 4-23 (2.0 g) was dissolved into 30 ml ethanol, and then 10 ml water and 0.62 g NH₄Cl were added thereto. The mixture was stirred at room temperature for 10 minutes, and warmed to 90° C. 1.29 g Fe powder was added to the mixture in three portions. TLC detection indicated the completion of the reaction of the starting material. The mixture was filtered while hot, and rotary-evaporated to dryness to obtain a crude product in a yield of 81.4%. MS m/z (ESI): 396 [M+H]⁺.

Example 62

The Preparation of 4-(9-isopropyl-8-phenylamino-9H-purin-2-ylamino)-N-(4-methylpiperidin-1-yl)benzamide

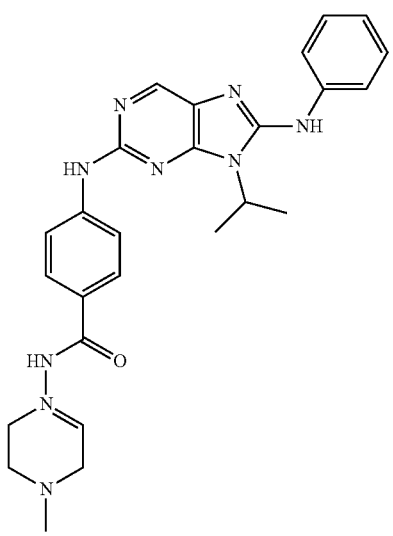

8-1

Compound 5-1 (2.3 g) was dissolved into dichloromethane (90 ml). To the mixture were successively added EDCI (2.3 g), N,N-diisopropylethylamine (4.9 ml), and phenyl isothiocyanate (0.9 ml). The mixture was stirred at room temperature for half an hour, and refluxed for 10 hours. TLC detection indicated the completion of the reaction of the starting material 5-1. After cooling the mixture, purification was conducted by a column chromatography to obtain a pale red solid in a yield of 64.3%. ESI-MS (m/z, %) 484.29 (M−H)⁻; ¹H NMR (400 MHz, DMSO-d₆): δ9.63 (s, 1H), 9.21 (s, 1H), 9.11 (s, 1H), 7.85 (m, 4H), 7.73 (d, J=8.4 Hz, 2H), 7.34 (m, 2H), 7.00 (m, 1H), 4.94 (m, 1H), 2.88 (t, J=4.4 Hz, 4H), 2.42 (br, 4H), 2.19 (s, 3H), 1.70 (d, J=6.8 Hz, 6H) ppm.

Example 63

The Preparation of 4-(8-(3-chloro-4-fluorophenylamino)-9-isopropyl-9H-purin-2-ylamino)-N-(4-methylpiperidin-1-yl)benzamide

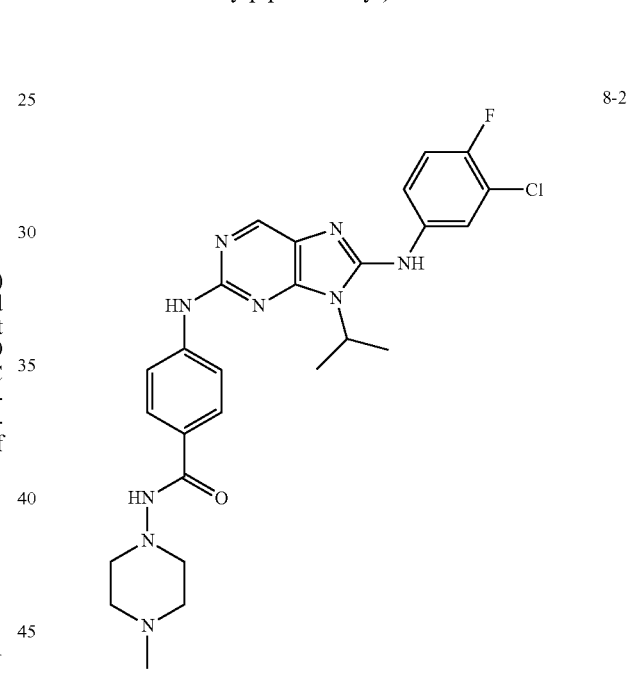

8-2

Compound 5-1 (2.3 g) was dissolved into dichloromethane (90 ml). To the mixture were successively added EDCI (2.3 g), N,N-diisopropylethylamine (4.9 ml), and 3-chloro-4-fluorophenyl isothiocyanate (1.35 g). The mixture was stirred at room temperature for half an hour, and refluxed for 10 hours. TLC detection indicated the completion of the reaction of the starting material 5-1. After cooling the mixture, purification was conducted by a column chromatography to obtain a pale red solid in a yield of 62.9%. ESI-MS (m/z, %) 536.27 (M−H)⁻. ¹H NMR (400 MHz, DMSO-d₆): δ 9.65 (s, 1H), 9.31 (s, 1H), 9.20 (s, 1H), 8.51 (s, 1H), 8.23 (m, 1H), 7.86 (d, J=8.8 Hz, 2H), 7.78 (m, 1H), 7.75 (t, J=6.6 Hz, 2H), 7.41 (t, J=9.2 Hz, 1H), 4.90 (s, 1H), 2.88 (d, J=4 Hz, 4H), 2.43 (m, 4H), 2.20 (s, 3H), 1.70 (d, J=6.8 Hz, 6H) ppm.

Example 64

The Preparation of 4-(8-(3-acetamidophenylamino)-9-isopropyl-9H-purin-2-ylamino)-N-(4-methylpiperidin-1-yl)benzamide

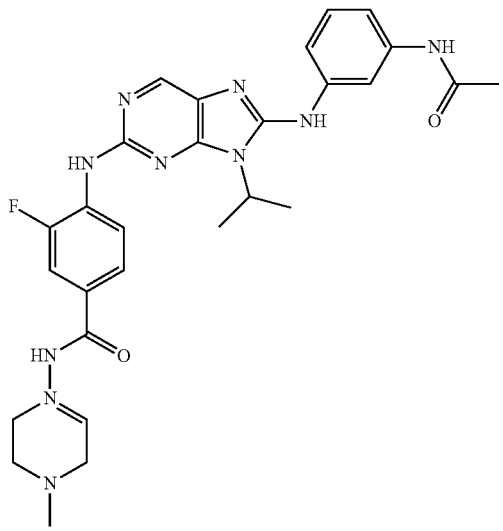

8-3

Compound 5-2 (2.4 g) was dissolved into dichloromethane (90 ml). To the mixture were successively added EDCI (2.3 g), N,N-diisopropylethylamine (4.9 ml), and meta-acetamidophenyl isothiocyanate (1.4 g). The mixture was stirred at room temperature for half an hour, and refluxed for 10 hours. TLC detection indicated the completion of the reaction of the starting material 5-2. After cooling the mixture, purification was conducted by a column chromatography to obtain a pale red solid in a yield of 69.1%. ESI-MS (m/z, %) 561.18 (M–H)⁻. ¹H NMR (400 MHz, DMSO-d$_6$): δ 10.00 (s, 1H), 9.52 (s, 1H), 9.20 (s, 1H), 8.88 (s, 1H), 8.42 (s, 1H), 8.26 (m, 1H), 8.08 (s, 1H), 7.66 (d, J=10.0 Hz, 2H), 7.57 (d, J=7.2 Hz, 1H), 7.21 (m, 2H), 4.94 (m, 1H), 2.90 (s, 4H), 2.68 (br, 4H), 2.06 (s, 3H), 1.64 (d, J=6.0 Hz, 6H) ppm.

Example 65

The Preparation of 3-fluoro-4-(9-isopropyl-8-phenylamino-9H-purin-2-ylamino)-N-(4-methylpiperazin-1-yl)benzamide 8-4

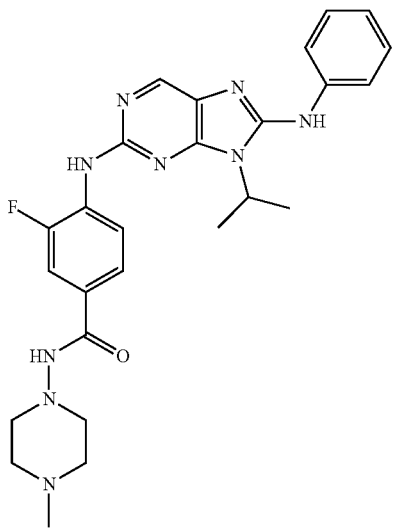

Compound 5-2 (2.4 g) was dissolved into dichloromethane (90 ml). To the mixture were successively added EDCI (2.3 g), N,N-diisopropylethylamine (4.9 ml), and phenyl isothiocyanate (0.9 ml). The mixture was stirred at room temperature for half an hour, and refluxed for 10 hours. TLC detection indicated the completion of the reaction of the starting material 5-2. After cooling the mixture, purification was conducted by a column chromatography to obtain a pale red solid in a yield of 64.8%. ESI-MS (m/z, %) 502.17 (M–H)⁻. ¹H NMR (400 MHz, DMSO-d$_6$): δ 9.37 (s, 1H), 9.10 (s, 1H), 8.88 (s, 1H), 8.43 (s, 1H), 8.25 (m, 1H), 7.84 (d, J=8.4 Hz, 2H), 7.64 (d, J=10.4 Hz, 2H), 7.00 (m, 2H), 4.90 (m, 1H), 2.89 (s, 4H), 2.42 (br, 4H), 2.19 (s, 3H), 1.65 (d, J=6.4 Hz, 6H) ppm.

Example 66

The Preparation of 3-fluoro-4-(9-isopropyl-8-(3-chloro-4-fluorophenylamino)-9H-purin-2-ylamino)-N-(4-methylpiperazin-1-yl)benzamide

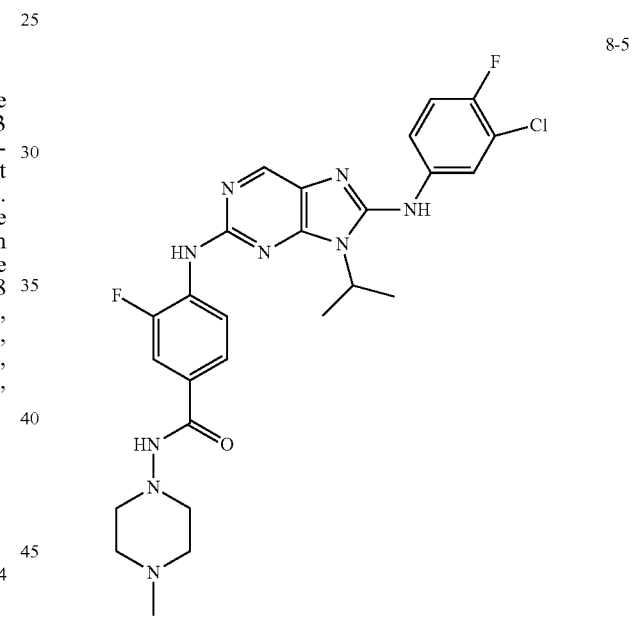

8-5

Compound 5-2 (2.4 g) was dissolved into dichloromethane (90 ml). To the mixture were successively added EDCI (2.3 g), N,N-diisopropylethylamine (4.9 ml), and 3-chloro-4-fluorophenyl isothiocyanate (1.35 g). The mixture was stirred at room temperature for half an hour, and refluxed for 10 hours. TLC detection indicated the completion of the reaction of the starting material 5-2. After cooling the mixture, purification was conducted by a column chromatography to obtain a pale red solid in a yield of 68.8%. ESI-MS (m/z, %) 554.30 (M–H)⁻. ¹H NMR (400 MHz, DMSO-d6): δ9.21 (s, 1H), 9.04 (s, 1H), 8.41 (s, 1H), 8.22 (d, J=5.2 Hz, 1H), 7.74 (m, 1H), 7.62 (d, J=8.8 Hz, 1H), 7.57 (d, J=8.8 Hz, 1H), 7.39 (m, 1H), 6.87 (d, J=8.4 Hz, 2H), 4.84 (m, 1H), 3.05 (s, 4H), 2.45 (br, 4H), 2.22 (s, 3H), 1.66 (d, J=6.4 Hz, 6H) ppm.

Example 67

The Preparation of 3-fluoro-4-(9-isopropyl-8-phenylamino-9H-purin-2-ylamino)-N-(4-methylpiperazin-1-yl)benzamide

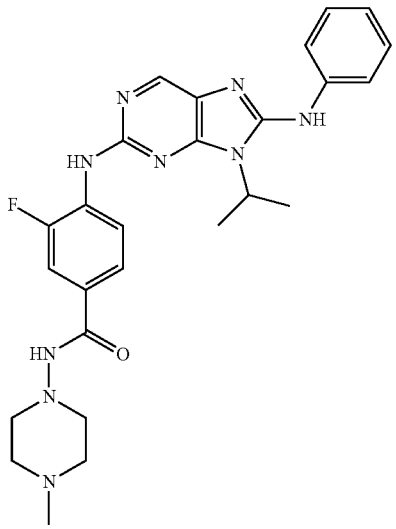

8-6

Compound 5-15 (2.4 g) was dissolved into dichloromethane (90 ml). To the mixture were successively added EDCI (2.3 g), N,N-diisopropylethylamine (4.9 ml), and phenyl isothiocyanate (0.9 ml). The mixture was stirred at room temperature for half an hour, and refluxed for 10 hours. TLC detection indicated the completion of the reaction of the starting material 5-15. After cooling the mixture, purification was conducted by a column chromatography to obtain a pale red solid in a yield of 67.6%. ESI-MS (m/z, %) 502.22 (M–H)$^-$. $^1$H NMR (400 MHz, DMSO-d$_6$): δ 9.22 (s, 1H), 8.87 (s, 1H), 8.49 (s, 1H), 8.44 (s, 1H), 8.29 (t, J=8.4, 1H), 7.86 (d, J=8.0, 2H), 7.78 (d, J=8.8, 2H), 7.34 (t, J=7.6, 2H), 7.01 (t, J=7.2, 1H), 4.97 (m, 1H), 4.04 (m, 1H), 3.38 (m, 2H), 3.09 (m, 2H), 2.72 (s, 3H), 1.99 (m, 4H), 1.65 (d, J=6.8, 6H) ppm.

Example 68

The Preparation of 3-methoxy-4-(9-isopropyl-8-phenylamino-9H-purin-2-ylamino)-N-(4-methylpiperazin-1-yl)benzamide 8-7

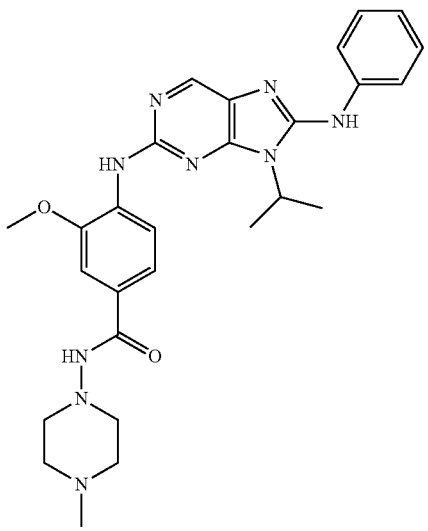

Compound 5-3 (2.5 g) was dissolved into dichloromethane (90 ml). To the mixture were successively added EDCI (2.3 g), N,N-diisopropylethylamine (4.9 ml), and phenyl isothiocyanate (0.9 ml). The mixture was stirred at room temperature for half an hour, and refluxed for 10 hours. TLC detection indicated the completion of the reaction of the starting material 5-3. After cooling the mixture, purification was conducted by a column chromatography to obtain a pale red solid in a yield of 66.5%. ESI-MS (m/z, %) 514.21 (M–H)$^-$. $^1$H NMR (400 MHz, DMSO-d$_6$): δ 10.98 (s, 1H), 9.65 (s, 1H), 8.90 (s, 1H), 8.50 (s, 1H), 8.27 (d, J=7.6 Hz, 1H), 7.83 (d, J=7.6 Hz, 2H), 7.39 (t, J=8 Hz, 2H), 7.18-7.08 (m, 3H), 5.026 (m, 1H), 3.94 (s, 4H), 3.42 (d, J=7.6 Hz, 2H), 3.09 (d, J=12 Hz, 2H), 2.79 (d, J=7.2 Hz, 3H), 1.66 (d, J=6.4 Hz, 6H) ppm.

Example 69

The Preparation of 4-(8-(3-chloro-4-fluorophenylamino)-9-isopropyl-9H-purin-2-ylamino)-3-methoxy-N-(1-methylpiperidin-4-yl)benzamide

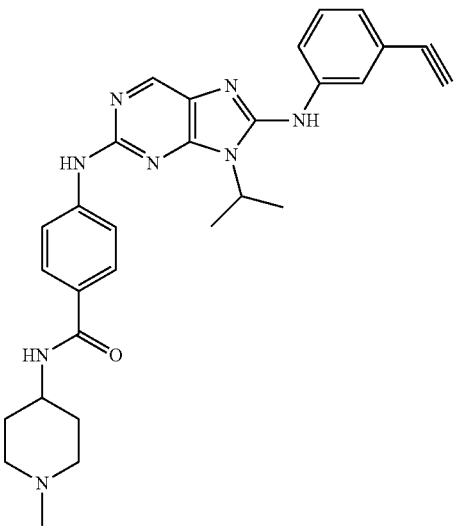

8-8

To a solution of Compound 5-4 (2.0 g) and methyl 3-ethynylphenylcarbamodithioate (1.3 g) in N,N-dimethylformamide (30 ml) were added copper oxide (0.08 g) and potassium carbonate (1.4 g). The mixture was heated to 60° C. and reacted for 2-6 hours. The reaction solution was cooled to room temperature and filtered. The filtrate was washed with ethyl acetate, a saturated saline solution and water. The organic layer was dried over anhydrous sodium sulfate and concentrated. Purification was conducted by a column chromatography to obtain an off-white solid in a yield of 64.1%. ESI-MS (m/z, %) 507.22 (M–H)$^-$. $^1$H NMR (400 MHz, DMSO-d6): δ 9.51 (s, 1H), 9.04 (s, 1H), 8.91 (s, 1H), 7.88 (m, 4H), 7.65 (d, 2H), 7.41 (m, 2H), 7.12 (m, 1H), 4.80 (m, 1H), 4.14 (s, 1H), 3.71 (m, 1H), 2.80 (m, 4H), 2.39 (br, 4H), 2.21 (s, 3H), 1.62 (d, 6H) ppm.

Example 70

The Preparation of 4-(8-phenylamino-9-isopropyl-9H-purin-2-ylamino)-N-(1-methylpiperidin-4-yl)benzamide

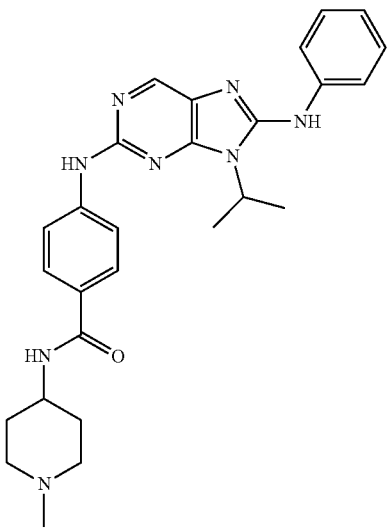

8-9

Compound 5-4 (2.3 g) was dissolved into dichloromethane (90 ml). To the mixture were successively added EDCI (2.3 g), N,N-diisopropylethylamine (4.9 ml), and phenyl isothiocyanate (0.9 ml). The mixture was stirred at room temperature for half an hour, and refluxed for 10 hours. TLC detection indicated the completion of the reaction of the starting material 5-4. After cooling the mixture, purification was conducted by a column chromatography to obtain a pale red solid in a yield of 67.9%. ESI-MS (m/z, %) 483.25 (M–H)$^-$. $^1$H NMR (400 MHz, DMSO-d$_6$): δ 9.72 (s, 1H), 9.63 (s, 1H), 9.11 (s, 1H), 8.45 (s, 1H), 8.28 (s, 1H), 7.89-7.81 (m, 5H), 7.34 (t, J=7.8 Hz, 2H), 7.00 (t, J=7.2 Hz, 1H), 4.95 (m, 1H), 4.02 (s, 1H), 3.44 (d, J=10.8 Hz, 2H), 3.08 (s, 2H), 2.75 (s, 3H), 1.99 (s, 2H), 1.82 (d, J=11.2 Hz, 2H), 1.70 (d, J=6.8 Hz, 6H) ppm.

Example 71

The Preparation of 9-isopropyl-2-(4-(4-methylpiperazin-1-yl)phenylamino)-8-phenylamino-9H-purine

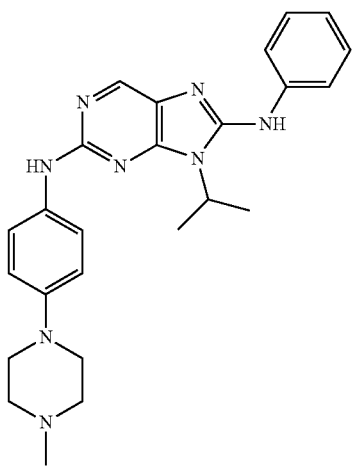

8-10

Compound 5-7 (2.05 g) was dissolved into dichloromethane (90 ml). To the mixture were successively added EDCI (2.3 g), N,N-diisopropylethylamine (4.9 ml), and phenyl isothiocyanate (0.9 ml). The mixture was stirred at room temperature for half an hour, and refluxed for 10 hours. TLC detection indicated the completion of the reaction of the starting material 5-7. After cooling the mixture, purification was conducted by a column chromatography to obtain a pale red solid in a yield of 67.5%. ESI-MS (m/z, %) 441.29 (M–H)$^-$. $^1$H NMR (400 MHz, DMSO-d6): δ 9.09 (d, J=6.8 Hz, 2H), 8.36 (s, 1H), 7.83 (d, J=8.0 Hz, 2H), 7.69 (d, J=9.2 Hz, 2H), 7.33 (m, 2H), 6.97 (m, 3H), 4.92 (m, 1H), 3.44 (br, 4H), 3.17 (br, 4H), 2.81 (s, 3H), 1.67 (d, J=6.8 Hz, 6H) ppm.

Example 72

The Preparation of 8-(3-bromophenylamino)-9-isopropyl-2-(4-(4-methylpiperazin-1-yl)phenylamino)-9H-purine

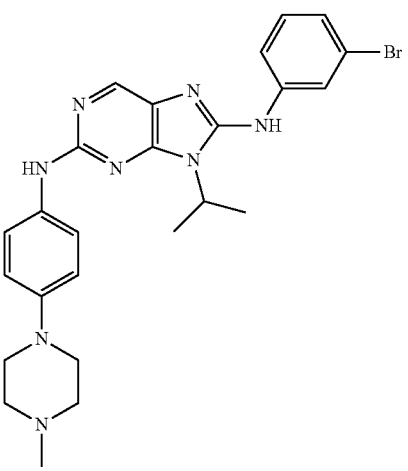

8-11

Compound 5-7 (2.05 g) was dissolved into dichloromethane (90 ml). To the mixture were successively added EDCI (2.3 g), N,N-diisopropylethylamine (4.9 ml), and meta-bromophenyl isothiocyanate (1.5 g). The mixture was stirred at room temperature for half an hour, and refluxed for 10 hours. TLC detection indicated the completion of the reaction of the starting material 5-7. After cooling the mixture, purification was conducted by a column chromatography to obtain a pale red solid in a yield of 57.4%. ESI-MS (m/z, %) 519.19 (M–H)$^-$. $^1$H NMR (400 MHz, DMSO-d$_6$): δ 9.47 (s, 1H), 9.09 (s, 1H), 8.42 (s, 1H), 8.25 (s, 1H), 7.85 (d, J=8.0 Hz, 1H), 7.67 (d, J=8.8 Hz, 2H), 7.28 (t, J=8.4 Hz, 1H), 7.14 (d, J=8.0 Hz, 1H), 6.93 (d, J=8.8 Hz, 2H), 4.99 (m, 1H), 3.51-3.40 (m, 2H), 3.25 (s, 2H), 3.07 (s, 4H), 2.64 (s, 3H), 1.66 (d, J=6.8; H, 6H) ppm.

Example 73

The Preparation of 8-(3-ethynylphenylamino)-9-isopropyl-2-(4-(4-methylpiperazin-1-yl)phenylamino)-9H-purine

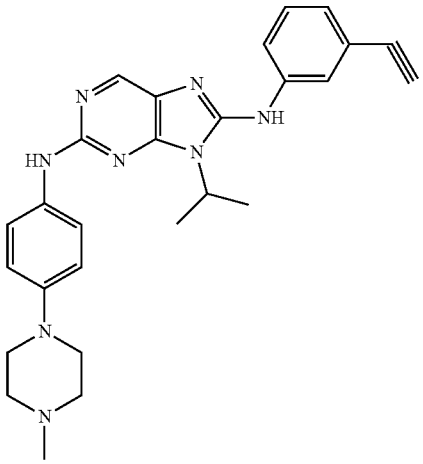

8-12

Compound 5-7 (2.05 g) was dissolved into dichloromethane (90 ml). To the mixture were successively added EDCI (2.3 g), N,N-diisopropylethylamine (4.9 ml), and meta-ethynylphenyl isothiocyanate (1.1 g). The mixture was stirred at room temperature for half an hour, and refluxed for 10 hours. TLC detection indicated the completion of the reaction of the starting material 5-7. After cooling the mixture, purification was conducted by a column chromatography to obtain a pale red solid in a yield of 53.9%. ESI-MS (m/z, %) 465.23 (M−H)⁻. ¹H NMR (400 MHz, DMSO-d₆): δ 9.10 (s, 1H), 9.02 (s, 1H), 8.41 (s, 1H), 8.07 (s, 1H), 7.81 (d, J=8.4 Hz, 1H), 7.64 (d, J=9.2 Hz, 2H), 7.34 (t, J=8.0, 1H), 7.08 (d, J=7.2 Hz, 1H), 6.88 (d, J=9.2 Hz, 2H), 4.85 (m, 1H), 4.18 (s, 1H), 3.05 (s, 4H), 2.47 (t, J=9.0, 4H), 2.22 (s, 3H), 1.67 (d, J=6.8 Hz, 6H) ppm.

Example 74

The Preparation of 8-(3-chloro-4-fluorophenylamino)-9-isopropyl-2-(4-(4-methylpiperazin-1-yl)phenylamino)-9H-purine

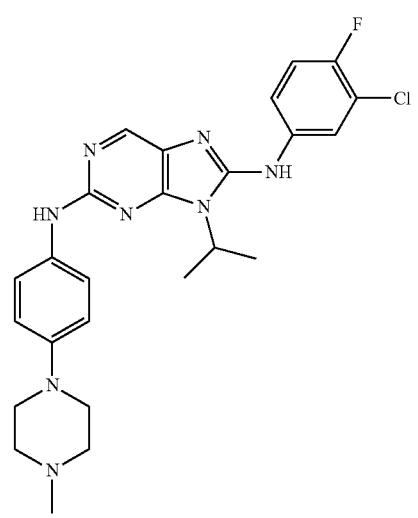

8-13

Compound 5-7 (2.05 g) was dissolved into dichloromethane (90 ml). To the mixture were successively added EDCI (2.3 g), N,N-diisopropylethylamine (4.9 ml), and 3-chloro-4-fluorophenyl isothiocyanate (1.35 g). The mixture was stirred at room temperature for half an hour, and refluxed for 10 hours. TLC detection indicated the completion of the reaction of the starting material 5-7. After cooling the mixture, purification was conducted by a column chromatography to obtain a pale red solid in a yield of 60.8%. ESI-MS (m/z, %) 493.16 (M−H)⁻. ¹H NMR (400 MHz, DMSO-d6): δ 9.21 (s, 1H), 9.04 (s, 1H), 8.41 (s, 1H), 8.22 (d, J=5.2 Hz, 1H), 7.74 (m, 1H), 7.62 (d, J=8.8 Hz, 1H), 7.57 (d, J=8.8 Hz, 1H), 7.39 (m, 1H), 6.87 (d, J=8.4 Hz, 2H), 4.84 (m, 1H), 3.05 (br, 4H), 2.45 (br, 4H), 2.22 (s, 3H), 1.66 (d, J=6.4 Hz, 6H) ppm.

Example 75

The Preparation of 8-(3-bromophenylamino)-9-cyclopropyl-2-(4-(4-methylpiperazin-1-yl)phenylamino)-9H-purine

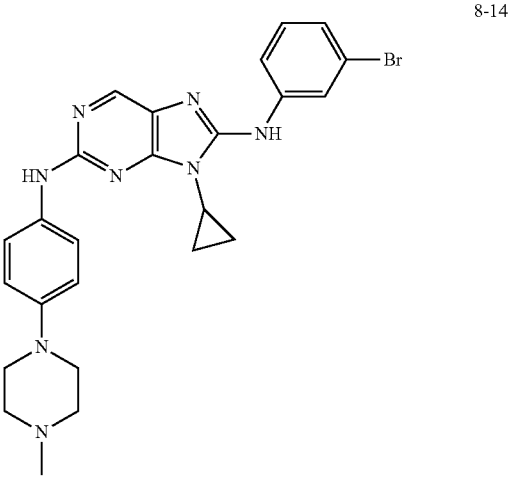 [SMILES: CN1CCN(c2ccc(Nc3ncc4nc(Nc5cccc(Br)c5)n(C5CC5)c4n3)cc2)CC1]

8-14

Compound 5-8 (2.05 g) was dissolved into dichloromethane (90 ml). To the mixture were successively added EDCI (2.3 g), N,N-diisopropylethylamine (4.9 ml), and meta-bromophenyl isothiocyanate (1.5 g). The mixture was stirred at room temperature for half an hour, and refluxed for 10 hours. TLC detection indicated the completion of the reaction of the starting material 5-8. After cooling the mixture, purification was conducted by a column chromatography to obtain a pale red solid in a yield of 58.2%. ESI-MS (m/z, %) 517.21 (M−H)⁻. ¹H NMR (400 MHz, DMSO-d6): δ 9.78 (s, 1H), 9.32 (s, 1H), 8.45 (s, 1H), 7.79 (m, 2H), 7.61 (m, 2H), 7.49 (m, 2H), 7.36 (m, 1H), 4.15 (m, 1H), 2.94 (tr, 4H), 2.63 (br, 4H), 2.19 (s, 3H), 1.26 (m, 4H) ppm.

Example 76

The Preparation of 8-(4-bromophenylamino)-9-isopropyl-2-(4-(4-methylpiperazin-1-yl)phenylamino)-9H-purine

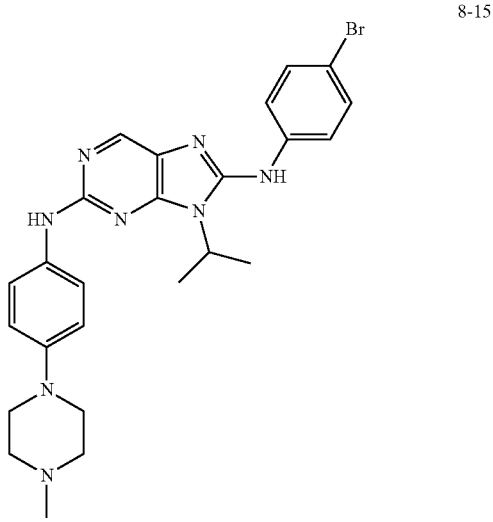 [SMILES: CC(C)n1c(Nc2ccc(Br)cc2)nc2cnc(Nc3ccc(N4CCN(C)CC4)cc3)nc21]

8-15

Compound 5-7 (2.05 g) was dissolved into dichloromethane (90 ml). To the mixture were successively added EDCI (2.3 g), N,N-diisopropylethylamine (4.9 ml), and para-bromophenyl isothiocyanate (1.5 g). The mixture was stirred at room temperature for half an hour, and refluxed for 10 hours. TLC detection indicated the completion of the reaction of the starting material 5-7. After cooling the mixture, purification was conducted by a column chromatography to obtain a pale red solid in a yield of 53.4%. ESI-MS (m/z, %) 519.22 (M−H)⁻. ¹H NMR (400 MHz, DMSO-d$_6$): δ 9.25 (s, 1H), 9.11 (s, 1H), 8.39 (s, 1H), 7.85 (d, J=8.8 Hz, 2H), 7.69 (d, J=9.2 Hz, 2H), 7.50 (d, J=8.8 Hz, 2H), 6.95 (d, J=9.2 Hz, 2H), 4.91 (m, 1H), 3.69 (s, 1H), 3.45 (s, 1H), 3.17 (s, 1H), 3.00 (s, 1H), 2.82 (s, 3H), 1.66 (d, J=6.8 Hz, 6H) ppm.

Example 77

The Preparation of 8-(3-trifluoromethylphenylamino)-9-isopropyl-2-(4-(4-methylpiperazin-1-yl)phenylamino)-9H-purine

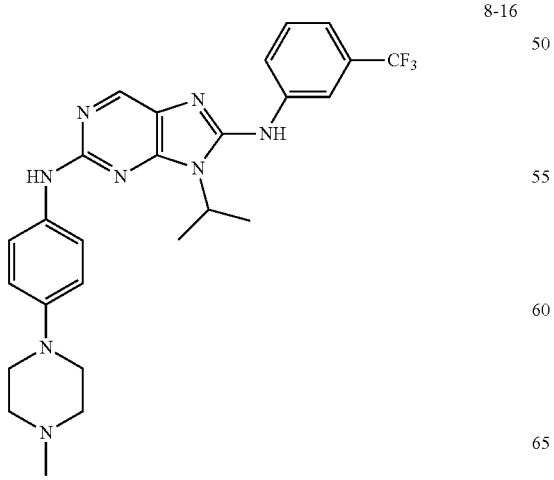

8-16

Compound 5-7 (2.05 g) was dissolved into dichloromethane (90 ml). To the mixture were successively added EDCI (2.3 g), N,N-diisopropylethylamine (4.9 ml), and meta-trifluoromethylphenyl isothiocyanate (1.4 g). The mixture was stirred at room temperature for half an hour, and refluxed for 10 hours. TLC detection indicated the completion of the reaction of the starting material 5-7. After cooling the mixture, purification was conducted by a column chromatography to obtain a pale red solid in a yield of 55.8%. ESI-MS (m/z, %) 509.24 (M−H)⁻. ¹H NMR (400 MHz, DMSO-d$_6$): δ 10.80 (s, 1H), 10.03 (s, 1H), 8.50 (s, 1H), 8.32 (s, 1H), 8.19 (d, J=8.0, 1H), 7.62 (t, J=7.8, 1H), 7.55 (d, J=8.8, 2H), 7.40 (d, J=7.6, 1H), 7.04 (d, J=9.2, 2H), 5.05 (m, 1H), 3.78 (d, J=12.4, 4H), 3.04-3.20 (m, 4H), 2.82 (d, J=4.0, 3H), 1.64 (d, J=6.4, 6H) ppm.

Example 78

The Preparation of 8-(3-methoxyphenylamino)-9-isopropyl-2-(4-(4-methylpiperazin-1-yl)phenylamino)-9H-purine

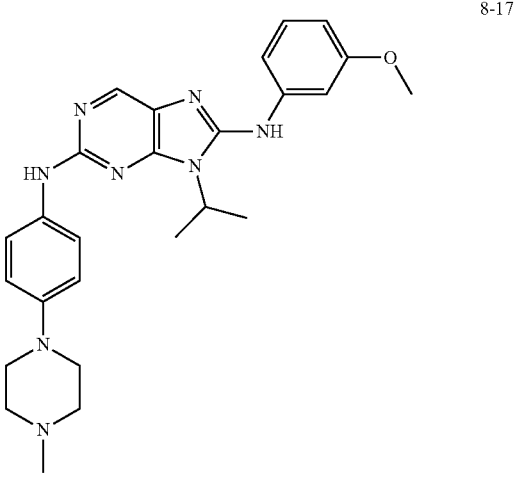 [SMILES: COc1cccc(Nc2nc3cnc(Nc4ccc(N5CCN(C)CC5)cc4)nc3n2C(C)C)c1]

8-17

Compound 5-7 (2.05 g) was dissolved into dichloromethane (90 ml). To the mixture were successively added EDCI (2.3 g), N,N-diisopropylethylamine (4.9 ml), and meta-methoxyphenyl isothiocyanate (1.2 g). The mixture was stirred at room temperature for half an hour, and refluxed for 10 hours. TLC detection indicated the completion of the reaction of the starting material 5-7. After cooling the mixture, purification was conducted by a column chromatography to obtain a pale red solid in a yield of 58.8%. ESI-MS (m/z, %) 471.28 (M−H)⁻. ¹H NMR (400 MHz, DMSO-d$_6$): δ 9.06 (d, J=16.8, 2H), 8.37 (s, 1H), 7.69 (d, J=8.8, 2H), 7.52 (s, 1H), 7.42 (d, J=4.0, 1H), 7.22 (t, J=8.2, 1H), 6.95 (d, J=9.2, 2H), 6.56 (m, 1H), 4.91 (m, 1H), 3.76 (s, 1H), 2.81 (s, 1H), 1.66 (d, J=6.8, 6H) ppm.

Example 79

The Preparation of 8-(4-methoxyphenylamino)-9-isopropyl-2-(4-(4-methylpiperazin-1-yl)phenylamino)-9H-purine

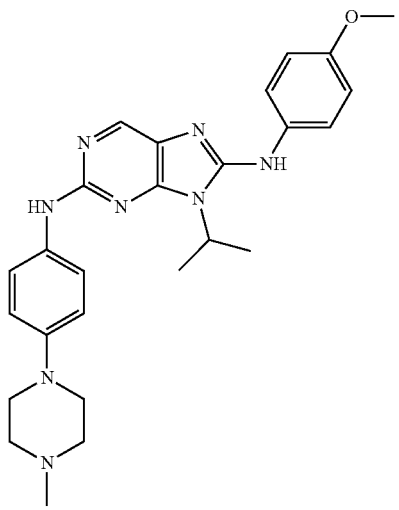

8-18

Compound 5-7 (2.05 g) was dissolved into dichloromethane (90 ml). To the mixture were successively added EDCI (2.3 g), N,N-diisopropylethylamine (4.9 ml), and para-methoxyphenyl isothiocyanate (1.2 g). The mixture was stirred at room temperature for half an hour, and refluxed for 10 hours. TLC detection indicated the completion of the reaction of the starting material 5-7. After cooling the mixture, purification was conducted by a column chromatography to obtain a pale red solid in a yield of 59.8%. ESI-MS (m/z, %) 471.28 (M−H)⁻. ¹H NMR (400 MHz, DMSO-d$_6$): δ 9.04 (s, 1H), 8.93 (s, 1H), 8.30 (s, 1H), 7.71 (m, J=8.9, 4H), 6.94 (t, J=9.4, 4H), 4.90 (m, 1H), 3.75 (s, 3H), 3.46-3.43 (m, 4H), 3.17-3.06 (m, 4H), 2.81 (s, 3H), 1.67 (d, J=6.8, 6H) ppm.

Example 80

The Preparation of 8-(3-chloro-4-(3-fluorobenzyloxy)phenylamino)-9-isopropyl-2-(4-(4-methylpiperazin-1-yl)phenylamino)-9H-purine

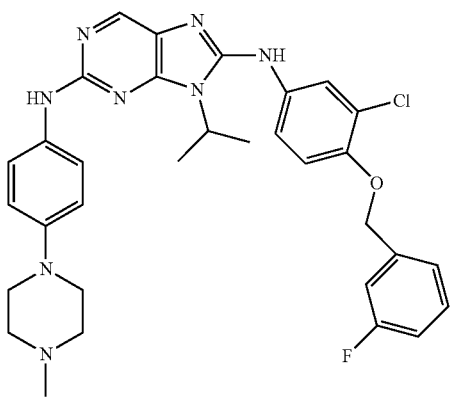

8-19

Compound 5-7 (2.05 g) was dissolved into dichloromethane (90 ml). To the mixture were successively added EDCI (2.3 g), N,N-diisopropylethylamine (4.9 ml), and 3-chloro-4-(3-fluorobenzyloxy)phenyl isothiocyanate (2.1 g). The mixture was stirred at room temperature for half an hour, and refluxed for 10 hours. TLC detection indicated the completion of the reaction of the starting material 5-7. After cooling the mixture, purification was conducted by a column chromatography to obtain a pale red solid in a yield of 65.7%. ESI-MS (m/z, %) 599.22 (M−H)⁻. ¹H NMR (400 MHz, DMSO-d$_6$): δ 9.02 (d, J=4.8 Hz, 2H), 8.36 (s, 1H), 8.08 (d, J=2.4 Hz, 1H), 7.67 (m, 3H), 7.46 (m, 1H), 7.31 (t, J=7.6 Hz, 2H), 7.20 (m, 2H), 6.91 (d, J=8.8 Hz, 2H), 5.21 (s, 2H), 4.83 (m, 1H), 3.15 (s, 4H), 2.81 (s, 3H), 2.48 (s, 2H), 2.30 (s, 2H), 1.66 (d, J=6.8 Hz, 6H) ppm.

Example 81

The Preparation of 8-(3-chloro-4-((pyridin-2-yl)methoxy)phenylamino)-9-isopropyl-2-(4-(4-methylpiperazin-1-yl)phenylamino)-9H-purine

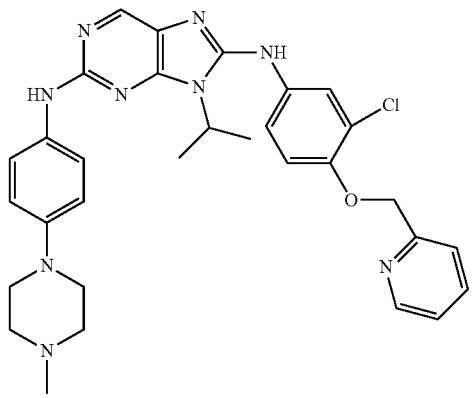

8-20

Compound 5-7 (2.05 g) was dissolved into dichloromethane (90 ml). To the mixture were successively added EDCI (2.3 g), N,N-diisopropylethylamine (4.9 ml), and (3-chloro-4-(pyridin-2-yl)methoxy)phenyl isothiocyanate (2.0 g). The mixture was stirred at room temperature for half an hour, and refluxed for 10 hours. TLC detection indicated the completion of the reaction of the starting material 5-7. After cooling the mixture, purification was conducted by a column chromatography to obtain a pale red solid in a yield of 65.9%. ESI-MS (m/z, %) 582.31 (M−H)⁻. ¹H NMR (400 MHz, DMSO-d6): δ 9.13 (s, 1H), 8.60 (d, 1H), 8.30 (s, 1H), 7.85 (m, 3H), 7.69 (m, 1H), 7.60 (d, 2H), 7.30-7.15 (m, 4H), 7.05 (d, 1H), 4.88 (m, 1H), 3.48 (br, 4H), 2.97 (br, 4H), 2.78 (s, 3H), 1.59 (d, J=6.8 Hz, 6H) ppm.

Example 82

The Preparation of 8-(3-(3-(3-chloro-4-fluorophenyl)ureido)phenylamino)-9-isopropyl-2-(4-(4-methylpiperazin-1-yl)phenylamino)-9H-purine

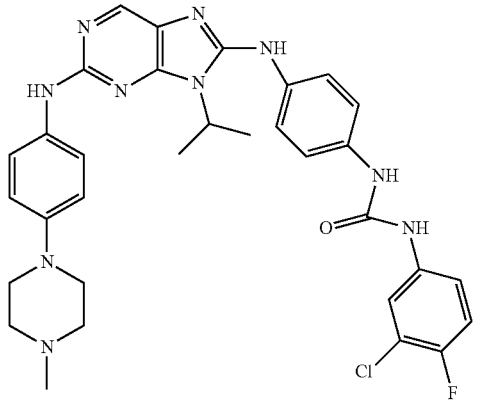

8-21

Compound 5-7 (2.05 g) was dissolved into dichloromethane (90 ml). To the mixture were successively added EDCI (2.3 g), N,N-diisopropylethylamine (4.9 ml), and 3-(3-(3-chloro-4-fluorophenyl)ureido)phenyl isothiocyanate (2.3 g). The mixture was stirred at room temperature for half an hour, and refluxed for 10 hours. TLC detection indicated the completion of the reaction of the starting material 5-7. After cooling the mixture, purification was conducted by a column chromatography to obtain a pale red solid in a yield of 62.5%. ESI-MS (m/z, %) 627.21 (M−H)⁻. ¹H NMR (400 MHz, DMSO-d₆): δ 8.99 (d, J=9.6 Hz, 2H), 8.88 (s, 1H), 8.80 (s, 1H), 8.34 (s, 1H), 7.94 (s, 1H), 7.84 (m, 1H), 7.63 (d, J=9.2 Hz, 2H), 7.47 (d, J=8 Hz, 1H), 7.37-7.28 (m, 2H), 7.22 (t, J=8 Hz, 1H), 7.11 (d, J=8 Hz, 1H), 6.88 (d, J=9.2 Hz, 2H), 4.90 (m, 1H), 3.06 (t, J=4.8 Hz, 3H), 2.51 (m, 4H), 2.48 (d, J=4.4 Hz, 2H), 2.26 (d, J=19.6 Hz, 2H), 1.67 (d, J=6.8 Hz, 6H) ppm.

Example 83

The Preparation of 8-(4-(3-fluorophenylcarbamoyl)phenylamino)-9-isopropyl-2-(4-(4-methylpiperazin-1-yl)phenylamino)-9H-purine

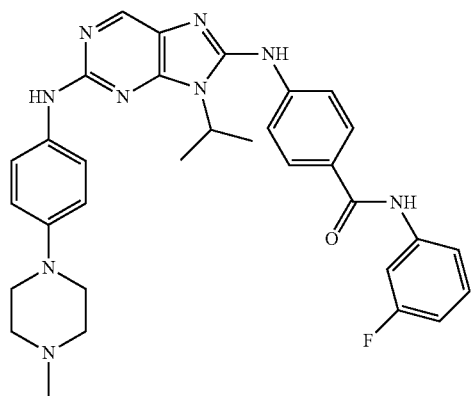

8-22

Compound 5-7 (2.05 g) was dissolved into dichloromethane (90 ml). To the mixture were successively added EDCI (2.3 g), N,N-diisopropylethylamine (4.9 ml), and 4-(3-fluorophenylcarbamoyl)phenyl isothiocyanate (2.0 g). The mixture was stirred at room temperature for half an hour, and refluxed for 10 hours. TLC detection indicated the completion of the reaction of the starting material 5-7. After cooling the mixture, purification was conducted by a column chromatography to obtain a pale red solid in a yield of 54.6%. ESI-MS (m/z, %) 578.22 (M−H)⁻. ¹H NMR (400 MHz, DMSO-d₆): δ 10.30 (s, 1H), 9.44 (s, 1H), 9.12 (s, 1H), 8.44 (s, 1H), 7.98 (s, 3H), 7.78 (d, J=11.6 Hz, 1H), 7.68 (d, J=8.8 Hz, 2H), 7.59 (d, J=7.2 Hz, 2H), 7.38 (m, 1H), 6.91 (m, 3H), 4.94 (m, 1H), 3.27 (s, 4H), 2.96 (d, J=8 Hz, 2H), 2.73 (s, 3H), 2.55 (s, 2H), 1.69 (d, J=6.4 Hz, 6H) ppm;

Example 84

The Preparation of 8-phenylamino-9-cyclopropyl-2-(4-(4-methylpiperazin-1-yl)phenylamino)-9H-purine

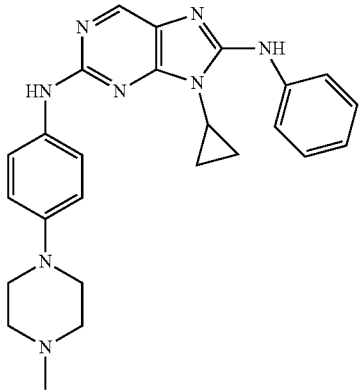

8-23

Compound 5-8 (2.0 g) was dissolved into dichloromethane (90 ml). To the mixture were successively added EDCI (2.3 g), N,N-diisopropylethylamine (4.9 ml), and phenyl isothiocyanate (0.86 ml). The mixture was stirred at room temperature for half an hour, and refluxed for 10 hours. TLC detection indicated the completion of the reaction of the starting material 5-8. After cooling the mixture, purification was conducted by a column chromatography to obtain a pale red solid in a yield of 58.3%. ESI-MS (m/z, %) 439.23 (M−H)⁻. ¹H NMR (400 MHz, DMSO-d₆): δ 10.14 (s, 1H), 9.64 (s, 1H), 8.39 (s, 1H), 7.851 (d, J=8 Hz, 2H), 7.60 (d, J=8.8 Hz, 2H), 7.41 (t, J=8 Hz, 2H), 7.13 (t, J=7.2 Hz, 1H), 7.05 (d, J=9.2 Hz, 2H), 3.43-3.50 (m, 4H), 3.20-3.24 (m, 4H), 2.82 (d, J=3.2 Hz, 3H), 1.19-1.30 (m, 4H) ppm.

Example 85

The Preparation of 8-phenylamino-9-methyl-2-(4-(4-methylpiperazin-1-yl)phenylamino)-9H-purine

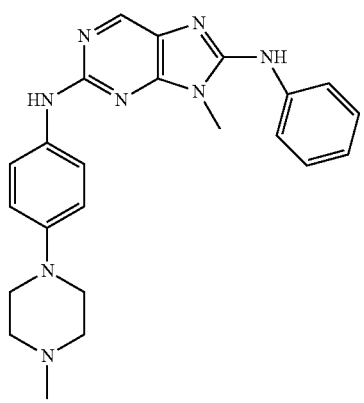

8-24

Compound 5-6 (1.9 g) was dissolved into dichloromethane (90 ml). To the mixture were successively added EDCI (2.3 g), N,N-diisopropylethylamine (4.9 ml), and phenyl isothiocyanate (0.86 ml). The mixture was stirred at room temperature for half an hour, and refluxed for 10 hours. TLC detection indicated the completion of the reaction of the starting material 5-6. After cooling the mixture, purification was conducted by a column chromatography to obtain a pale red solid in a yield of 51.1%. ESI-MS (m/z, %) 413.24 (M−H)⁻. $^1$H NMR (400 MHz, DMSO-$d_6$): δ 9.57 (s, 1H), 9.52 (s, 1H), 8.37 (s, 1H), 7.88 (d, J=7.6 Hz, 2H), 7.656 (d, J=8.4 Hz, 2H), 7.37 (t, J=8 Hz, 2H), 7.05 (t, J=7.2 Hz, 1H), 6.99 (d, J=8.8 Hz, 2H), 3.69 (s, 3H), 3.381 (s, 4H), 3.16 (d, J=8.8 Hz, 2H), 3.03 (d, J=12 Hz, 2H), 2.82 (s, 3H) ppm.

Example 86

The Preparation of 8-phenylamino-2-(4-(4-methylpiperazin-1-yl)phenylamino)-9H-purine

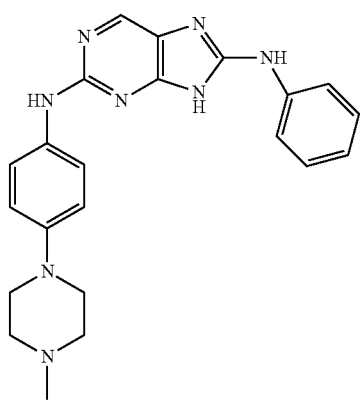

8-25

Compound 5-5 (2.4 g) was dissolved into dichloromethane (120 ml). To the mixture were successively added EDCI (3.1 g), N,N-diisopropylethylamine (6.6 ml), and para-trifluoromethylphenyl isothiocyanate (1.1 ml). The mixture was stirred at room temperature for half an hour, and refluxed for 10 hours. TLC detection indicated the completion of the reaction of the starting material 5-5. After cooling the mixture, purification was conducted by a column chromatography to obtain a pale red solid in a yield of 57.3%. ESI-MS (m/z, %) 399.27 (M−H)⁻. $^1$H NMR (400 MHz, DMSO-$d_6$): δ 10.89 (s, 1H), 9.93 (s, 1H), 8.77 (s, 1H), 8.20 (s, 1H), 7.30 (d, J=7.2 Hz, 2H), 7.63 (d, J=8.4 Hz, 2H), 7.34 (t, J=6.8 Hz, 2H), 7.00 (s, 1H), 6.87 (d, J=8.8 Hz, 2H), 3.04 (t, J=4.4 Hz, 4H), 2.46 (t, J=4.4 Hz, 4H), 2.23 (s, 3H) ppm.

Example 87

The Preparation of 8-phenylamino-9-cyclopentyl-2-(4-(4-methylpiperazin-1-yl)phenylamino)-9H-purine

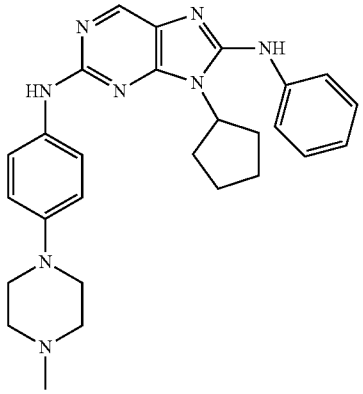

8-26

Compound 5-9 (1.6 g) was dissolved into dichloromethane (65 ml). To the mixture were successively added EDCI (1.7 g), N,N-diisopropylethylamine (3.7 ml), and phenyl isothiocyanate (0.6 ml). The mixture was stirred at room temperature for half an hour, and refluxed for 10 hours. TLC detection indicated the completion of the reaction of the starting material 5-9. After cooling the mixture, purification was conducted by a column chromatography to obtain a pale red solid in a yield of 52.1%. ESI-MS (m/z, %) 467.26 (M−H)⁻. $^1$H NMR (400 MHz, DMSO-$d_6$): δ 9.18 (s, 1H), 9.08 (s, 1H), 8.36 (s, 1H), 7.85 (d, J=7.6 Hz, 2H), 7.67 (d, J=8.4 Hz, 2H), 7.32 (t, J=3.6 Hz, 2H), 6.93-7.00 (m, 3H), 5.04 (t, J=8 Hz, 1H), 3.36 (s, 8H), 2.79 (s, 3H), 2.46 (s, 2H), 2.05 (s, 4H), 1.70 (s, 2H) ppm.

Example 88

The Preparation of 8-(4-trifluoromethylphenylamino)-9-isopropyl-2-(4-(4-methylpiperazin-1-yl)phenylamino)-9H-purine

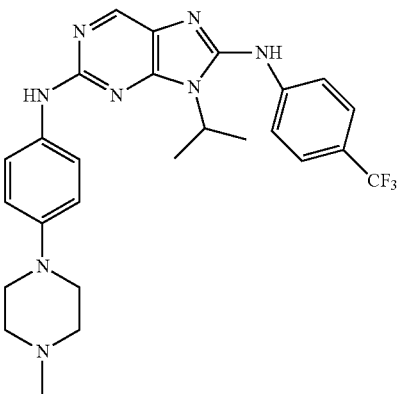

8-27

Compound 5-7 (2.05 g) was dissolved into dichloromethane (90 ml). To the mixture were successively added EDCI (2.3 g), N,N-diisopropylethylamine (4.9 ml), and para-trifluoromethylphenyl isothiocyanate (1.4 g). The mixture was stirred at room temperature for half an hour, and refluxed for 10 hours. TLC detection indicated the completion of the reaction of the starting material 5-7. After cooling the mixture, purification was conducted by a column chromatography to obtain a pale red solid in a yield of 55.4%. ESI-MS (m/z, %) 509.25 (M−H)$^-$. $^1$H NMR (400 MHz, DMSO-d$_6$): δ 9.46 (s, 1H), 9.09 (s, 1H), 8.44 (s, 1H), 8.03 (d, J=8.4 Hz, 2H), 7.67 (m, J=8.8 Hz, 4H), 6.90 (d, J=8.8 Hz, 2H), 4.90 (m, 1H), 3.10 (s, 4H), 2.59 (s, 4H), 2.32 (s, 3H), 1.68 (d, J=6.4 Hz, 6H) ppm.

Example 89

The Preparation of 8-(3-acrylylaminophenylamino)-9-isopropyl-2-(4-(4-methylpiperazin-1-yl)phenylamino)-9H-purine

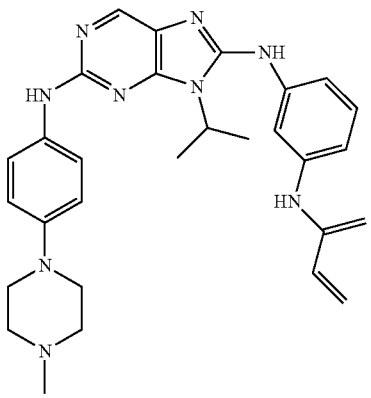

8-28

Compound 5-7 (2.05 g) was dissolved into dichloromethane (90 ml). To the mixture were successively added EDCI (2.3 g), N,N-diisopropylethylamine (4.9 ml), and 3-acrylylaminophenyl isothiocyanate (1.5 g). The mixture was stirred at room temperature for half an hour, and refluxed for 10 hours. TLC detection indicated the completion of the reaction of the starting material 5-7. After cooling the mixture, purification was conducted by a column chromatography to obtain a pale red solid in a yield of 58.9%. ESI-MS (m/z, %) 510.25 (M−H)$^-$. $^1$H NMR (400 MHz, DMSO-d$_6$): δ 9.51 (s, 1H), 9.07 (s, 1H), 8.52 (s, 1H), 8.09 (d, J=8.4 Hz, 2H), 7.61 (m, 4H), 6.92 (d, J=8.8 Hz, 2H), 6.54 (s, 1H), 6.05 (s, 1H), 5.59 (s, 1H), 4.79 (m, 1H), 2.93 (s, 4H), 2.62 (br, 4H), 2.38 (s, 3H), 1.61 (d, J=6.4 Hz, 6H) ppm.

Example 90

The Preparation of 9-isopropyl-2-(4-(4-methylpiperazin-1-yl)phenylamino)-8-(pyridin-3-yl)-9H-purine

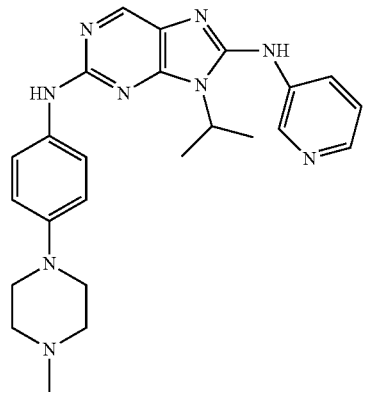

8-29

Compound 5-7 (2.05 g) was dissolved into dichloromethane (90 ml). To the mixture were successively added EDCI (2.3 g), N,N-diisopropylethylamine (4.9 ml), and 3-pyridinyl isothiocyanate (1.0 g). The mixture was stirred at room temperature for half an hour, and refluxed for 10 hours. TLC detection indicated the completion of the reaction of the starting material 5-7. After cooling the mixture, purification was conducted by a column chromatography to obtain a pale red solid in a yield of 65.7%. ESI-MS (m/z, %) 442.26 (M−H)$^-$. $^1$H NMR (400 MHz, DMSO-d$_6$): δ 9.38 (s, 1H), 9.13 (s, 1H), 8.99 (s, 1H), 8.40 (s, 1H), 8.36 (d, J=8.4 Hz, 1H), 8.20 (d, J=4.4 Hz, 1H), 7.70 (d, J=8.8 Hz, 2H), 7.37 (m, 1H), 6.96 (d, J=8.8 Hz, 2H), 4.97-4.92 (m, 1H), 3.35 (s, 6H), 2.80 (s, 3H), 2.53 (s, 2H), 1.69 (s, 6H) ppm.

Example 91

The Preparation of 9-isopropyl-2-(4-(4-methylpiperazin-1-yl)phenylamino)-8-cyclohexyl-9H-purine

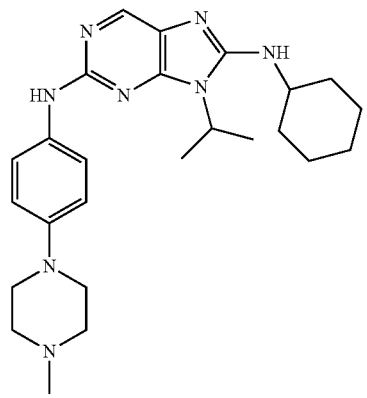

8-30

Compound 5-7 (2.05 g) was dissolved into dichloromethane (90 ml). To the mixture were successively added EDCI (2.3 g), N,N-diisopropylethylamine (4.9 ml), and cyclohexyl isothiocyanate (1.0 g). The mixture was stirred at room temperature for half an hour, and refluxed for 10 hours. TLC detection indicated the completion of the reaction of the starting material 5-7. After cooling the mixture, purification was conducted by a column chromatography to obtain a pale red solid in a yield of 67.8%. ESI-MS (m/z, %) 447.28 (M−H)⁻. ¹H NMR (400 MHz, DMSO-d₆): δ 10.89 (s, 1H), 9.26 (s, 1H), 8.23 (s, 1H), 7.62 (d, J=9.2, 2H), 6.95 (d, J=8.8, 2H), 4.72 (m, 1H), 4.03 (m, J=7.1, 1H), 3.69 (s, 4H), 3.13-3.09 (m, 4H), 2.80 (s, 3H), 1.98 (d, J=5.6, 2H), 1.76 (d, J=9.6, 2H), 1.57 (d, J=6.8, 6H), 1.37-1.26 (m, 6H) ppm.

Example 92

The Preparation of 9-cyclopentyl-6-methyl-2-(4-(4-methylpiperazin-1-yl)phenylamino)-8-phenyl-9H-purine

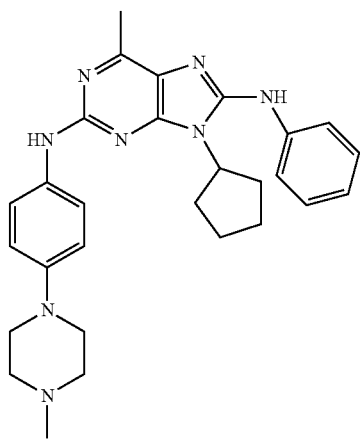

8-31

Compound 5-10 (2.3 g) was dissolved into dichloromethane (90 ml). To the mixture were successively added EDCI (2.3 g), N,N-diisopropylethylamine (4.9 ml), and phenyl isothiocyanate (0.9 mlg). The mixture was stirred at room temperature for half an hour, and refluxed for 10 hours. TLC detection indicated the completion of the reaction of the starting material 5-10. After cooling the mixture, purification was conducted by a column chromatography to obtain a pale red solid in a yield of 61.1%. ESI-MS (m/z, %) 481.27 (M−H)⁻. ¹H NMR (400 MHz, DMSO-d₆): δ 9.12 (s, 1H), 8.39 (s, 1H), 7.75 (m, 2H), 7.59 (m, 2H), 7.46 (m, 2H), 7.10 m, 3H), 4.62 (m, 1H), 3.38 (s, 6H), 2.75 (s, 3H), 2.68 (s, 3H), 2.42 (br, 2H), 2.15 (s, 4H), 1.76 (m, 4H) ppm.

Example 93

The Preparation of 9-isopropyl-6-methoxy-2-(4-(4-methylpiperazin-1-yl)phenylamino)-8-phenyl-9H-purine

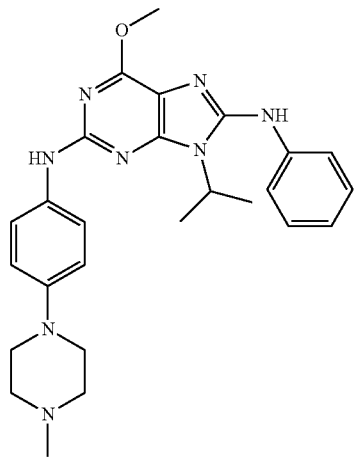

8-32

Compound 5-11 (2.2 g) was dissolved into dichloromethane (90 ml). To the mixture were successively added EDCI (2.3 g), N,N-diisopropylethylamine (4.9 ml), and phenyl isothiocyanate (0.9 mlg). The mixture was stirred at room temperature for half an hour, and refluxed for 10 hours. TLC detection indicated the completion of the reaction of the starting material 5-11. After cooling the mixture, purification was conducted by a column chromatography to obtain a pale red solid in a yield of 63.5%. ESI-MS (m/z, %) 471.28 (M−H)⁻. ¹H NMR (400 MHz, DMSO-d6): δ 8.56 (s, 1H), 7.82 (d, J=8.0 Hz, 2H), 7.61 (d, J=8.4 Hz, 2H), 7.39 (m, 2H), 7.26 (m, 2H), 7.02 (m, 2H), 4.92 (m, 1H), 4.06 (s, 3H), 3.49 (br, 4H), 3.27 (br, 4H), 2.83 (s, 3H), 1.61 (d, J=6.8 Hz, 6H) ppm.

Example 94

The Preparation of 9-isopropyl-6-methylamino-2-(4-(4-methylpiperazin-1-yl)phenylamino)-8-phenyl-9H-purine

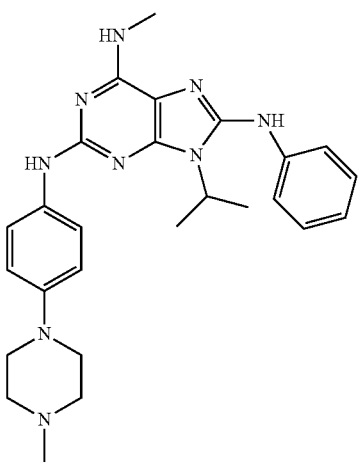

8-33

Compound 5-12 (2.2 g) was dissolved into dichloromethane (90 ml). To the mixture were successively added EDCI (2.3 g), N,N-diisopropylethylamine (4.9 ml), and phenyl isothiocyanate (0.9 mlg). The mixture was stirred at room temperature for half an hour, and refluxed for 10 hours. TLC detection indicated the completion of the reaction of the starting material 5-12. After cooling the mixture, purification was conducted by a column chromatography to obtain a pale red solid in a yield of 65.4%. ESI-MS (m/z, %) 470.25 (M−H)⁻. ¹H NMR (400 MHz, DMSO-d6): δ 8.61 (s, 1H), 7.83 (d, J=8.0 Hz, 2H), 7.69 (m, 2H), 7.37 (m, 2H), 7.25 (m, 1H), 7.04 (m, 3H), 4.71 (m, 1H), 3.49 (br, 4H), 3.27 (br, 4H), 2.86 (s, 3H), 1.65 (d, J=6.8 Hz, 6H) ppm.

Example 95

The Preparation of 9-isopropyl-6-methyl-2-(4-(4-methylpiperazin-1-yl)phenylamino)-8-phenyl-9H-purine

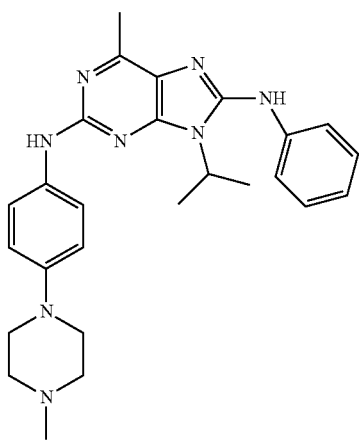

8-34

Compound 5-13 (2.2 g) was dissolved into dichloromethane (90 ml). To the mixture were successively added EDCI (2.3 g), N,N-diisopropylethylamine (4.9 ml), and phenyl isothiocyanate (0.9 ml). The mixture was stirred at room temperature for half an hour, and refluxed for 10 hours. TLC detection indicated the completion of the reaction of the starting material 5-13. After cooling the mixture, purification was conducted by a column chromatography to obtain a pale red solid in a yield of 66.7%. ESI-MS (m/z, %) 455.28 (M−H)⁻; ¹H NMR (400 MHz, DMSO-d₆): δ 9.08 (s, 1H), 9.01 (s, 1H), 7.84 (d, J=8.0, 2H), 7.71 (d, J=8.8, 2H), 7.32 (t, J=7.8, 2H), 6.96 (t, J=8.4, 3H), 4.91 (m, J=6.6, 1H), 3.67 (s, 4H), 3.27 (s, 4H), 2.80 (s, 3H), 2.49 (s, 3H), 1.66 (d, J=6.8 Hz, 6H) ppm.

Example 96

The Preparation of 8-(3-chloro-4-fluorophenylamino)-9-cyclopentyl-2-(4-(4-methylpiperazin-1-yl)phenylamino)-9H-purine

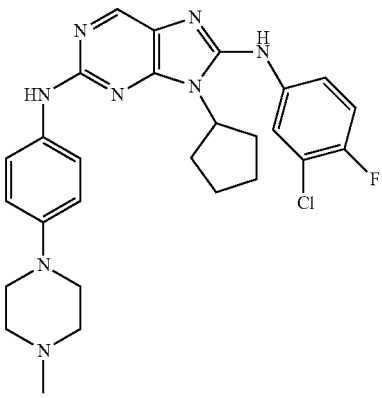

8-35

Compound 5-9 (2.2 g) was dissolved into dichloromethane (90 ml). To the mixture were successively added EDCI (2.3 g), N,N-diisopropylethylamine (4.9 ml), and 3-chloro-4-fluorophenyl isothiocyanate (1.35 g). The mixture was stirred at room temperature for half an hour, and refluxed for 10 hours. TLC detection indicated the completion of the reaction of the starting material 5-9. After cooling the mixture, purification was conducted by a column chromatography to obtain a pale red solid in a yield of 67.6%. ESI-MS (m/z, %) 519.20 (M−H)⁻; ¹H NMR (400 MHz, DMSO-d₆): δ9.41 (s, 1H), 9.10 (s, 1H), 8.42 (s, 1H), 8.23 (m, J=3.07, 1H), 7.80 (m, 1H), 7.66 (d, J=8.8, 2H), 7.39 (t, J=9.2, 1H), 6.94 (d, J=9.2, 2H), 5.01 (m, 1H), 3.41 (s, 4H), 2.81 (s, 3H), 2.54 (s, 4H), 2.46 (s, 2H), 2.05 (s, 4H), 1.70 (d, J=4.4, 2H) ppm.

Example 97

The Preparation of 9-cyclopentyl-2-(4-(4-methylpiperazin-1-yl)phenylamino)-8-(pyridin-3-yl)-9H-purine 8-36

Compound 5-9 (2.2 g) was dissolved into dichloromethane (90 ml). To the mixture were successively added EDCI (2.3 g), N,N-diisopropylethylamine (4.9 ml), and 3-pyridinyl isothiocyanate (1.0 g). The mixture was stirred at room temperature for half an hour, and refluxed for 10 hours. TLC detection indicated the completion of the reaction of the starting material 5-9. After cooling the mixture, purification was conducted by a column chromatography to obtain a pale red solid in a yield of 64.3%. ESI-MS (m/z,%) 468.23 (M−H)$^−$; $^1$H NMR (400 MHz, DMSO-d$_6$): δ 9.40 (s, 1H), 9.11 (s, 1H), 8.97 (d, J=2.0, 1H), 8.40 (s, 1H), 8.35 (d, J=8.4, 1H), 8.20 (d, J=4.4, 1H), 7.66 (d, J=8.8, 2H), 7.36 (m, J=6.6, 1H), 6.93 (d, J=8.8, 2H), 5.02 (m, 1H), 3.20 (s, 4H), 2.73 (s, 3H), 2.47 (s, 4H), 2.06 (s, 4H), 1.71 (s, 2H), 1.23 (s, 2H) ppm.

Example 98

The Preparation of 4-(9-cyclopentylamino-8-(pyridin-3-ylamino)-9H-purin-2-ylamino)-N-(4-methylpiperidin-1-yl)benzamide

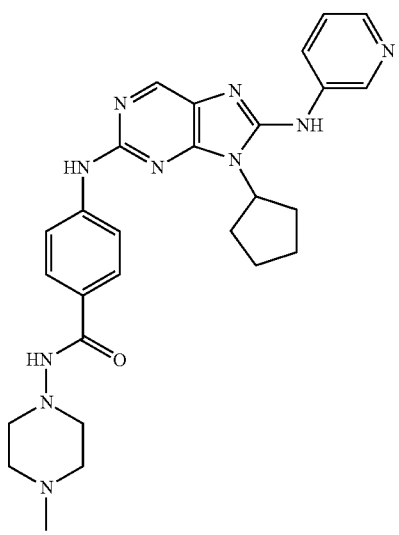

8-37

Compound 5-14 (2.46 g) was dissolved into dichloromethane (90 ml). To the mixture were successively added EDCI (2.3 g), N,N-diisopropylethylamine (4.9 ml), and 3-pyridinyl isothiocyanate (1.0 g). The mixture was stirred at room temperature for half an hour, and refluxed for 10 hours. TLC detection indicated the completion of the reaction of the starting material 5-14. After cooling the mixture, purification was conducted by a column chromatography to obtain a pale red solid in a yield of 70.3%. ESI-MS (m/z, %) 511.23 (M−H)$^−$; $^1$H NMR (400 MHz, DMSO-d$_6$): δ 9.66 (d, J=11.2, 2H), 9.48 (s, 1H), 8.99 (d, J=2.0, 1H), 8.49 (s, 1H), 8.36 (d, J=7.6, 1H), 8.22 (d, J=4.0, 1H), 7.86 (d, J=8.8, 2H), 7.75 (d, J=8.4, 2H), 7.39 (m, J=4.3, 1H), 5.06 (m, 1H), 3.21 (s, 4H), 2.78 (s, 3H), 2.51 (s, 4H), 2.10 (s, 4H), 1.76 (s, 2H), 1.24 (s, 2H) ppm.

Example 99

The Preparation of N-(3-(9-isopropyl-8-phenylamino-9H-purin-2-ylamino)phenyl)acrylamide

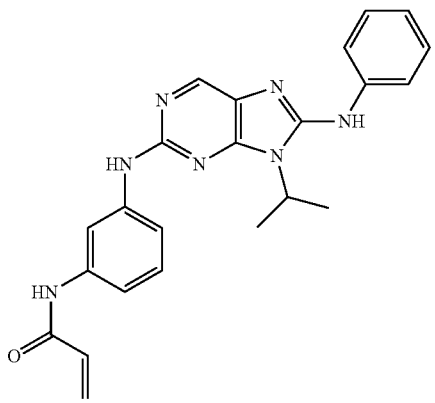

8-38

Compound 5-16 (1.87 g) was dissolved into dichloromethane (90 ml). To the mixture were successively added EDCI (2.3 g), N,N-diisopropylethylamine (4.9 ml), and phenyl isothiocyanate (0.9 ml). The mixture was stirred at room temperature for half an hour, and refluxed for 10 hours. TLC detection indicated the completion of the reaction of the starting material 5-16. After cooling the mixture, purification was conducted by a column chromatography to obtain a pale red solid in a yield of 65.5%. ESI-MS (m/z, %) 414.23 (M−H)$^+$; $^1$H NMR (400 MHz, DMSO-d$_6$): δ 10.05 (s, 1H), 9.29 (s, 1H), 9.02 (s, 1H), 8.40 (s, 1H), 8.02 (s, 1H), 7.84 (d, J=8.0, 2H), 7.57 (d, J=6.8, 1H), 7.34 (t, J=7.2, 2H), 7.20 (t, J=7.4, 2H), 7.00 (t, J=7.2, 1H), 6.49 (m, J=9.1, 1H), 6.26 (d, J=16.8, 1H), 5.74 (d, J=10.0, 1H), 4.90 (m, 1H), 1.68 (d, J=6.8, 6H) ppm.

Example 100

The Preparation of 9-isopropylamino-2-(4-(2-morpholinoethoxy)phenylamino))-8-phenylamino-9H-purine

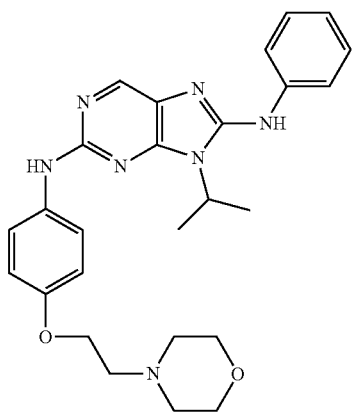

8-39

Compound 5-17 (2.23 g) was dissolved into dichloromethane (90 ml). To the mixture were successively added EDCI (2.3 g), N,N-diisopropylethylamine (4.9 ml), and phenyl isothiocyanate (0.9 ml). The mixture was stirred at room temperature for half an hour, and refluxed for 10 hours. TLC detection indicated the completion of the reaction of the starting material 5-17. After cooling the mixture, purification was conducted by a column chromatography to obtain a pale red solid in a yield of 70.5%. ESI-MS (m/z, %) 474.26 (M−H)⁻. ¹H NMR (400 MHz, DMSO-d₆): δ 9.08 (s, 1H), 8.30 (s, 1H), 8.01 (s, 1H), 7.88 (d, J=8.0 Hz, 2H), 7.71 (d, J=9.2 Hz, 2H), 7.30 (m, 2H), 7.17 (m, 3H), 4.84 (m, 1H), 4.04 (m, 2H), 3.84 (m, 4H), 3.24 (br, 4H), 2.81 (m, 2H), 1.63 (d, J=6.8 Hz, 6H) ppm.

Example 101

The Preparation of 9-isopropylamino-2-(4-(3-(4-methylpiperazin-1-yl)propylamino)phenylamino)-8-phenylamino-9H-purine

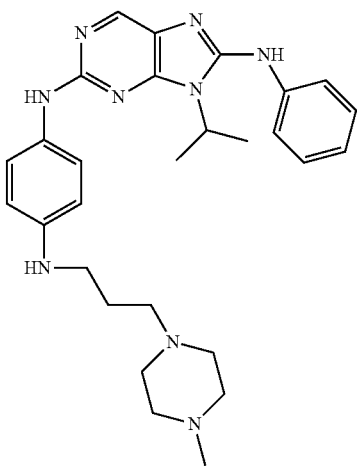

8-40

Compound 5-18 (2.39 g) was dissolved into dichloromethane (90 ml). To the mixture were successively added EDCI (2.3 g), N,N-diisopropylethylamine (4.9 ml), and phenyl isothiocyanate (0.9 ml). The mixture was stirred at room temperature for half an hour, and refluxed for 10 hours. TLC detection indicated the completion of the reaction of the starting material 5-18. After cooling the mixture, purification was conducted by a column chromatography to obtain a pale red solid in a yield of 69.1%. ESI-MS (m/z, %) 500.29 (M−H)⁻. ¹H NMR (400 MHz, DMSO-d₆): δ 9.09 (s, 1H), 8.56 (s, 1H), 7.83 (s, 1H), 7.69 (s, 1H), 7.53 (m, 2H), 7.36 (m, 4H), 6.96 (m, 3H), 4.95 (m, 1H), 3.44 (m, 2H), 3.11 (m, 2H), 2.95 (m, 8H), 2.41 (s, 3H), 1.68 (m, 2H), 1.62 (d, J=6.8 Hz, 6H) ppm.

Example 102

The Preparation of 8-(6-chloropyrimidin-3-yl)-9-isopropylamino-2-(4-(3-(4-methylpiperazin-1-yl)propylamino)phenylamino)-9H-purine

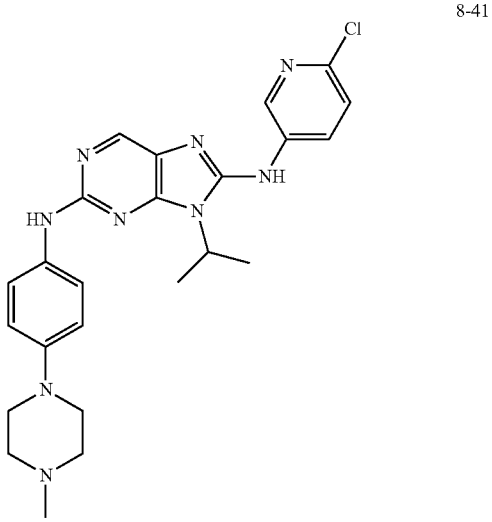

8-41

Compound 5-7 (2.05 g) was dissolved into dichloromethane (90 ml). To the mixture were successively added EDCI (2.3 g), N,N-diisopropylethylamine (4.9 ml), and 2-chloro-5-pyridinyl isothiocyanate (1.3 g). The mixture was stirred at room temperature for half an hour, and refluxed for 10 hours. TLC detection indicated the completion of the reaction of the starting material 5-7. After cooling the mixture, purification was conducted by a column chromatography to obtain a pale red solid in a yield of 69.8%. ESI-MS (m/z, %) 476.29 (M−H)⁻. ¹H NMR (400 MHz, DMSO-d₆): δ 9.65 (s, 1H), 9.21 (s, 1H), 8.85 (s, 1H), 8.44 (d, J=6.8 Hz, 2H), 7.68 (d, J=8.0 Hz, 2H), 7.49 (d, J=8.8 Hz, 1H), 6.96 (d, J=8.0 Hz, 2H), 4.96 (m, 1H), 3.71 (m, 2H), 3.47 (m, 2H), 3.15 (br, 2H), 3.03 (m, 2H), 2.82 (s, 2H), 1.67 (d, J=6.4 Hz, 6H) ppm.

Example 103

The Preparation of 8-(3-chloro-4-(3-fluorobenzyloxy)phenylamino)-9-isopropyl-2-(4-morpholinophenylamino)-9H-purine

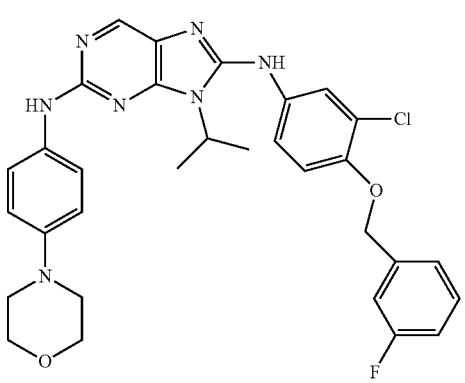

8-42

Compound 5-19 (1.97 g) was dissolved into dichloromethane (90 ml). To the mixture were successively added EDCI (2.3 g), N,N-diisopropylethylamine (4.9 ml), and phenyl isothiocyanate (0.9 ml). The mixture was stirred at room temperature for half an hour, and refluxed for 10 hours. TLC detection indicated the completion of the reaction of the starting material 5-19. After cooling the mixture, purification was conducted by a column chromatography to obtain a pale yellow solid in a yield of 70.6%. ESI-MS (m/z, %) 586.27 (M−H)⁻. ¹H NMR (400 MHz, DMSO-d₆): δ 9.01 (d, J=7.2 Hz, 2H), 8.37 (s, 1H), 8.08 (d, J=2.4 Hz, 1H), 7.67 (m, 3H), 7.46 (m, 1H), 7.31 (m, 2H), 7.20 (m, 2H), 6.91 (d, J=9.2 Hz, 2H), 5.21 (s, 2H), 4.83 (m, 1H), 3.74 (m, 4H), 3.03 (m, 4H), 1.67 (d, J=6.4 Hz, 6H) ppm.

Example 104

The Preparation of 8-(4-bromophenylamino)-9-cyclopentyl-2-(4-(4-methylpiperazin-1-yl)phenylamino)-9H-purine

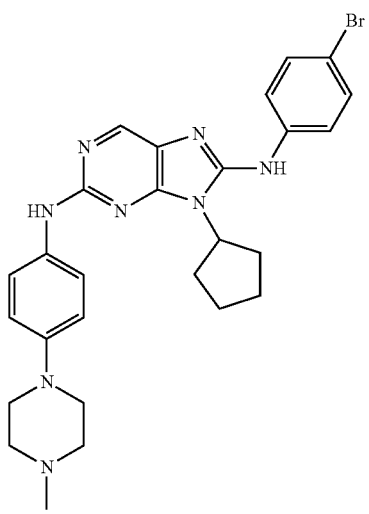

8-43

Compound 5-9 (2.2 g) was dissolved into dichloromethane (90 ml). To the mixture were successively added EDCI (2.3 g), N,N-diisopropylethylamine (4.9 ml), and 4-bromophenyl isothiocyanate (1.65 g). The mixture was stirred at room temperature for half an hour, and refluxed for 10 hours. TLC detection indicated the completion of the reaction of the starting material 5-9. After cooling the mixture, purification was conducted by a column chromatography to obtain a pale red solid in a yield of 66.7%. ESI-MS (m/z, %) 548.18 (M−H)⁺; ¹H NMR (400 MHz, DMSO-d₆): δ9.22 (s, 1H), 9.09 (s, 1H), 8.39 (s, 1H), 7.83 (d, J=9.2 Hz, 2H), 7.65 (d, J=7.0 Hz, 2H), 7.50 (d, J=9.2 Hz, 2H), 6.93 (d, J=8.8 Hz, 2H), 4.95 (m, 1H), 3.27-3.02 (m, 4H), 2.75 (m, 4H), 2.45 (s, 3H), 2.05 (m, 4H), 1.68 (m, 2H), 1.23 (m, 2H).

Example 105

The Preparation of 8-(3-nitrophenylamino)-9-cyclopentyl-2-(4-(4-methylpiperazin-1-yl)phenylamino)-9H-purine

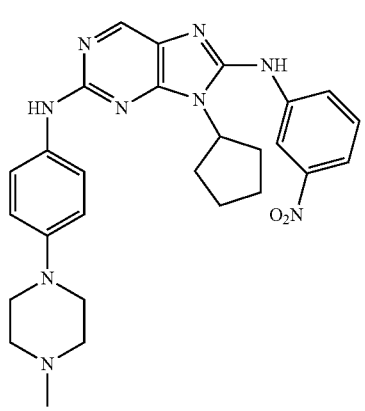

8-44

Compound 5-9 (2.2 g) was dissolved into dichloromethane (90 ml). To the mixture were successively added EDCI (2.3 g), N,N-diisopropylethylamine (4.9 ml), and 3-nitrophenyl isothiocyanate (1.50 g). The mixture was stirred at room temperature for half an hour, and refluxed for 10 hours. TLC detection indicated the completion of the reaction of the starting material 5-9. After cooling the mixture, purification was conducted by a column chromatography to obtain a pale red solid in a yield of 65.4%. ESI-MS (m/z, %) 514.23 (M−H)⁺; ¹H NMR (400 MHz, DMSO-d₆): δ9.75 (s, 1H), 9.23 (s, 1H), 8.87 (s, 1H), 8.45 (s, 1H), 8.32 (d, J=7.6 Hz, 1H), 7.84 (d, J=7.2 Hz, 1H), 7.65 (m, 3H), 6.95 (d, J=8.8 Hz, 2H), 5.04 (m, 1H), 3.72 (m, 2H), 3.49 (m, 2H), 3.16 (m, 2H), 2.99 (m, 2H), 2.83 (s, 3H), 2.45 (m, 2H), 2.06 (m, 4H), 1.71 (m, 2H).

Example 106

The Preparation of 8-benzylamino-9-cyclopentyl-2-(4-(4-methylpiperazin-1-yl)phenylamino)-9H-purine

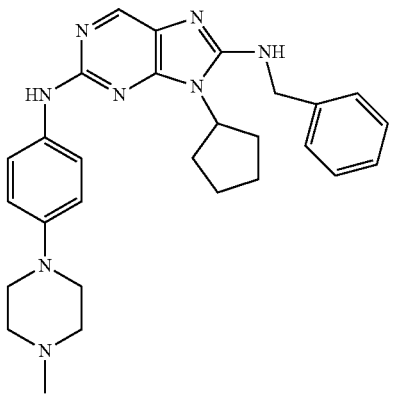

8-45

Compound 5-9 (2.2 g) was dissolved into dichloromethane (90 ml). To the mixture were successively added EDCI (2.3 g), N,N-diisopropylethylamine (4.9 ml), and benzyl isothiocyanate (1.45 g). The mixture was stirred at room temperature for half an hour, and refluxed for 10 hours. TLC detection indicated the completion of the reaction of the starting material 5-9. After cooling the mixture, purification was conducted by a column chromatography to obtain a pale red solid in a yield of 63.9%. ESI-MS (m/z, %) 483.26 (M−H)$^+$; $^1$H NMR (400 MHz, DMSO-d$_6$): δ8.97 (s, 1H), 8.15 (s, 1H), 7.63 (m, 3H), 7.35 (m, 4H), 7.25 (m, 1H), 6.91 (d, J=9.2 Hz, 2H), 4.75 (m, 1H), 4.56 (d, J=8.0 Hz, 2H), 3.67 (m, 2H), 3.44 (m, 2H), 3.16 (m, 2H), 2.97 (m, 2H), 2.82 (s, 3H), 2.38 (m, 2H), 1.99 (m, 4H), 1.65 (m, 2H).

Example 107

The Preparation of 8-(3-ethynylphenylamino)-9-cyclopentyl-2-(4-(4-methylpiperazin-1-yl)phenylamino)-9H-purine

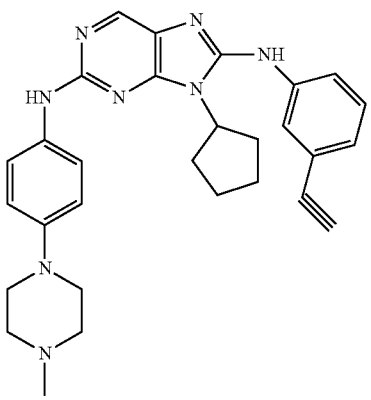

8-46

Compound 5-9 (2.2 g) was dissolved into dichloromethane (90 ml). To the mixture were successively added EDCI (2.3 g), N,N-diisopropylethylamine (4.9 ml), and 3-ethynylphenyl isothiocyanate (1.34 g). The mixture was stirred at room temperature for half an hour, and refluxed for 10 hours. TLC detection indicated the completion of the reaction of the starting material 5-9. After cooling the mixture, purification was conducted by a column chromatography to obtain a pale red solid in a yield of 69.5%. ESI-MS (m/z, %) 493.28 (M−H)$^+$; $^1$H NMR (400 MHz, DMSO-d$_6$): δ9.26 (s, 1H), 9.13 (s, 1H), 8.43 (s, 1H), 8.09 (s, 1H), 7.84 (d, J=8.0 Hz, 1H), 7.67 (d, J=8.4 Hz, 2H), 7.34 (m, 1H), 7.09 (d, J=7.2 Hz, 1H), 6.94 (d, J=10.8 Hz, 2H), 5.00 (m, 1H), 4.20 (s, 1H), 3.67 (m, 2H), 3.47 (m, 2H), 3.17 (m, 2H), 3.00 (m, 2H), 2.78 (s, 3H), 2.46 (m, 2H), 2.05 (m, 4H), 1.71 (m, 2H).

Example 108

The Preparation of 8-(2-fluoro-4-bromophenylamino)-9-cyclopentyl-2-(4-(4-methylpiperazin-1-yl)phenylamino)-9H-purine

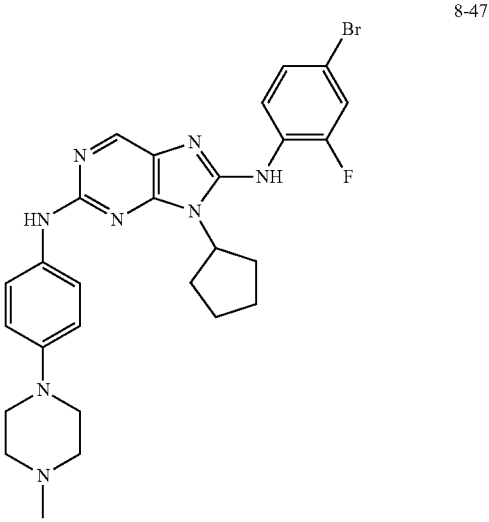 [SMILES: CN1CCN(c2ccc(Nc3ncc4nc(Nc5ccc(Br)cc5F)n(C5CCCC5)c4n3)cc2)CC1]

8-47

Compound 5-9 (2.2 g) was dissolved into dichloromethane (90 ml). To the mixture were successively added EDCI (2.3 g), N,N-diisopropylethylamine (4.9 ml), and 2-fluoro-4-bromophenyl isothiocyanate (1.60 g). The mixture was stirred at room temperature for half an hour, and refluxed for 10 hours. TLC detection indicated the completion of the reaction of the starting material 5-9. After cooling the mixture, purification was conducted by a column chromatography to obtain a pale red solid in a yield of 69.7%. ESI-MS (m/z, %) 565.20 (M−H)$^+$; $^1$H NMR (400 MHz, DMSO-d$_6$): δ9.06 (s, 1H), 8.93 (s, 1H), 8.35 (s, 1H), 7.85 (m, 1H), 7.61 (m, 3H), 7.40 (d, J=8.4 Hz, 1H), 8.67 (d, J=9.2 Hz, 2H), 4.88 (m, 1H), 3.10 (m, 4H), 2.62 (m, 4H), 2.43 (m, 2H), 2.34 (s, 3H), 2.03 (m, 4H), 1.68 (m, 2H).

Example 109

The Preparation of 8-phenylamino-9-cyclopentyl-2-(4-(4-morpholinylmethyl)phenylamino)-9H-purine

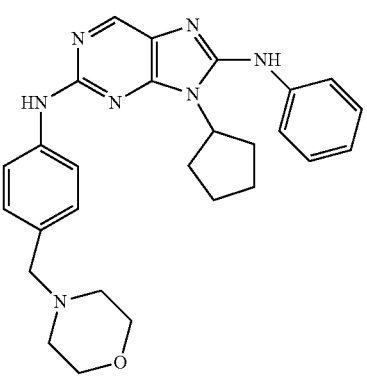

8-48

Compound 5-20 (2.2 g) was dissolved into dichloromethane (90 ml). To the mixture were successively added EDCI (2.3 g), N,N-diisopropylethylamine (4.9 ml), and phenyl isothiocyanate (1.0 g). The mixture was stirred at room temperature for half an hour, and refluxed for 10 hours. TLC detection indicated the completion of the reaction of the starting material 5-9. After cooling the mixture, purification was conducted by a column chromatography to obtain a pale red solid in a yield of 69.9%. ESI-MS (m/z, %) 470.27 (M–H)+. $^1$H NMR (400 MHz, DMSO-d$_6$): δ9.57 (s, 1H), 9.16 (s, 1H), 8.45 (s, 1H), 7.91 (s, 1H), 7.86 (d, J=8.0 Hz, 2H), 7.76 (s, 1H), 7.47 (s, 1H), 7.38 (m, 2H), 7.22 (s, 1H), 7.03 (m, 1H), 5.04 (m, 1H), 4.10 (m, 2H), 3.70 (m, 4H), 3.15 (m, 2H), 2.37 (m, 2H), 2.05 (m, 4H), 1.75 (m, 2H), 1.29 (m, 2H).

Example 110

The Preparation of 8-(3-fluorophenylamino)-9-cyclopentyl-2-(4-(4-methylpiperazin-1-yl)phenylamino)-9H-purine

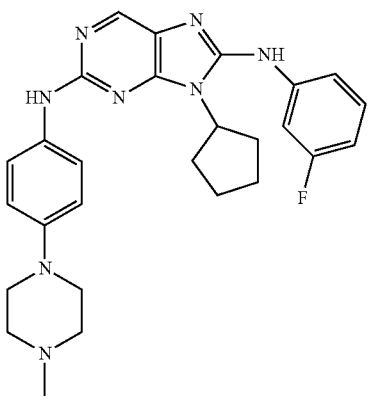

8-49

Compound 5-9 (2.2 g) was dissolved into dichloromethane (90 ml). To the mixture were successively added EDCI (2.3 g), N,N-diisopropylethylamine (4.9 ml), and 3-fluorophenyl isothiocyanate (1.0 g). The mixture was stirred at room temperature for half an hour, and refluxed for 10 hours. TLC detection indicated the completion of the reaction of the starting material 5-9. After cooling the mixture, purification was conducted by a column chromatography to obtain a pale red solid in a yield of 67.4%. ESI-MS (m/z, %) 487.25 (M–H)+; $^1$H NMR (400 MHz, DMSO-d$_6$): δ9.42 (s, 1H), 9.13 (s, 1H), 8.42 (s, 1H), 7.92 (d, J=12.0 Hz, 1H), 7.67 (d, J=9.2 Hz, 2H), 7.59 (d, J=8.0 Hz, 1H), 7.35 (m, 1H), 6.94 (d, J=8.8 Hz, 2H), 6.79 (m, 1H), 5.02 (m, 1H), 3.68 (m, 2H), 3.44 (m, 2H), 3.18 (m, 2H), 3.01 (m, 2H), 2.81 (s, 3H), 2.44 (m, 2H), 2.05 (m, 4H), 1.70 (m, 2H).

Example 111

The Preparation of 8-phenylamino-9-cyclohexyl-2-(4-(4-methylpiperazin-1-yl)phenylamino)-9H-purine

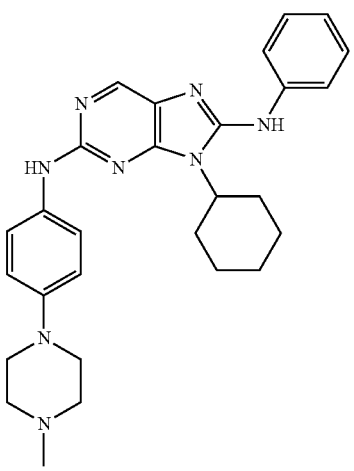

8-50

Compound 5-21 (1.53 g) was dissolved into dichloromethane (35 ml). To the mixture were successively added EDCI (1.54 g), N,N-diisopropylethylamine (3.31 ml), and phenyl isothiocyanate (0.56 g). The mixture was stirred at room temperature for half an hour, and refluxed for 10 hours. TLC detection indicated the completion of the reaction of the starting material 5-21. After cooling the mixture, purification was conducted by a column chromatography to obtain a pale red solid in a yield of 69.4%. ESI-MS (m/z, %) 483.25 (M–H)+. $^1$H NMR (400 MHz, DMSO-d$_6$): δ9.04 (s, 1H), 8.99 (s, 1H), 8.34 (s, 1H), 7.80 (d, J=8.4 Hz, 2H), 7.67 (d, J=8.8 Hz, 2H), 7.33 (m, 2H), 6.98 (m, 1H), 6.87 (d, J=8.4 Hz, 2H), 4.74 (m, 1H), 3.05 (m, 4H), 2.61 (m, 2H), 5.47 (m, 4H), 2.23 (s, 3H), 1.91 (m, 2H), 1.81 (m, 3H), 1.44 (m, 2H), 1.34 (m, 1H).

Example 112

The Preparation of 8-(3-hydroxyphenylamino)-9-cyclopentyl-2-(4-(4-methylpiperazin-1-yl)phenylamino)-9H-purine

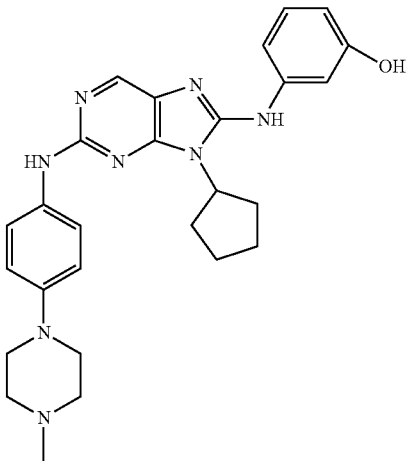

8-51

Compound 5-9 (2.1 g) was dissolved into dichloromethane (90 ml). To the mixture were successively added EDCI (2.3 g), N,N-diisopropylethylamine-2.1 ml), and 3-hydroxyphenyl isothiocyanate (1.05 g). The mixture was stirred at room temperature for half an hour, and refluxed for 10 hours. TLC detection indicated the completion of the reaction of the starting material 5-9. After cooling the mixture, purification was conducted by a column chromatography to obtain a pale red solid in a yield of 70.4%. ESI-MS (m/z, %) 485.25 (M−H)$^+$; $^1$H NMR (400 MHz, DMSO-d$_6$): δ9.36 (s, 1H), 9.07 (s, 1H), 8.93 (s, 1H), 8.35 (s, 1H), 7.67 (d, J=9.2 Hz, 2H), 7.38 (s, 1H), 7.16 (d, J=9.2 Hz, 1H), 7.08 (m, 1H), 6.93 (d, J=9.2 Hz, 2H), 6.39 (s, 1H), 4.96 (m, 1H), 3.43 (m, 2H), 3.34 (m, 2H), 3.16 (m, 4H), 2.75 (s, 1H), 2.46 (m, 2H), 2.04 (m, 4H), 1.69 (m, 2H).

Example 113

The Preparation of 8-(3-chlorophenylamino)-9-cyclopentyl-2-(4-(4-methylpiperazin-1-yl)phenylamino)-9H-purine

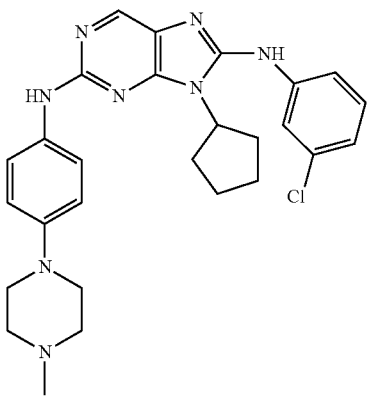

8-52

Compound 5-9 (2.2 g) was dissolved into dichloromethane (70 ml). To the mixture were successively added EDCI (2.7 g), N,N-diisopropylethylamine (2.5 ml), and 3-chlorophenyl isothiocyanate (1.42 g). The mixture was stirred at room temperature for half an hour, and refluxed for 10 hours. TLC detection indicated the completion of the reaction of the starting material 5-9. After cooling the mixture, purification was conducted by a column chromatography to obtain a pale red solid in a yield of 71.7%. ESI-MS (m/z, %) 503.25 (M−H)$^+$; $^1$H NMR (400 MHz, DMSO-d$_6$): δ9.38 (s, 1H), 9.13 (s, 1H), 8.44 (s, 1H), 8.11 (s, 1H), 7.75 (d, J=8.0 Hz, 1H), 7.65 (d, J=8.4 Hz, 2H), 7.35 (m, 1H), 7.02 (m, 1H), 6.94 (d, J=8.8 Hz, 2H), 5.01 (m, 1H), 3.43 (m, 4H), 3.10 (m, 4H), 2.82 (s, 3H), 2.45 (m, 2H), 2.05 (m, 4H), 1.70 (m, 2H) ppm.

Example 114

The Preparation of 8-(3-methylphenylamino)-9-cyclopentyl-2-(4-(4-methylpiperazin-1-yl)phenylamino)-9H-purine

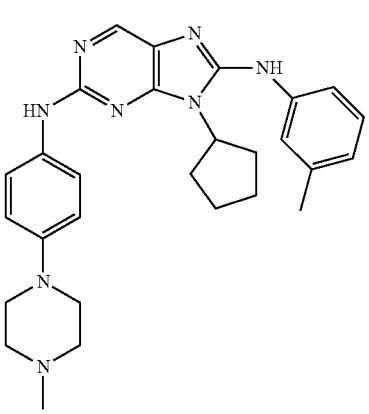

8-53

Compound 5-9 (2.1 g) was dissolved into dichloromethane (90 ml). To the mixture were successively added EDCI (2.3 g), N,N-diisopropylethylamine 2.1 ml), and 3-methylphenyl isothiocyanate (1.0 g). The mixture was stirred at room temperature for half an hour, and refluxed for 10 hours. TLC detection indicated the completion of the reaction of the starting material 5-9. After cooling the mixture, purification was conducted by a column chromatography to obtain a pale red solid in a yield of 72.7%. ESI-MS (m/z, %) 483.25 (M−H)$^+$; $^1$H NMR (400 MHz, DMSO-d$_6$): δ9.08 (s, 1H), 9.02 (s, 1H), 8.37 (s, 1H), 7.68-7.62 (m, 4H), 7.22 (m, 1H), 6.93 (d, J=8.8 Hz, 2H), 6.80 (d, J=7.6 Hz, 1H), 4.99 (m, 1H), 3.67 (m, 2H), 3.44 (m, 2H), 3.03 (m, 4H), 2.81 (s, 3H), 2.45 (m, 2H), 2.31 (s, 3H), 2.04 (m, 4H), 1.69 (m, 2H) ppm.

Example 115

The Preparation of 8-(3,5-dichlorophenylamino)-9-cyclopentyl-2-(4-(4-methylpiperazin-1-yl)phenylamino)-9H-purine

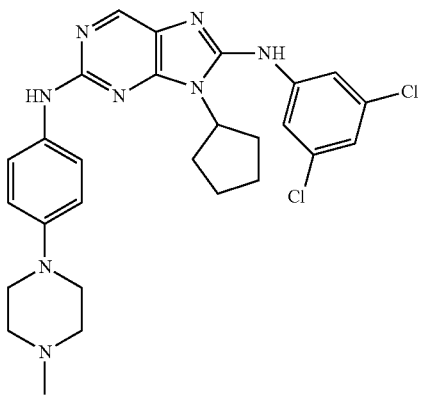

8-54

Compound 5-9 (2.55 g) was dissolved into dichloromethane (90 ml). To the mixture were successively added EDCI (2.67 g), N,N-diisopropylethylamine 2.7 ml), and 3,5-dichlorophenyl isothiocyanate (1.7 g). The mixture was stirred at room temperature for half an hour, and refluxed for 10 hours. TLC detection indicated the completion of the reaction of the starting material 5-9. After cooling the mixture, purification was conducted by a column chromatography to obtain a pale red solid in a yield of 73.7%. ESI-MS (m/z, %) 537.25 (M−H)⁺; $^1$H NMR (400 MHz, DMSO-$d_6$): δ9.40 (s, 1H), 9.08 (s, 1H), 8.48 (s, 1H), 7.97 (s, 1H), 7.60 (d, J=8.8 Hz, 2H), 7.21 (m, 2H), 6.99 (m, 2H), 4.90 (m, 1H), 3.12 (m, 2H), 3.04 (m, 2H), 2.54 (m, 4H), 2.21 (m, 4H), 2.04 (s, 3H), 1.67 (m, 2H), 1.19 (m, 2H) ppm.

Example 116

The Preparation of 8-(2,5-difluorophenylamino)-9-cyclopentyl-2-(4-(4-methylpiperazin-1-yl)phenylamino)-9H-purine

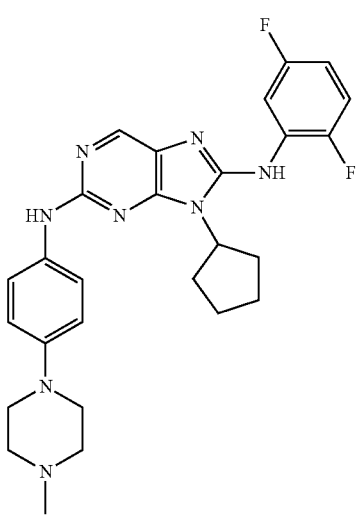

8-55

Compound 5-9 (2.7 g) was dissolved into dichloromethane (100 ml). To the mixture were successively added EDCI (2.8 g), N,N-diisopropylethylamine (3 ml), and 2,5-difluorophenyl isothiocyanate (1.5 g). The mixture was stirred at room temperature for half an hour, and refluxed for 10 hours. TLC detection indicated the completion of the reaction of the starting material 5-9. After cooling the mixture, purification was conducted by a column chromatography to obtain a pale red solid in a yield of 70.6%. ESI-MS (m/z, %) 505.25 (M−H)⁺; $^1$H NMR (400 MHz, DMSO-$d_6$): δ9.16 (s, 1H), 9.06 (s, 1H), 8.43 (s, 1H), 7.91 (m, 1H), 7.56 (m, 2H), 7.32 (m, 2H), 6.91 (m, 3H), 4.92 (m, 1H), 3.45 (m, 4H), 3.23-3.03 (m, 4H), 2.80 (s, 3H), 2.42 (m, 2H), 2.03 (m, 4H), 1.68 (m, 2H) ppm.

Example 117

The Preparation of 8-phenylamino-9-cyclopentyl-2-(4-(2-methoxyethoxy)phenylamino)-9H-purine

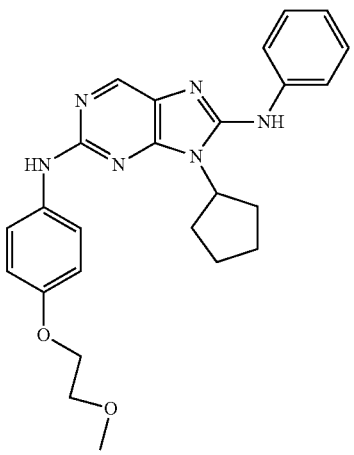

8-56

Compound 5-22 (3.2 g) was dissolved into dichloromethane (90 ml). To the mixture were successively added EDCI (3.6 g), N,N-diisopropylethylamine 3.3 ml), and phenyl isothiocyanate (1.52 g). The mixture was stirred at room temperature for half an hour, and refluxed for 10 hours. TLC detection indicated the completion of the reaction of the starting material 5-9. After cooling the mixture, purification was conducted by a column chromatography to obtain a pale red solid in a yield of 75.3%. ESI-MS (m/z, %) 443.25 (M−H)⁻. $^1$H NMR (400 MHz, DMSO-$d_6$): δ9.20 (s, 1H), 9.06 (s, 1H), 8.36 (s, 1H), 7.86 (d, J=9.6 Hz, 2H), 7.65 (d, J=8.0 Hz, 2H), 7.34 (m, 2H), 6.97 (m, 1H), 6.85 (d, J=8.0 Hz, 2H), 5.05 (m, 1H), 4.04 (m, 2H), 3.64 (m, 2H), 3.31 (s, 3H), 2.43 (m, 2H), 2.03 (m, 4H), 1.68 (m, 2H) ppm.

Example 118

The Preparation of 8-(2,4,5-trichlorophenylamino)-9-cyclopentyl-2-(4-(4-methyl piperazin-1-yl)phenylamino)-9H-purine

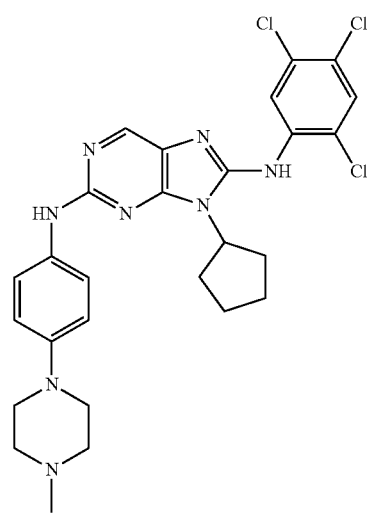

8-57

Compound 5-9 (2.1 g) was dissolved into dichloromethane (60 ml). To the mixture were successively added EDCI (2.15 g), N,N-diisopropylethylamine (2 ml), and 2,4,5-trichlorophenyl isothiocyanate (1.6 g). The mixture was stirred at room temperature for half an hour, and refluxed for 10 hours. TLC detection indicated the completion of the reaction of the starting material 5-9. After cooling the mixture, a solid was separated out and purified by recrystallization to obtain a pale yellow solid in a yield of 74.3%. ESI-MS (m/z, %) 571.25 (M−H)$^+$; $^1$H NMR (400 MHz, DMSO-d$_6$): δ9.09 (s, 1H), 9.01 (s, 1H), 8.27 (s, 1H), 7.64 (m, 2H), 7.12 (m, 1H), 6.89 (d, J=8.4 Hz, 2H), 6.78 (d, J=7.2 Hz, 1H), 4.93 (m, 1H), 3.64 (m, 2H), 3.41 (m, 2H), 3.13 (m, 4H), 2.75 (s, 3H), 2.43 (m, 2H), 2.14 (m, 4H), 1.65 (m, 2H) ppm.

Example 119

The Preparation of 8-phenylamino-9-cyclopentyl-2-(4-((4-ethylpiperazin-1-yl)methyl)phenylamino)-9H-purine

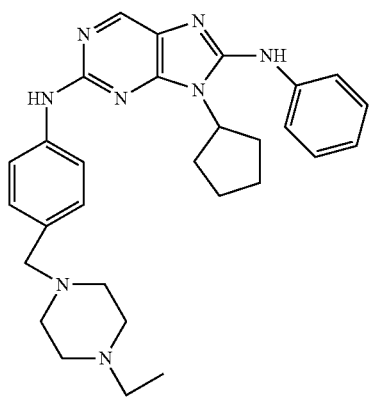

8-59

Compound 5-23 (4.6 g) was dissolved into dichloromethane (100 ml). To the mixture were successively added EDCI (1.67 g), N,N-diisopropylethylamine 1.2 ml), and phenyl isothiocyanate (0.79 g). The mixture was stirred at room temperature for half an hour, and refluxed for 10 hours. TLC detection indicated the completion of the reaction of the starting material 5-25. After cooling the mixture, purification was conducted by a column chromatography to obtain a pale red solid in a yield of 65.1%. ESI-MS (m/z, %) 497.25 (M−H)$^+$. $^1$H NMR (400 MHz, DMSO-d$_6$): δ9.25 (s, 1H), 9.06 (s, 1H), 8.40 (s, 1H), 7.82 (d, J=8.0 Hz, 2H), 7.71 (d, J=8.4 Hz, 2H), 7.34 (m, 2H), 7.15 (d, J=8.4 Hz, 2H), 6.99 (m, 1H), 4.97 (m, 1H), 3.38 (s, 2H), 2.47-2.29 (m, 12H), 2.05 (m, 2H), 1.71 (m, 2H), 0.97 (m, 3H) ppm.

Example 120

The Preparation of 8-phenylamino-9-cyclopentyl-2-(4-((4-methylpiperazin-1-yl)methyl)phenylamino)-9H-purine

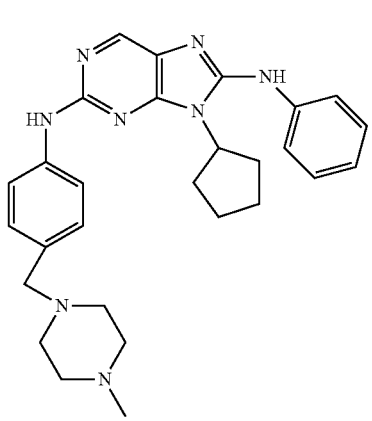

8-59

Compound 5-25 (4.6 g) was dissolved into dichloromethane (100 ml). To the mixture were successively added EDCI (1.74 g), N,N-diisopropylethylamine 1.2 ml), and phenyl isothiocyanate (0.82 g). The mixture was stirred at room temperature for half an hour, and refluxed for 10 hours. TLC detection indicated the completion of the reaction of the starting material 5-25. After cooling the mixture, purification was conducted by a column chromatography to obtain a pale red solid in a yield of 71.8%. ESI-MS (m/z, %) 483.25 (M−H)$^+$. $^1$H NMR (400 MHz, DMSO-d$_6$): δ9.25 (s, 1H), 9.05 (s, 1H), 8.39 (s, 1H), 7.82 (d, J=8.0 Hz, 2H), 7.70 (d, J=8.0 Hz, 2H), 7.33 (m, 2H), 7.15 (d, J=8.0 Hz, 2H), 6.99 (m, 1H), 4.97 (m, 2H), 3.38 (m, 4H), 2.50 (m, 4H), 2.33 (m, 4H), 2.14 (s, 3H), 2.05 (m, 4H), 1.71 (m, 2H) ppm.

Example 121

The Preparation of 8-(2,5-dichlorophenylamino)-9-cyclopentyl-2-(4-(4-methylpiperazin-1-yl)phenylamino)-9H-purine

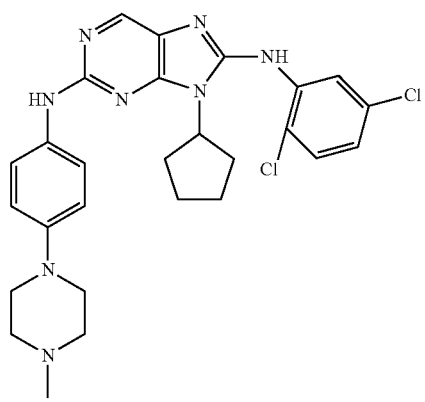

8-60

Compound 5-9 (1.3 g) was dissolved into dichloromethane (60 ml). To the mixture were successively added EDCI (0.8 g), N,N-diisopropylethylamine (2 ml), and 2,5-dichlorophenyl isothiocyanate (0.72 g). The mixture was stirred at room temperature for half an hour, and refluxed for 16 hours. TLC detection indicated the completion of the reaction of the starting material 5-9. Purification was conducted by a column chromatography to obtain a pale yellow solid in a yield of 64.3%. ESI-MS (m/z, %) 537.23 (M–H)$^+$. $^1$H NMR (400 MHz, DMSO-d$_6$): δ9.02 (s, 1H), 8.62 (s, 1H), 8.37 (s, 1H), 7.91 (s, 1H), 7.59 (d, J=8.4 Hz, 2H), 7.49 (d, J=7.6 Hz, 1H), 7.10 (m, 1H), 6.86 (d, J=9.2 Hz, 2H), 4.91 (m, 1H), 3.04 (m, 4H), 2.45 (m, 4H), 2.22 (s, 3H), 2.00 (m, 4H), 1.67 (m, 2H) ppm.

Example 122

The Preparation of 8-(2,6-dichlorophenylamino)-9-cyclopentyl-2-(4-(4-methylpiperazin-1-yl)phenylamino)-9H-purine

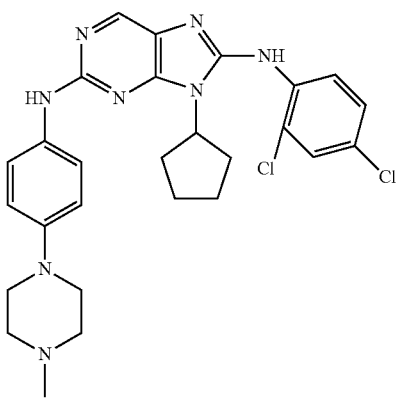

8-61

Compound 5-9 (2.2 g) was dissolved into dichloromethane (40 ml). To the mixture were successively added EDCI (2.3 g), N,N-diisopropylethylamine (5 ml), and 2,4-dichlorophenyl isothiocyanate (1.5 g). The mixture was stirred at room temperature for half an hour, and refluxed for 12 hours. TLC detection indicated the completion of the reaction of the starting material 5-9. Purification was conducted by a column chromatography to obtain a pale yellow solid in a yield of 67.4%. ESI-MS (m/z, %) 537.22 (M–H)$^+$. $^1$H NMR (400 MHz, DMSO-d$_6$): δ9.01 (s, 1H), 8.70 (s, 1H), 8.26 (s, 1H), 7.59 (d, J=8.4 Hz, 4H), 7.39 (s, 1H), 6.86 (d, J=8.8 Hz, 2H), 4.90 (m, 1H), 3.04 (m, 4H), 2.45 (m, 6H), 2.22 (s, 3H), 2.00 (m, 4H), 1.67 (m, 2H) ppm.

Example 123

The Preparation of 8-(3-bromophenylamino)-9-cyclopentyl-2-(4-(4-methylpiperazin-1-yl)phenylamino)-9H-purine

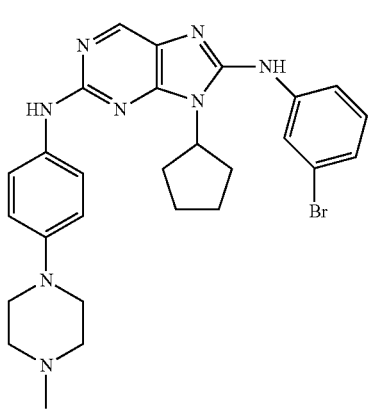

8-62

Compound 5-9 (2.2 g) was dissolved into dichloromethane (40 ml). To the mixture were successively added EDCI (2.3 g), N,N-diisopropylethylamine (5 ml), and 3-bromophenyl isothiocyanate (1.54 g). The mixture was stirred at room temperature for half an hour, and refluxed for 12 hours. TLC detection indicated the completion of the reaction of the starting material 5-9. Purification was conducted by a column chromatography to obtain a pale yellow solid in a yield of 69.5%. ESI-MS (m/z, %) 547.12 (M–H)$^+$. $^1$H NMR (400 MHz, DMSO-d$_6$): δ9.34 (s, 1H), 9.13 (s, 1H), 8.44 (s, 1H), 8.22 (s, 1H), 7.83 (d, J=8.4 Hz, 1H), 7.67 (d, J=8.8 Hz, 2H), 7.29 (m, 1H), 7.15 (d, J=8.0 Hz, 1H), 6.94 (d, J=9.2 Hz, 2H), 5.01 (m, 1H), 3.65 (m, 4H), 3.28 (m, 4H), 2.81 (s, 3H), 2.45 (m, 2H), 2.05 (m, 4H), 1.70 (m, 2H) ppm.

Example 124

The Preparation of 8-phenylamino-9-cyclohexylmethyl-2-(4-(4-methylpiperazin-1-yl)phenylamino)-9H-purine

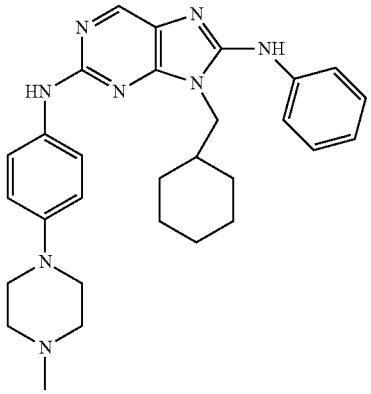

8-63

Compound 5-23 (2.0 g) was dissolved into dichloromethane (25 ml). To the mixture were successively added EDCI (1.92 g), N,N-diisopropylethylamine (2.25 ml), and phenyl isothiocyanate (0.82 g). The mixture was stirred at room temperature for half an hour, and refluxed for 10 hours. TLC detection indicated the completion of the reaction of the starting material 5-23. After cooling the mixture, purification was conducted by a column chromatography to obtain a pale red solid in a yield of 66.2%. ESI-MS (m/z, %) 497.26 (M−H)$^+$. $^1$H NMR (400 MHz, DMSO-d$_6$): δ9.04 (s, 1H), 8.59 (s, 1H), 8.30 (s, 1H), 7.81 (d, J=8.4 Hz, 2H), 7.65 (d, J=8.8 Hz, 2H), 7.31 (m, 2H), 6.88 (m, 1H), 6.75 (d, J=8.4 Hz, 2H), 3.78 (m, 2H), 3.05 (m, 4H), 1.82-1.54 (m, 7H), 1.36-1.18 (m, 4H), 1.12-1.00 (m, 2H).

Assay
Biological Assessment
Assay 1: The Test of the Arylamino Purine Derivatives for the Kinase Inhibitory Activity The object of this assay was to test the inventive compounds for the kinase inhibitory activity in vitro. In this assay, an isotopic labeling method was used to label the γ phosphate group on ATP. EGFR (including wild type, L858R mutant type and L858R/T790M double mutant type), VEGFR2, ALK, BTK, c-KIT, c-SRC, MET, PDGFRα and FLT3 kinases were tested in vitro for the activity inhibition. Staurosporine was used as a reference molecule (or referred to as a positive control). The kinase inhibitory activities of the tested compounds were expressed in the IC$_{50}$ value (half inhibition concentration) or the kinase activity inhibitory rate by the tested compounds at 10 μM. The IC$_{50}$ value can be obtained by the calculation of the inhibitory rates at a series of different concentrations of the tested compounds.

1. Materials
20 mM 3-(N-morpholinyl)propylsulfonic acid (MOPS);
1 mM Ethylenediaminetetraacetic acid (EDTA);
0.01% Polyethylene glycol lauryl ether (Brij-35);
5% Glycerol;
0.1% Mercaptoethanol;
1 mg/ml Bovine serum albumin (BSA);
10 mM Manganous dichloride solution (MnCl2);
0.1 mg/ml Glutamic acid/tyrosine (4:1) polymerized polypeptide (poly(Glu,Tyr)4:1) (the substrate for wild type and L858R mono mutant type EGFRs, c-KIT and PDGFRα);
250 μM polypeptide GGMEDIYFEFMGGKKK (the substrate for L858R/T790M double mutant type EGFR);
250 μM polypeptide KKKSPGEYVNIEFG (the substrate for ALK and MET);
250 μM polypeptide KVEKIGEGTY GVVYK (the substrate for BTK and c-SRC);
0.33 mg/ml myelin basic protein (the substrate for VEGFR2);
50 μM EAIYAAPFAKKK (the substrate for FLT3);
10 mM a solution of magnesium acetate and γ-$^{33}$ P-ATP;
Terminating buffer solution (3% buffer solution of phosphate salt);
Washing buffer solution (75 mM phosphate solution);
Methanol;
Filtermat A membrane;
EGFRs (including wild type, L858R mono mutant type and L858R/T790M double mutant type EGFRs), VEGFR2, ALK, BTK, c-KIT, c-SRC, MET, PDGFRα, FLT3 kinase, and the tested compounds.

2. Procedure
To a reaction tube were successively added the buffer solution (8 mM MOPS, pH 7.0, 0.2 mM EDTA, 10 mM MnCl$_2$), the kinase to be tested (5-10 mU) (EGFR/ALK/BTK/c-KIT/c-SRC/MET/PDGFRα/VEGFR2), the substrate for the kinase to be tested (a reference material), 10 mM of the solution of magnesium acetate and γ-$^{33}$ P-ATP, and different concentrations of the tested compounds. The reaction was started by adding MgATP (the final concentration of ATP is the Km value of the corresponding kinase, i.e., 10 μM for EGFR Wild Type, 200 μM for EGFR L858R, 45 μM for EGFR L858R/T790M, 200 μM for ALK, 200 μM for BTK, 200 μM for c-KIT, 90 μM for VEGFR2, 200 μM for c-SRC, 45 μM for MET, 120 μM for PDGFRα, and 200 μM for FLT3), and incubated at room temperature for 40 minutes. The reaction was terminated with 54 of the 3% phosphate buffer solution. 10 μL of the reaction liquid was titrated on the Filtermat A membrane. The membrane was washed with 75 mM of the phosphate solution thrice (5 minutes each time), and then with methanol once, and finally dried. The membrane was subjected to a scintillation counting. The value of the scintillation counting reflected the phosphorylation level of the substrate and therefore could characterize the inhibition of the kinase activity.

3. Results
Through the above procedures, the inhibitory activities of the present compounds were tested for the kinases EGFRs (comprising wild type, L858R mutant type and L858R/T790M double mutant type), VEGFR2, ALK, BTK, c-KIT, c-SRC, MET, PDGFRα, and FLT3. The kinase inhibitory activities (IC$_{50}$ values) of the tested compounds for EGFRs (comprising wild type, L858R mutant type and L858R/T790M double mutant type) and VEGFR2 are shown in Table 1. The activity inhibition ratio (%) of the tested compounds at 10 μM for the kinases ALK, BTK, c-KIT, c-SRC, MET, PDGFRα, and FLT3 are shown in Table 2.

The results indicated that the tested compounds had strong inhibitory activities on the wild type, L858R mutant type and L858R/T790M double mutant type EGFRs, and some of the tested compounds also had good inhibitory activities on VEGFR2, ALK, BTK, c-KIT, c-SRC, MET, PDGFRα, FLT3 kinases.

TABLE 1

| Tested Compounds | EGFR(IC$_{50}$, μM) | | | VEGFR2(IC$_{50}$, μM) |
|---|---|---|---|---|
| | Wild Type | L858R | L858R/T790M | |
| 8-1 | 0.003 | 0.008 | 0.090 | >1.000 |
| 8-2 | 0.002 | 0.001 | <0.001 | >1.000 |
| 8-3 | 0.025 | 0.060 | 0.245 | >1.000 |
| 8-4 | 0.030 | 0.018 | 0.046 | >1.000 |
| 8-5 | 0.004 | 0.005 | 0.006 | >1.000 |
| 8-6 | 0.001 | 0.0004 | 0.018 | >1.000 |
| 8-7 | 0.007 | 0.001 | 0.128 | >1.000 |
| 8-9 | <0.001 | 0.0004 | 0.006 | >1.000 |
| 8-10 | 0.005 | 0.005 | 0.046 | >1.000 |
| 8-11 | 0.007 | 0.004 | 0.005 | 0.140 |
| 8-12 | 0.004 | 0.003 | 0.003 | 0.050 |
| 8-13 | 0.004 | 0.003 | 0.009 | >1.000 |
| 8-15 | 0.003 | 0.001 | 0.015 | 0.004 |
| 8-16 | 0.003 | 0.001 | 0.012 | >1.000 |
| 8-17 | 0.004 | 0.001 | 0.004 | >1.000 |
| 8-18 | 0.030 | 0.005 | 0.057 | 0.021 |
| 8-19 | 0.005 | 0.004 | 0.004 | >1.000 |
| 8-21 | 0.011 | 0.005 | 0.005 | >1.000 |
| 8-22 | 0.117 | 0.010 | 0.087 | >1.000 |
| 8-23 | 0.007 | 0.002 | 0.041 | >1.000 |
| 8-24 | 0.012 | 0.003 | 0.522 | >1.000 |
| 8-25 | 0.029 | 0.005 | 0.458 | >1.000 |
| 8-26 | <0.001 | 0.0004 | <0.001 | 0.007 |
| 8-27 | 0.034 | 0.005 | 0.054 | 0.009 |
| 8-29 | 0.031 | 0.004 | 0.064 | >1.000 |
| 8-30 | 0.015 | 0.005 | 0.228 | >1.000 |
| 8-38 | 0.002 | 0.0006 | 0.037 | >1.000 |

TABLE 2

| Tested Compounds | The kinase activity inhibitory rate (%) by the tested compounds at 10 μM | | | | | | |
|---|---|---|---|---|---|---|---|
| | ALK | BTK | c-KIT | c-SRC | MET | PDGFRα | FLT3 |
| 8-1 | 23 | 46 | 26 | 11 | 83 | 43 | 85 |
| 8-2 | 63 | 98 | 90 | 99 | 100 | 84 | 78 |
| 8-3 | 16 | 11 | 54 | 67 | 2 | 20 | 0 |
| 8-4 | 64 | 45 | 23 | 12 | 67 | 16 | 43 |
| 8-5 | 54 | 78 | 54 | 32 | 64 | 19 | 35 |
| 8-6 | 15 | 46 | 21 | 82 | 14 | 39 | 56 |
| 8-7 | 61 | 12 | 8 | 28 | 0 | 9 | 0 |
| 8-9 | 36 | 88 | 96 | 98 | 67 | 88 | 76 |
| 8-10 | 45 | 32 | 3 | 23 | 64 | 87 | 87 |
| 8-11 | 33 | 77 | 67 | 98 | 93 | 58 | 67 |
| 8-12 | 80 | 78 | 82 | 98 | 93 | 55 | 56 |
| 8-13 | 78 | 45 | 87 | 31 | 100 | 90 | 89 |
| 8-15 | 40 | 95 | 94 | 97 | 45 | 94 | 90 |
| 8-16 | 17 | 57 | 62 | 90 | 93 | 39 | 45 |
| 8-17 | 35 | 100 | 89 | 99 | 52 | 72 | 86 |
| 8-18 | 13 | 56 | 76 | 93 | 7 | 60 | 75 |
| 8-19 | 90 | 71 | 12 | 97 | 97 | 34 | 43 |
| 8-21 | 97 | 92 | 101 | 98 | 99 | 100 | 78 |
| 8-22 | 70 | 63 | 10 | 98 | 69 | 43 | 87 |
| 8-23 | 3 | 30 | 26 | 83 | 1 | 28 | 68 |
| 8-24 | 8 | 14 | 48 | 75 | 0 | 29 | 75 |
| 8-25 | 13 | 45 | 8 | 78 | 0 | 21 | 32 |
| 8-26 | 71 | 99 | 94 | 99 | 86 | 95 | 86 |
| 8-27 | 30 | 74 | 93 | 98 | 36 | 68 | 83 |
| 8-29 | 15 | 60 | 36 | 97 | 50 | 42 | 99 |
| 8-30 | 8 | 25 | 0 | 67 | 0 | 21 | 43 |
| 8-38 | 22 | 93 | 63 | 93 | 74 | 55 | 86 |

Assay 2: The Test of the Arylamino Purine Derivatives for the In-Vitro Tumor Cell Proliferation Inhibition The object of this assay was to test the inventive compounds for the inhibitory activity of in-vitro tumor cell proliferation. The MTT (tetreamethyl-azo-zole-salt) colorimetric method was used in this assay.

1. Materials 1.1 Main Agents

RPMI-1640, fetal bovine serum, pancreatin and the like were purchased from Gibco BRL Company (Invitrogen Corporation, USA). The IMDM culture medium was purchased from ATCC (American Type Culture Collection). Tetreamethyl-azo-zole-salt (MTT) and dimethylsulfoxide (DMSO) were the products available from Sigma Company (USA). The arylamino purine derivatives were synthesized by the present inventors. In this in-vitro assay, 100% DMSO was formulated into a 10 mM stocking solution and preserved in a freezer at −20° C. and in dark place for use. The stocking solution was diluted with a complete culture solution to a desired concentration immediately before use.

1.2 Cell Lines and their Culturing

Human non-small cell lung carcinoma cell strains HCC827, PC-9, H1975 (EGFR L858R/T790M mutation) and H292 (EGFR WT), and other tumor type cell strains, including human acute myelogenous leukemia cell strain MV4-11, human chronic granulocytic leukemia cell strain K562, human squamous cell carcinoma cell strain A431, human breast carcinoma cell strains MDA-MB-468 and BT 474, human colon cancer cell strains SW480, HCT116 and SW620, human liver cancer cell strain Hep G2, human gastric cancer cell strain MK-45, and human malignant melanoma cell strain A375 used in this assay were all purchased from ATCC company, USA and kept in the laboratory. All of the above-mentioned non-small cell lung carcinoma cell strains and the breast carcinoma cell strain BT 474 were cultured with a RPMI-1640 complete culture medium containing 10% fetal bovine serum, 100 U/ml penicillin and 100 μg/ml streptomycin under 5% CO2 and at 37° C. The other cell strains were cultured with a DMEM complete culture medium containing 10% fetal bovine serum (having a MV4-11 cell content of 20%), 100 U/ml penicillin and 100 μg/ml streptomycin under 5% CO2 and 37° C.

2. Procedure

A cell suspension having a cell concentration of $1$-$2 \times 10^4$ cells/ml was treated with a complete cell culture solution to adjust the cell concentration, wherein the cell concentrations for HCC827 and MV4-11 were adjusted to $6 \times 10^4$ cells/ml and $1 \times 10^5$ cells/ml respectively. The cell suspension was inoculated in a 96-well plate with 200 μl cell suspension/well and cultured overnight. Next day, the supernatant was drawn off and discarded. Then, the cells were treated with the tested compounds in a gradient concentration respectively. In the meanwhile, a negative control group free of the drug substance and an isovolumetric solvent control group (having a DMSO concentration of 1%) were used. The triplicate wells were used for each of dose groups. The culturing was conducted at 37° C. under 5% CO2. After 72 hours, 200 MTT agent having a concentration of 5 mg/ml was added to each of wells. The culturing was further conducted for 2-4 hours. The supernatant was discarded. Then 150 μl DMSO was added to each of wells. The contents in the well were mixed homogenously by oscillation for 15 minutes. The absorbance (A) value was measured with a microplate reader at λ=570 nm (the A value is in the direct proportion to the number of living cells) and averaged. The relative cell proliferation inhibitory rate is $(A_{570\ control\text{-}group} - A_{570\ dose\text{-}group})/A_{570\ control\text{-}group} \times 100\%$. The assay was repeated for at least three times. The data was expressed as number average. The statistical data were analyzed using t-test. $P<0.05$ was considered significant. The cell proliferation inhibition of the following compounds was expressed as IC50 or inhibitory rate.

3. Results

According to the above-mentioned procedure, human non-small cell lung carcinoma cell strains HCC827, PC-9 (EGFR delE746-A750 deletion mutation), H1975 (EGFR L858R/T790M mutation) and H292 (EGFR WT), and other tumor type cell strains, including human acute myelogenous leukemia cell strain MV4-11, human chronic granulocytic leukemia cell strain K562, human squamous cell carcinoma cell strain A431, human breast carcinoma cell strains MDA-MB-468 and BT 474, human colon cancer cell strains SW480, HCT116 and SW620, human liver cancer cell strain Hep G2, human gastric cancer cell strain MK-45, and human malignant melanoma cell strain A375 were subjected to the proliferation inhibition activity test.

The proliferation inhibitory activities ($IC_{50}$) of the tested compounds for human non-small cell lung carcinoma cell strains HCC827, PC-9 and H1975 are shown in the table 3. The proliferation inhibitory activities ($IC_{50}$) of the tested compounds for human tumor cell strains MV4-11, K562, A431, MDA-MB-468, BT474, SW480, HCT116, HepG2, SW620, MK-45, H292 and A375 are shown in the tables 4 and 5. The results indicated that the tested compounds had strong inhibitory activities on the cell strains HCC827 and PC-9 which were sensitive to Gefitinib; some of the tested compounds also had a good inhibitory activity on the cell strain H1975 which was resistant to Gefitinib; and in addition, some of the tested compounds also had good inhibitory activities on the other tumor cell strains including human MV4-11, K562, A431, MDA-MB-468, BT474, SW480, HCT116, HepG2, SW620, MK-45, H292, A375 and the like.

TABLE 3

| Tested Compounds | HCC827 (IC$_{50}$, μM) | PC-9 (IC$_{50}$, μM) | H1975 (IC$_{50}$, μM) |
|---|---|---|---|
| 8-1 | 0.0020 | 0.1047 | 7.6 |
| 8-2 | 0.0013 | 0.5580 | >10 |
| 8-3 | >1 | >1 | >10 |
| 8-4 | 0.0030 | 0.0680 | 0.86 |
| 8-5 | 0.0013 | 0.5580 | >10 |
| 8-6 | 0.0002 | 0.0137 | >10 |
| 8-7 | 0.0075 | 0.0121 | >10 |
| 8-9 | 0.0042 | 0.0723 | >10 |
| 8-10 | 0.0001 | 0.0009 | 2 |
| 8-11 | 0.0002 | 0.0002 | 1.726 |
| 8-12 | 0.0002 | 0.0002 | 1.929 |
| 8-13 | 0.0002 | 0.0003 | 2 |
| 8-15 | 0.0002 | 0.0064 | >10 |
| 8-16 | 0.0002 | 0.0168 | 1.822 |
| 8-17 | 0.0002 | 0.0025 | 1.904 |
| 8-18 | 0.1172 | 0.0349 | >10 |
| 8-19 | 0.9116 | 0.4591 | 7.32 |
| 8-21 | 0.0516 | 0.0859 | 7.312 |
| 8-22 | >1 | 2.7947 | >10 |
| 8-23 | 0.0002 | 0.0359 | >10 |
| 8-24 | 0.0002 | 0.0060 | >10 |
| 8-25 | 0.0528 | 0.2582 | >10 |
| 8-26 | 0.0011 | 0.0002 | 0.369 |
| 8-27 | 0.0823 | 0.1149 | >10 |
| 8-29 | 0.0072 | 0.0100 | >10 |
| 8-30 | 0.4828 | 0.0551 | >10 |
| 8-34 | 0.0631 | 0.4199 | 6.3076 |
| 8-35 | 0.0002 | 0.0015 | 1.5162 |
| 8-36 | 0.0002 | 0.0209 | 0.8518 |
| 8-37 | 0.1297 | 0.3476 | >10 |
| 8-38 | 0.0005 | 0.0007 | 0.6445 |
| 8-41 | 0.0165 | 0.2092 | 0.5013 |
| 8-42 | 4.2614 | 3.3210 | >10 |
| 8-43 | 0.0003 | 0.0519 | 0.2309 |
| 8-44 | 0.0003 | 0.0015 | 0.6947 |
| 8-45 | 0.0002 | 0.0097 | 1.1359 |
| 8-46 | 0.0003 | 0.0035 | 0.7702 |
| 8-47 | 0.0003 | 0.0163 | 0.8844 |
| 8-48 | 0.0002 | 0.0262 | 4.5828 |
| 8-49 | 0.0003 | 0.0002 | 0.3103 |
| 8-50 | 0.0003 | 0.0035 | 0.1822 |
| 8-51 | 0.0002 | 0.0095 | 0.6302 |
| 8-52 | 0.0003 | 0.0006 | 0.2714 |
| 8-53 | 0.0002 | 0.0002 | 0.5516 |
| 8-54 | 0.0063 | 0.2045 | 1.7011 |
| 8-55 | 0.0002 | 0.0010 | 0.3228 |
| 8-56 | 0.0006 | 0.0070 | >10 |
| 8-57 | 0.0280 | 0.1773 | >10 |
| 8-58 | 0.0002 | 0.0181 | 0.2521 |
| 8-59 | 0.0002 | 0.0021 | 0.2482 |
| 8-60 | 0.0002 | 0.0117 | 0.4731 |
| 8-61 | 0.0143 | 0.1165 | 4.2103 |
| 8-62 | 0.0002 | 0.0091 | 0.3920 |

TABLE 4

| Tested Compounds | MV4-11 (IC$_{50}$, μM) | K562 (IC$_{50}$, μM) | A431 (IC$_{50}$, μM) | MDA-MB-468 (IC$_{50}$, μM) | BT474 (IC$_{50}$, μM) | SW480 (IC$_{50}$, μM) |
|---|---|---|---|---|---|---|
| 8-1 | 0.089 | 1.078 | 2.059 | 2.059 | 2.132 | 5.725 |
| 8-2 | 1.768 | 3.734 | 9.293 | 6.134 | 1.859 | >10 |
| 8-3 | >10 | >10 | 12.9 | >10 | >10 | >10 |
| 8-4 | 9.772 | 1.391 | 1.986 | 4.766 | 0.635 | >10 |
| 8-5 | 1.768 | 3.734 | 9.293 | 6.134 | 1.859 | >10 |
| 8-6 | 2.845 | 7.354 | 2.388 | 2.985 | 0.597 | >10 |
| 8-7 | >10 | >10 | >10 | >10 | 5.818 | >10 |
| 8-9 | 0.235 | 0.143 | 1.527 | 1.321 | 1.032 | >10 |
| 8-10 | 0.102 | 0.106 | 1.582 | 0.7 | 0.226 | >10 |
| 8-11 | 3.755 | 0.366 | 7.671 | 1.189 | 0.575 | >10 |
| 8-12 | 1.711 | 0.221 | 2.572 | 3.215 | 2.143 | >10 |
| 8-13 | 0.512 | 0.086 | 1.293 | 2.101 | 0.202 | >10 |
| 8-15 | 0.197 | 0.303 | 9.397 | 2.301 | 1.918 | >10 |
| 8-16 | 4.799 | 2.523 | 5.876 | 1.959 | 1.371 | 6.481 |
| 8-17 | 0.684 | 0.003 | 8.464 | 0.783 | 0.635 | >10 |
| 8-18 | 0.183 | 1.221 | 6.348 | 3.174 | 2.116 | >10 |
| 8-19 | 4.778 | 2.791 | 9.316 | 9.981 | 4.991 | >10 |
| 8-21 | 0.279 | 1.335 | 5.722 | 0.89 | 1.589 | >10 |
| 8-22 | 0.283 | 0.921 | 5.52 | 1.725 | 1.725 | >10 |
| 8-23 | 0.241 | 5.198 | 7.037 | 5.221 | 6.81 | >10 |
| 8-24 | 0.288 | 1.422 | 9.65 | 9.65 | 2.412 | >10 |
| 8-25 | 7.896 | >10 | >10 | >10 | 9.988 | >10 |
| 8-26 | 0.093 | 0.12 | 1.046 | 0.299 | 0.107 | 3.438 |
| 8-27 | 0.088 | 0.777 | 2.35 | 1.959 | 1.175 | 2.597 |
| 8-29 | 0.004 | 0.24 | 9.018 | 8.116 | 2.255 | >10 |
| 8-30 | 7.962 | 5.756 | >10 | >10 | 4.458 | >10 |
| 8-34 | 0.1248 | 1.5971 | 2.5734 | 3.2589 | 2.6282 | 9.9542 |
| 8-35 | 0.1353 | 0.2322 | 0.6351 | 1.9193 | 0.1919 | 5.9306 |
| 8-36 | 0.0010 | 0.0760 | 0.4630 | >10 | 0.6389 | 8.6758 |
| 8-37 | 0.1016 | 0.8882 | >10 | >10 | 4.5220 | >10 |
| 8-38 | 0.7297 | 0.2685 | 0.1790 | 0.2805 | 1.6809 | >10 |
| 8-41 | 1.9710 | 0.1460 | 2.7386 | 4.4875 | 2.0921 | 5.3955 |
| 8-42 | 6.6387 | 0.9223 | 2.2395 | 1.7005 | 5.1014 | >10 |
| 8-43 | 0.0212 | 0.1225 | 0.4844 | 1.0296 | 1.8265 | 5.7535 |
| 8-44 | 1.1377 | 0.0965 | 0.4089 | 2.6656 | 0.6815 | 6.1586 |
| 8-45 | 0.0594 | 0.2184 | 1.8855 | 2.8739 | 0.8702 | 7.7514 |
| 8-46 | 4.6852 | 0.2505 | 0.4263 | 0.7511 | 0.7917 | 4.0051 |
| 8-47 | 0.2242 | 0.0972 | 0.2989 | 3.1902 | 0.5542 | 5.5316 |
| 8-48 | 0.5831 | 0.2300 | 0.7879 | 2.1296 | 0.5254 | 9.8918 |
| 8-49 | 0.1930 | 0.1207 | 0.5865 | 0.9871 | 2.6675 | 5.0433 |
| 8-50 | 0.0644 | 0.0305 | 0.0829 | 0.2072 | 2.1632 | 2.7164 |
| 8-51 | 0.0036 | 0.0113 | 0.2476 | 0.3508 | 0.7635 | 6.7231 |

TABLE 4-continued

| Tested Compounds | MV4-11 (IC$_{50}$, μM) | K562 (IC$_{50}$, μM) | A431 (IC$_{50}$, μM) | MDA-MB-468 (IC$_{50}$, μM) | BT474 (IC$_{50}$, μM) | SW480 (IC$_{50}$, μM) |
|---|---|---|---|---|---|---|
| 8-52 | 0.6419 | 0.1478 | 0.0796 | 0.7367 | 0.1653 | 4.6233 |
| 8-53 | 0.8986 | 0.0953 | 0.2486 | 0.6216 | 1.5126 | 4.2104 |
| 8-54 | 1.0737 | 0.8627 | 2.0614 | 3.3489 | 3.9647 | 6.7257 |
| 8-55 | 0.6823 | 0.0880 | 0.1982 | 2.1800 | 0.4558 | 5.3193 |
| 8-56 | 4.4271 | >10 | >10 | >10 | >10 | >10 |
| 8-57 | 6.1616 | 0.3521 | 5.7699 | >10 | >10 | 9.7634 |
| 8-58 | 0.1806 | 0.0671 | 0.2416 | 0.7450 | 0.0805 | 5.5452 |
| 8-59 | 0.0998 | 0.1113 | 0.4973 | 6.8377 | 1.1017 | 4.7470 |
| 8-60 | 0.1459 | 0.4510 | 2.0465 | 7.1257 | 1.0240 | 4.2550 |
| 8-61 | 1.6785 | 1.0075 | 5.2634 | 6.1396 | 1.8568 | 8.1211 |
| 8-62 | 0.5772 | 0.1391 | 0.4932 | 0.5553 | 0.1867 | 3.4996 |

TABLE 5

| Tested Compounds | HCT116 (IC$_{50}$, μM) | HEPG2 (IC$_{50}$, μM) | SW620 (IC$_{50}$, μM) | MK45 (IC$_{50}$, μM) | H292 (IC$_{50}$, μM) | A375 (IC$_{50}$, μM) |
|---|---|---|---|---|---|---|
| 8-1 | >10 | >10 | >10 | 6.7960 | 1.3880 | 3.0211 |
| 8-2 | 7.812 | >10 | 5.567 | >1 | 0.8829 | 1.5864 |
| 8-3 | >10 | >10 | >10 | >10 | 1.3039 | >10 |
| 8-4 | >1 | >10 | >1 | 2.1844 | 0.1489 | >10 |
| 8-5 | 7.812 | >10 | 5.567 | >1 | >1 | >1 |
| 8-6 | 3.295 | 2.571 | 2.135 | 0.5398 | 0.1273 | 6.9321 |
| 8-7 | >10 | >10 | >10 | 3.7625 | 0.1377 | 1.3124 |
| 8-9 | 0.518 | >10 | 0.524 | 0.7635 | 0.1596 | 0.5861 |
| 8-10 | 1.091 | 4.797 | 6.056 | >1 | 0.0105 | 1.4891 |
| 8-11 | 1.682 | 11.215 | 1.96 | >1 | 0.0088 | 1.3865 |
| 8-12 | 4.008 | 6.606 | 1.292 | >1 | 0.0107 | 3.0927 |
| 8-13 | 2.543 | 5.962 | 3.675 | >1 | 0.0061 | 0.8384 |
| 8-15 | 2.2 | 7.794 | 2.992 | 0.7095 | 0.2205 | 0.7747 |
| 8-16 | 0.766 | 10.445 | 0.864 | >1 | 0.1293 | 3.1005 |
| 8-17 | 0.813 | >10 | >1 | 0.6642 | 0.0296 | 0.1896 |
| 8-18 | 6.289 | >10 | 4.003 | 1.5206 | 0.5311 | 6.4623 |
| 8-19 | >1 | 5.42 | 1.993 | 1.0055 | 0.3161 | 1.6636 |
| 8-21 | 0.772 | 8.933 | 2.225 | 1.3279 | 1.1603 | 0.7248 |
| 8-22 | 1.829 | >10 | 1.922 | 0.5108 | 1.7251 | 1.2973 |
| 8-23 | >10 | >10 | >10 | 2.7898 | 0.1544 | 3.1756 |
| 8-24 | 1.382 | >10 | >10 | 8.0818 | 0.1713 | 2.4004 |
| 8-25 | >10 | >10 | >10 | 5.3511 | 1.6455 | >10 |
| 8-26 | 0.239 | 6.255 | 0.282 | >1 | 0.0107 | 0.3777 |
| 8-27 | >1 | >1 | >1 | 6.1109 | 4.1856 | 9.7932 |
| 8-29 | 2.48 | >10 | 5.796 | 8.1682 | 0.1804 | 1.8758 |
| 8-30 | >10 | >10 | 4.217 | 5.4680 | 0.2006 | >10 |
| 8-34 | 10.4821 | 8.4627 | >10 | 1.6645 | 1.2331 | 6.5704 |
| 8-35 | 0.6756 | 4.3356 | 2.3031 | 1.1145 | 0.0203 | 3.2455 |
| 8-36 | 1.1223 | 3.5159 | 3.6139 | 1.5518 | 0.0341 | 1.4481 |
| 8-37 | >10 | >10 | >10 | >10 | 5.8524 | >10 |
| 8-38 | 0.4426 | 2.9046 | 0.3700 | 1.7897 | 0.0073 | >10 |
| 8-41 | 5.4311 | 2.1988 | 2.1402 | 3.3432 | 0.2678 | >10 |
| 8-42 | >10 | >10 | >10 | 5.1020 | 0.6734 | 0.4982 |
| 8-43 | 2.5663 | 5.9270 | 5.7535 | 0.2338 | 0.1017 | 1.9069 |
| 8-44 | >10 | >10 | 2.5098 | 1.3528 | 0.0029 | 1.7417 |
| 8-45 | 7.0842 | >10 | 4.9666 | 3.7400 | 0.0139 | 9.2557 |
| 8-46 | 9.0658 | >10 | 3.6194 | 0.4170 | >10 | 0.3999 |
| 8-47 | 6.0851 | 8.4636 | 4.9480 | 1.1820 | 0.0442 | 1.5739 |
| 8-48 | >10 | >10 | 2.9367 | 0.2969 | 0.0185 | 2.0848 |
| 8-49 | 1.4365 | 9.2439 | 1.4365 | 0.5426 | 0.0045 | 1.9811 |
| 8-50 | 2.4678 | 8.2487 | 0.9635 | 0.2176 | >10 | 1.5602 |
| 8-51 | 4.1374 | 8.2150 | 0.7326 | 0.2476 | 0.0223 | 0.5386 |
| 8-52 | 5.9255 | 7.2296 | 1.5690 | 0.4566 | 0.0040 | 0.9736 |
| 8-53 | >10 | >10 | 2.1135 | 0.5594 | 0.0041 | 8.0705 |
| 8-54 | 6.9601 | 5.9796 | 6.6383 | 0.6884 | 0.2791 | 5.5815 |
| 8-55 | 6.5500 | 4.6772 | 2.9748 | 1.7216 | >10 | 2.7686 |
| 8-56 | >10 | >10 | >10 | >10 | 0.0810 | >10 |
| 8-57 | 7.8646 | >10 | 8.3682 | 4.5862 | 0.7518 | >10 |
| 8-58 | 7.4640 | >10 | 1.2504 | 0.5638 | 0.0040 | 0.6604 |
| 8-59 | 5.7188 | >10 | 1.3344 | 0.8081 | 0.0033 | 1.1976 |
| 8-60 | 6.4206 | >10 | 1.2521 | 1.8443 | 0.0545 | 9.3025 |
| 8-61 | >10 | >10 | 5.9796 | 2.4503 | 0.1879 | >10 |
| 8-62 | 3.5197 | 6.8330 | 1.3023 | 0.4371 | 0.0055 | 1.0210 |

Assay 3: The In-Vivo Anti-Tumor Test for Compound 8-10

The object of this assay was to determine the in-vivo anti-tumor effect of the present compound. In this assay, a nude mouse subcutaneously transplanted non-small cell lung carcinoma model was used to test the present compound 8-10 for the in-vivo anti-tumor activity. The used cell strain was human non-small cell lung carcinoma cell strain HCC827.

1. Materials

RPMI-1640, fetal bovine serum, pancreatin and the like were purchased from Gibco BRL company (Invitrogen Corporation, USA); RPMI 1640 culture medium was purchased from ATCC (American Type Culture Collection); human non-small cell lung carcinoma cell strain HCC827 was purchased from ATCC company, USA; and BALB/C nude mice were purchased from Institute of Zoology, Chinese Academy of Sciences.

2. Procedure

BALB/C nude mice, aged 6-8 weeks, were inoculated with HCC827 cell subcutaneously at the posterior segment of rib in a concentration of about $5 \times 10^6$ cells/0.1 ml per mouse. Upon the growth of the tumor up to 200-300 mm$^3$ (about 20 days), mice were grouped (n=6) and administrated intragastrically.

Groups:

Solvent control group: (5% DMSO+1% TWEEN80+94% water);

Gefitinib group: 100 mg/kg q.d.;

Compound 8-10 group: 2 mg/kg q.d.;

Compound 8-10 group: 5 mg/kg q.d.;

Compound 8-10 group: 10 mg/kg q.d.;

Compound 8-10 group: 20 mg/kg q.d.

(Each of drug groups was dissolved in 5% DMSO+1% TWEEN80+94% water).

Observation Indices: the mice were measured every three days for the weight, and the length and width of tumor, and the tumor volume was calculated as length×width$^2$×0.52. The mice were observed for the reactions such as diarrhea, convulsion, exanthema, and substantial weight reduction.

3. Results

Figure 2:
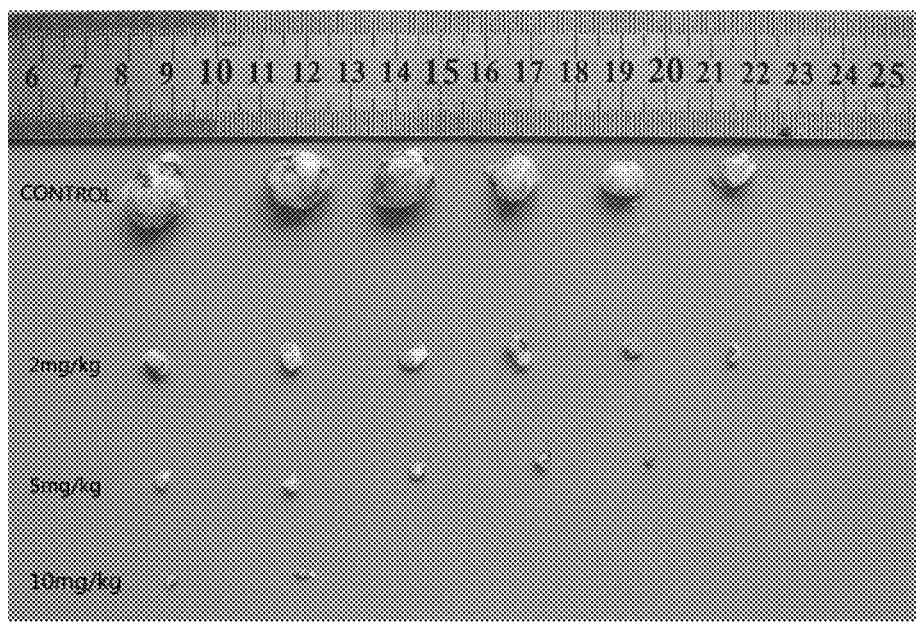
FIG. 2 illustrates the in-vivo anti-tumor effect of Compound 8-10 and provides a photograph of photograph of tumors obtained by dissection after the assay of the nude mouse subcutaneously transplanted human non-small cell lung carcinoma (HCC827 cell strain) model.

The measured tumor growth curves for each of the groups are shown in FIG. 1. The photograph of tumors obtained by dissection after the assay is shown in FIG. 2. The results indicated that the tested compound 8-10 had a substantial in-vivo growth inhibition for the EGFR$^{delE746-A750}$ mutated human non-small cell lung carcinoma cell strain HCC827. Upon administrating in 2 mg/kg q.d. or higher, the tumor growth could be substantially inhibited, or even the tumor could be eliminated. In the course of administration, the nude mice did not show the untoward reactions such as weight reduction, exanthema, and diarrhea, which indicated that under the test doses, the tested compound 8-10 had a low toxicity in the dose range of administration.

Assay 4: The In-Vivo Anti-Tumor Test for Compound 8-29

The object of this assay was to determine the in-vivo anti-tumor effect of the present compound. In this assay, a NOD-SCID mouse subcutaneously transplanted human leukemic solid tumor model was used to test the present compound 8-29 for the in-vivo anti-tumor activity. The used cell strain was human acute myelogenous leukemia cell strain MV4-11.

1. Materials

IMDM, fetal bovine serum, pancreatin and the like were purchased from Gibco BRL company (Invitrogen Corporation, USA); IMDM culture medium was purchased from ATCC (American Type Culture Collection), human leukemia cell strain MV4-11 was purchased from ATCC company, USA; and the NOD-SCID mice were purchased from Laboratory Animal Center, Peking Union Medical College, China.

2. Procedure

NOD-SCID mice, aged 6-8 weeks, were inoculated with MV4-11 cell subcutaneously at the posterior segment of rib in a concentration of about $1 \times 10^7$ cells/0.1 ml per mouse. Upon the growth of the tumor up to 400-500 mm$^3$ (about 20 days), mice were grouped (n=6) and administrated intragastrically.

Groups:

Solvent control group: (5% DMSO+25% PEG400+70% water);

Compound 8-29 group: 5 mg/kg q.d.;

Compound 8-29 group: 10 mg/kg q.d.;

Compound 8-29 group: 20 mg/kg q.d.

(Each of drug groups was dissolved in 5% DMSO+25% PEG400+70% water)

Observation Indices: the mice were measured every three days for the weight, and the length and width of tumor, and the tumor volume was calculated as length×width$^2$×0.52. The mice were observed for the reactions such as diarrhea, convulsion, exanthema, and substantial weight reduction.

3. Results

Figure 3:
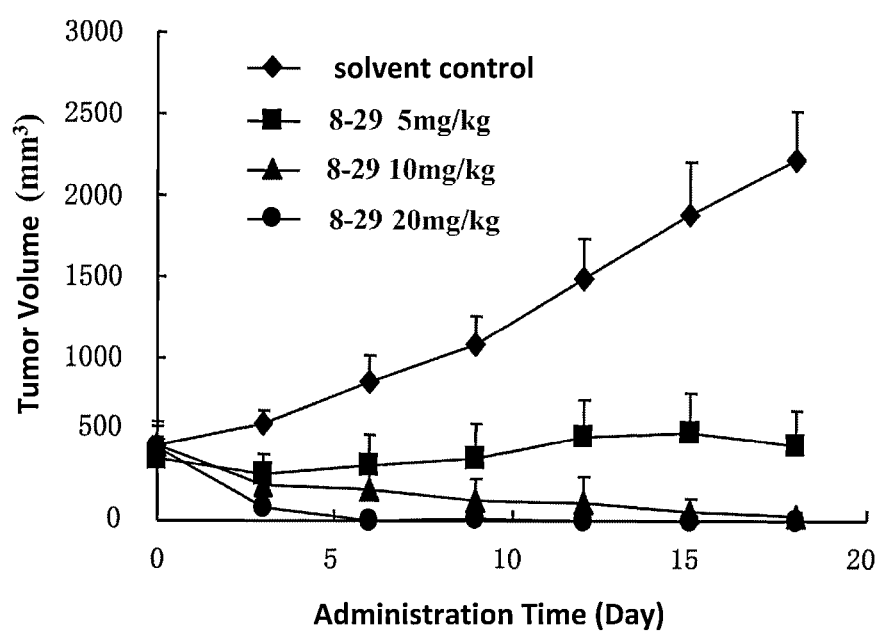
FIG. 3 illustrates the in-vivo anti-tumor effect of Compound 8-29 and provides the tumor growth curves in a nude mouse subcutaneously transplanted human acute myelogenous leukemia (MV4-11 cell strain) model.

The measured tumor growth curves for each of the groups are shown in FIG. 3. The results indicated that the tested compound 8-29 had a substantial in-vivo growth inhibition for the FLT3-ITD mutated human acute myelogenous leukemia cell strain MV4-11. Upon administrating in 5 mg/kg q.d. or higher, the tumor growth could be substantially inhibited, or even the tumor could be eliminated. In the course of administration, the mice did not show the untoward reactions such as weight reduction, exanthema, and diarrhea, which indicated that under the test doses, the tested compound 8-29 had a low toxicity in the dose range of administration.

The invention claimed is:

1. An arylamino purine derivative represented by formula I:

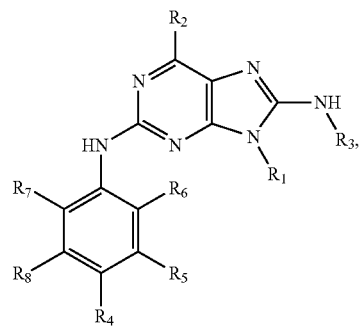

wherein $R_1$ is selected from the group consisting of —H, —C$_m$H$_{(2m+1)}$, C$_3$-C$_7$ cycloalkyl, —C$_m$H$_{(2m+1)}$ substituted by C$_3$-C$_7$ cycloalkyl, and C$_3$-C$_7$ cycloalkyl substituted by —C$_m$H$_{(2m+1)}$;

$R_2$ is selected from the group consisting of —H, —NH$_2$, —OH, —F, —Cl, —Br, —CF$_3$, —C$_m$H$_{(2m+1)}$, —OC$_m$H$_{(2m+1)}$, and —NHC$_m$H$_{(2m+1)}$;

$R_3$ is selected from the group consisting of

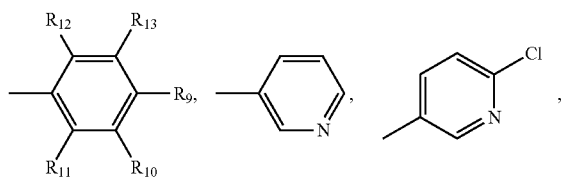

and $C_3$-$C_7$ cycloalkyl;

$R_4$ is selected from the group consisting of

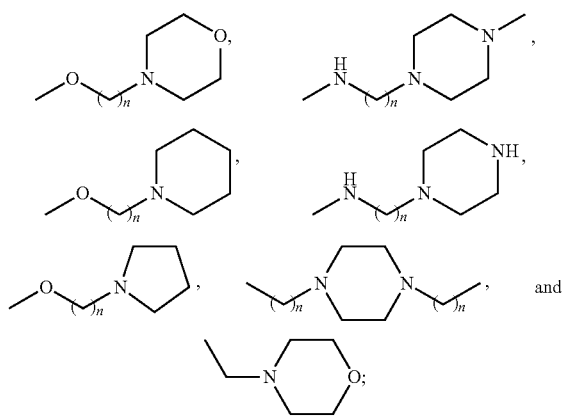

$R_5$-$R_8$ are each independently selected from the group consisting of —H, —F, —Cl, —Br, —CF$_3$, and —OC$_m$H$_{(2m+1)}$;

$R_9$-$R_{13}$ are each independently selected from the group consisting of —H, —F, —Cl, —Br, —CF$_3$, —C$_m$H$_{(2m+1)}$, —OC$_m$H$_{(2m+1)}$,

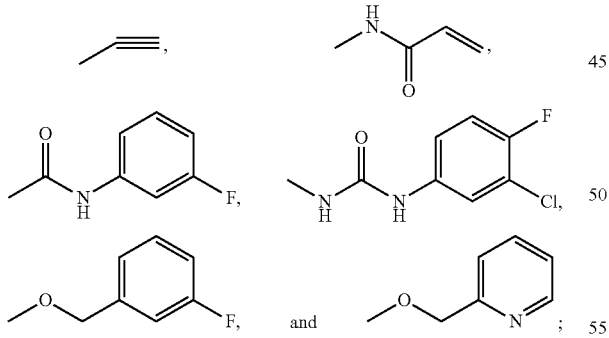

m=1-8; and
n=0-4.

2. The arylamino purine derivative of claim 1, wherein $R_1$ is selected from the group consisting of —H, —C$_m$H$_{(2m+1)}$, $C_3$-$C_7$ cycloalkyl, and —C$_m$H$_{(2m+1)}$ substituted by $C_3$-$C_7$ cycloalkyl.

3. The arylamino purine derivative of claim 1, wherein $R_2$ is selected from the group consisting of —H, —C$_m$H$_{(2m+1)}$, —OC$_m$H$_{(2m+1)}$, and —NHC$_m$H$_{(2m+1)}$.

4. The arylamino purine derivative of claim 1, wherein $R_4$ is selected from the group consisting of

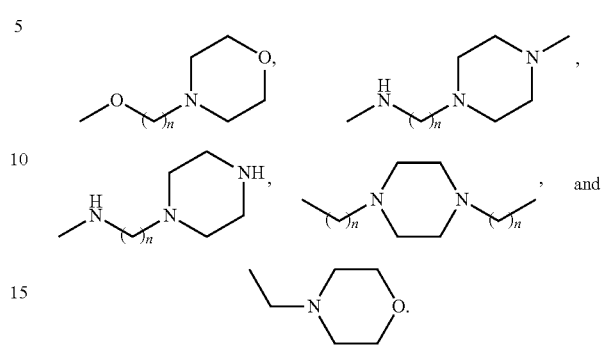

5. The arylamino purine derivative of claim 1, wherein $R_4$ is

6. The arylamino purine derivative of claim 1, wherein $R_1$ is selected from the group consisting of —H, —C$_m$H$_{(2m+1)}$,

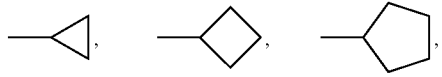

7. The arylamino purine derivative of claim 1, wherein the arylamino purine derivative is selected from the group consisting of:

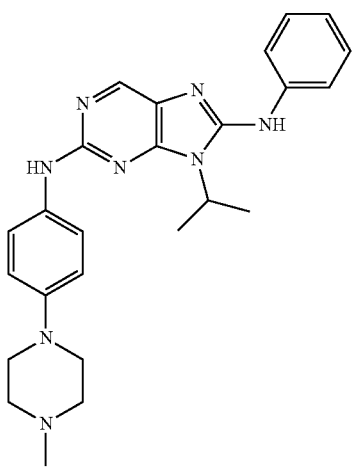

131
-continued
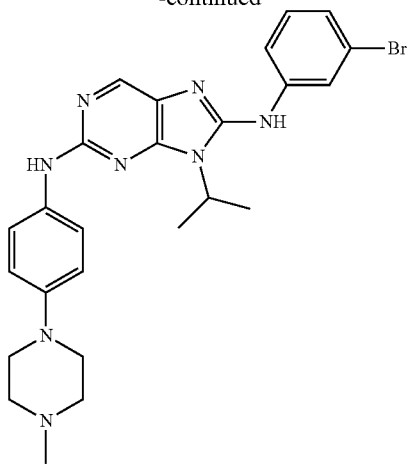
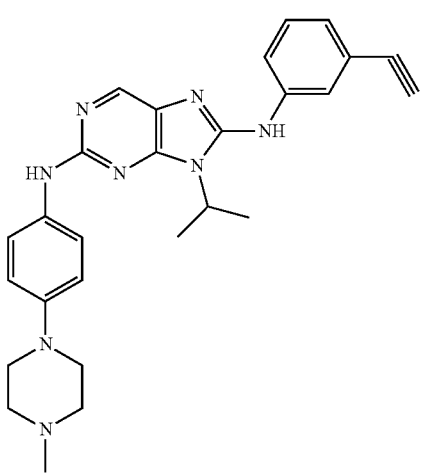
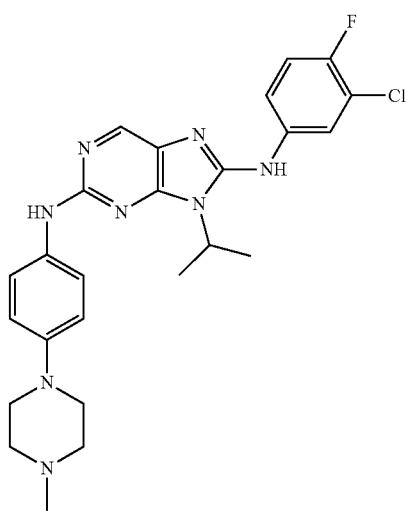
132
-continued
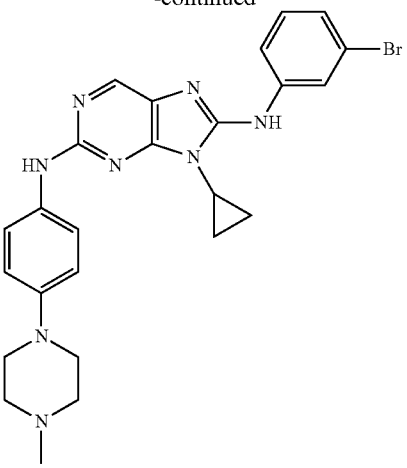
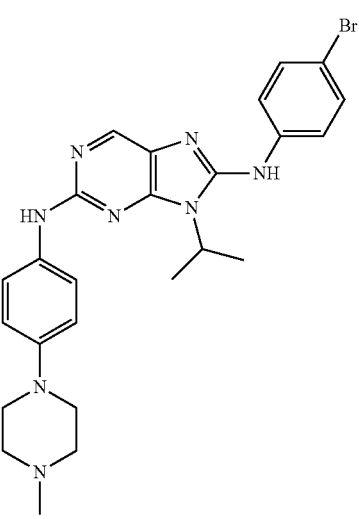
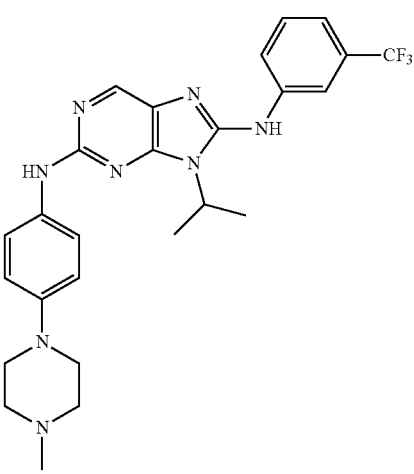

133
-continued
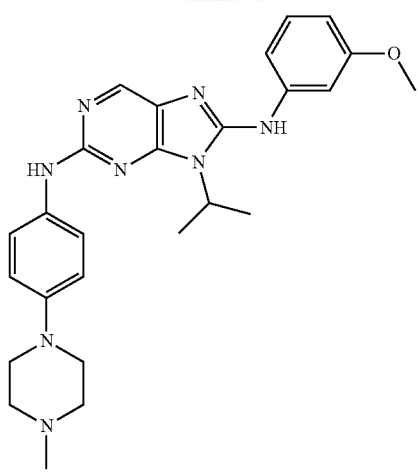
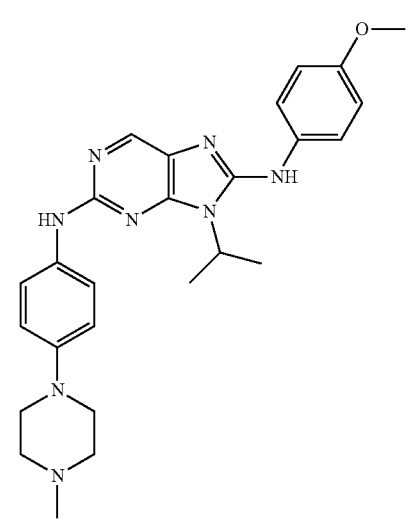
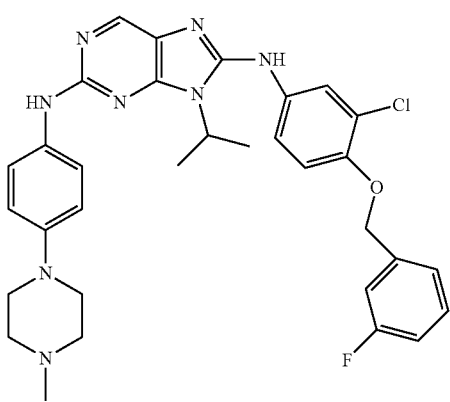
134
-continued
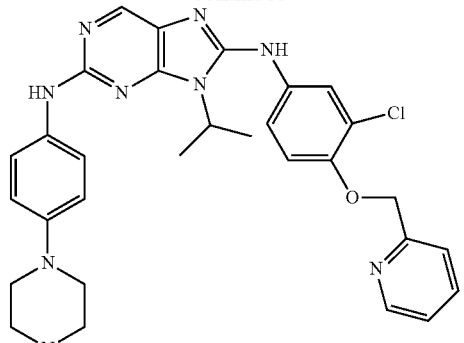
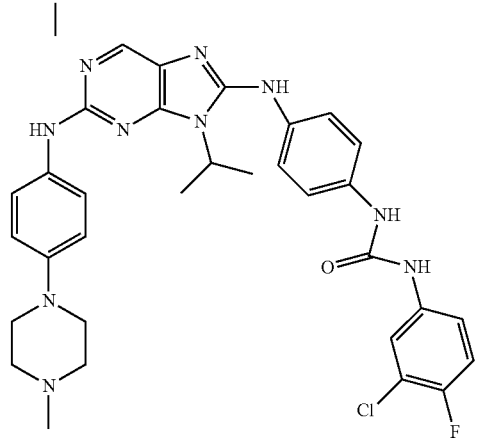
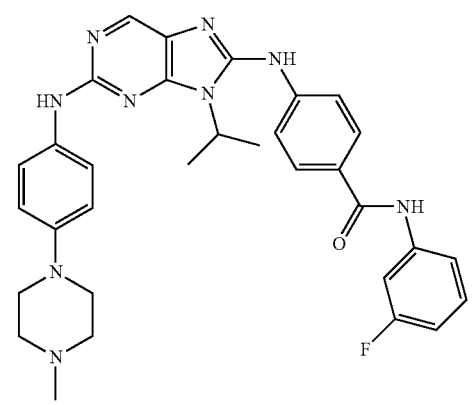
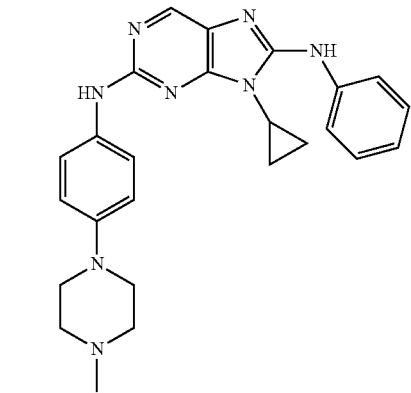

135
-continued
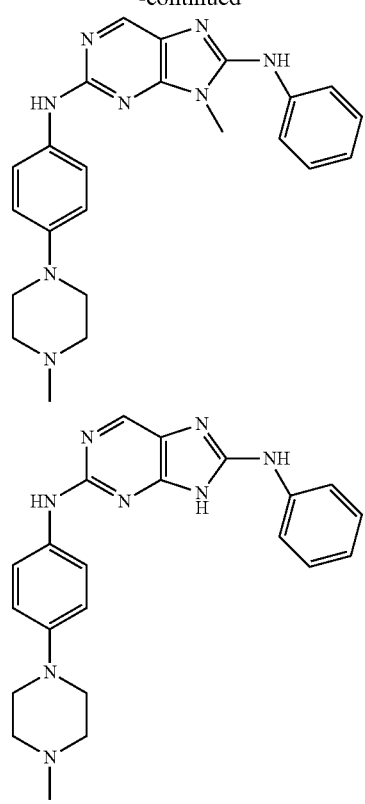
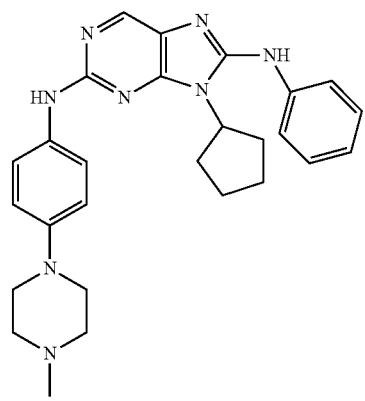
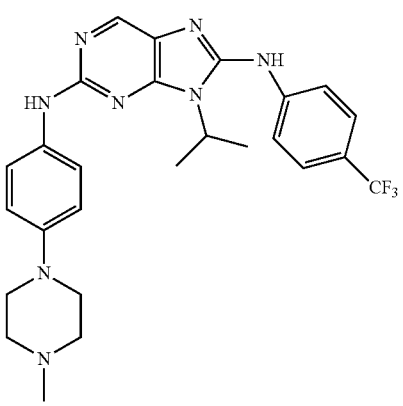
136
-continued
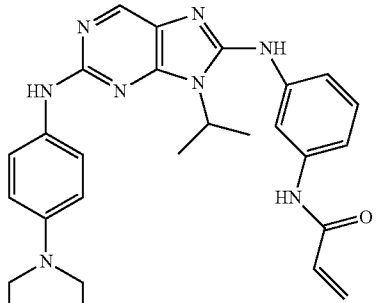
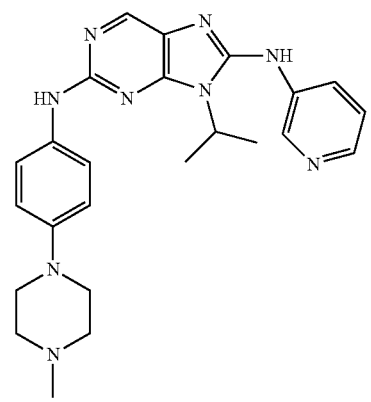
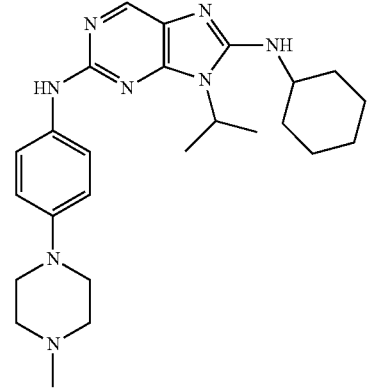
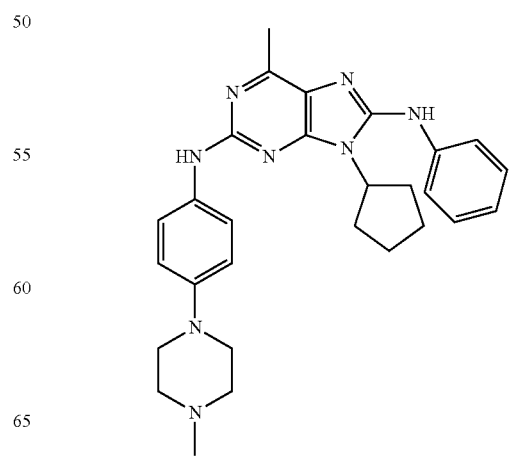

137
-continued
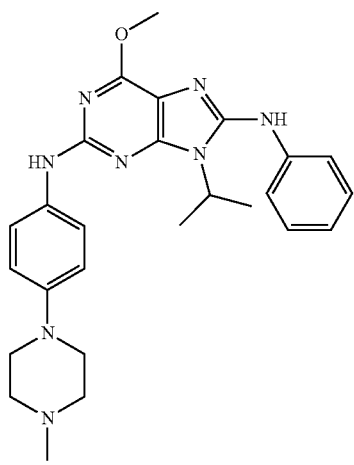
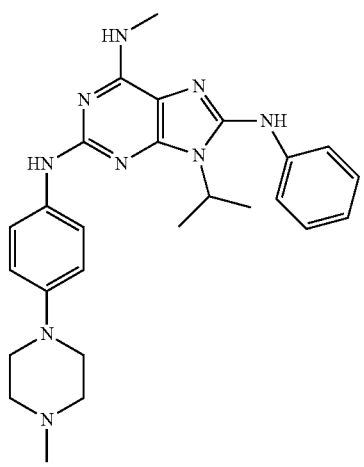
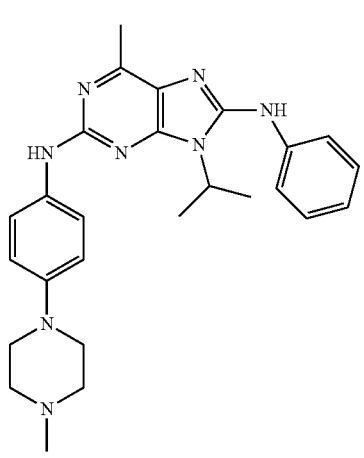
138
-continued
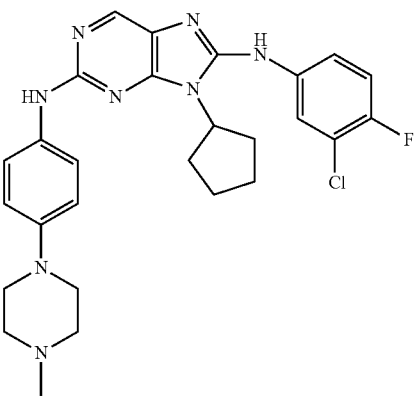
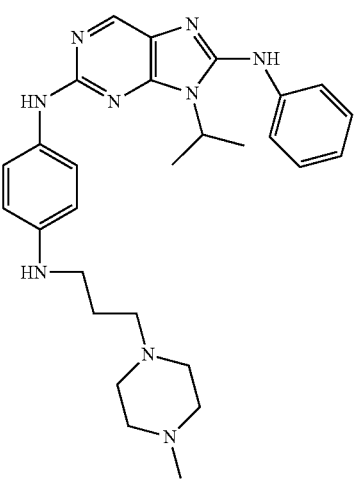

139
-continued
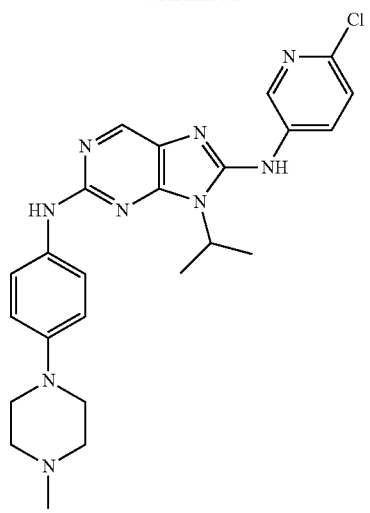
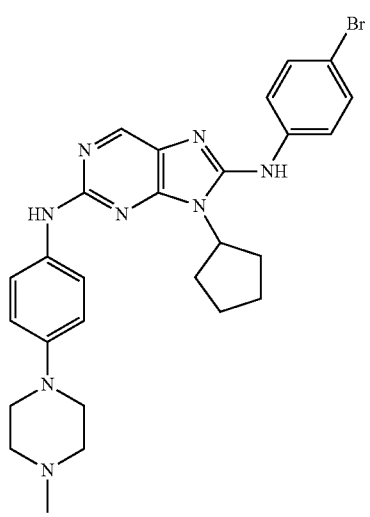
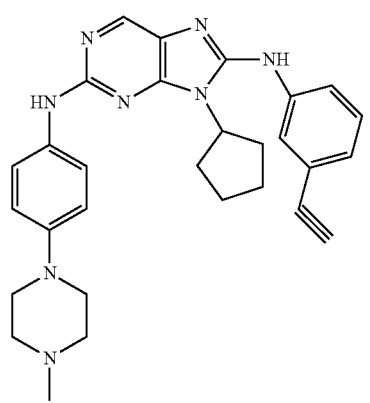
140
-continued
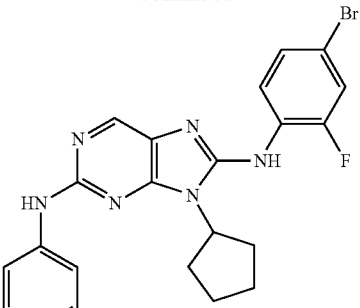
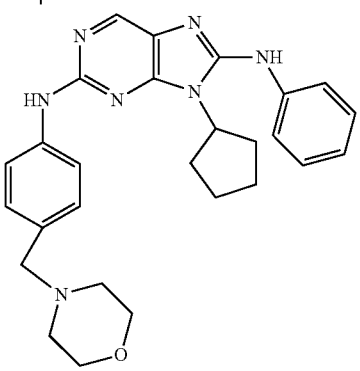
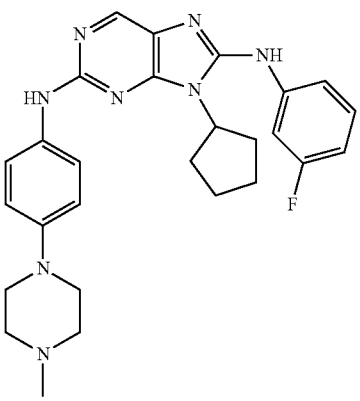
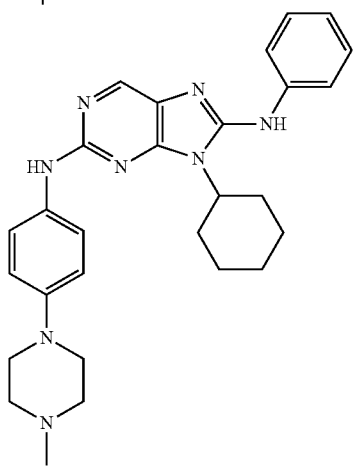

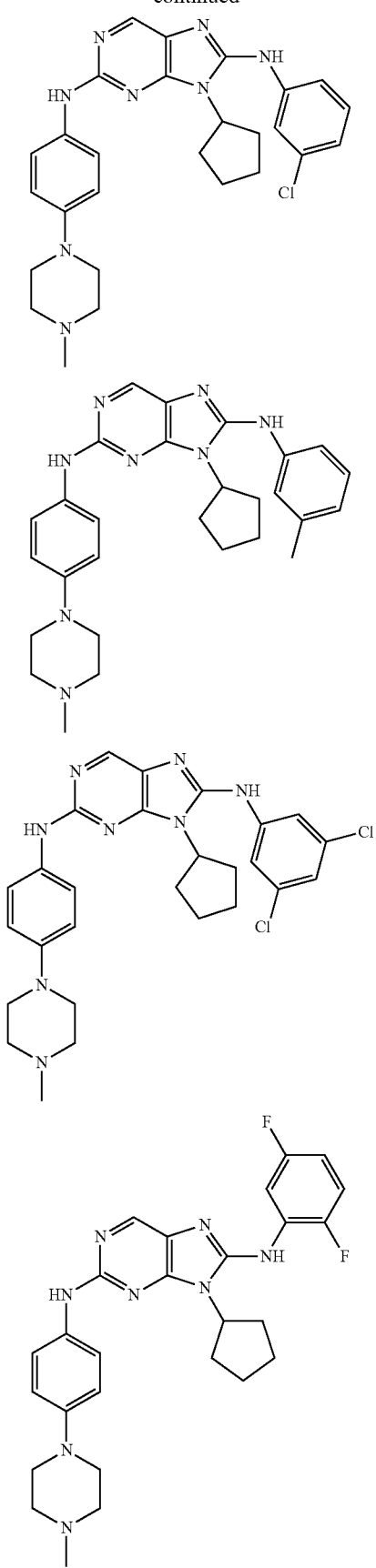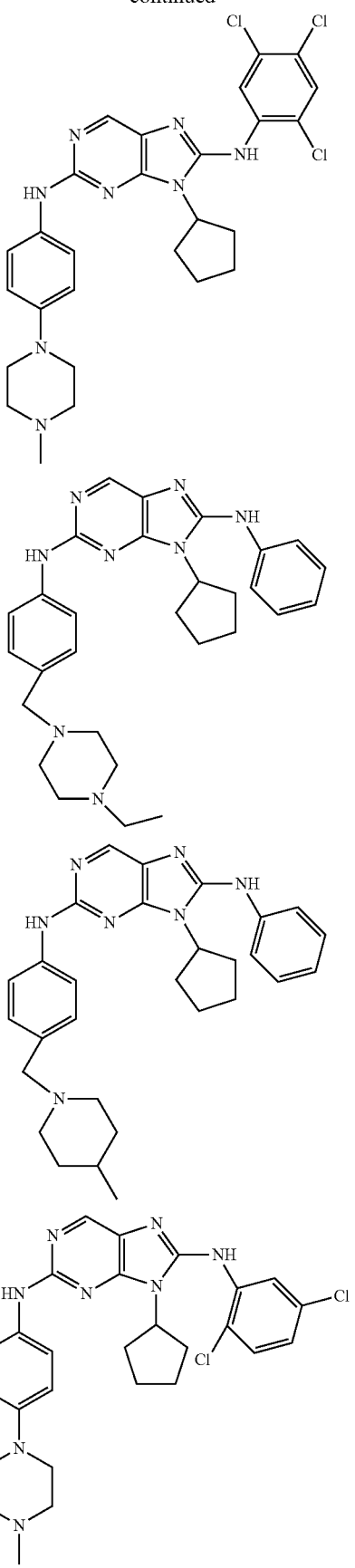

-continued

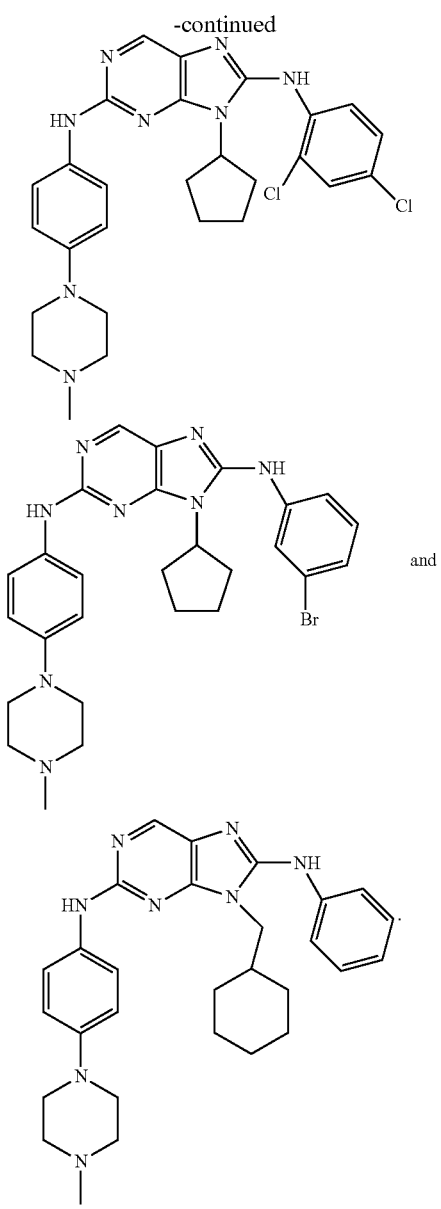

8. A method of treating tumors, comprising administering an effective amount of the arylamino purine derivative according to claim 1 to a subject in need thereof, wherein the tumors are selected from the group consisting of human non-small cell lung carcinoma, human acute myelogenous leukemia, human chronic granulocytic leukemia, human squamous cell carcinoma, human breast carcinoma, human colon cancer, human liver cancer, human gastric cancer, and human malignant melanoma.

9. A pharmaceutical composition comprising the arylamino purine derivative according to claim 1, or its pharmaceutical acceptable salt.

10. An arylamino purine derivative selected from the group consisting of:

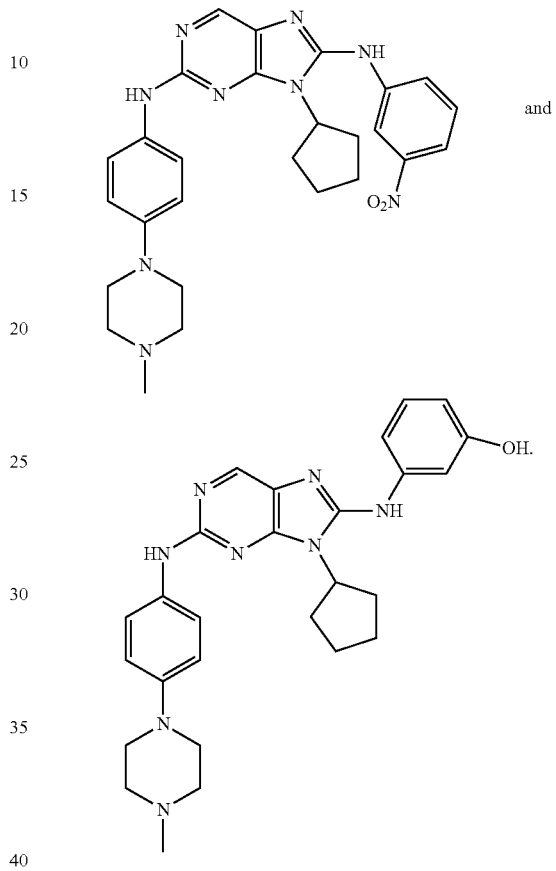

11. A method of treating tumors, comprising administering an effective amount of the arylamino purine derivative according to claim 10 to a subject in need thereof, wherein the tumors are selected from the group consisting of human non-small cell lung carcinoma, human acute myelogenous leukemia, human chronic granulocytic leukemia, human squamous cell carcinoma, human breast carcinoma, human colon cancer, human liver cancer, human gastric cancer, and human malignant melanoma.

12. A pharmaceutical composition comprising the arylamino purine derivative according to claim 10, or its pharmaceutical acceptable salt.

* * * * *